US010513542B2

(12) United States Patent
Puckette et al.

(10) Patent No.: US 10,513,542 B2
(45) Date of Patent: *Dec. 24, 2019

(54) MINICIRCLE DNA VECTOR VACCINE PLATFORM FOR FOOT-AND-MOUTH DISEASE AND METHODS THEREOF

(71) Applicant: The Government of the United States of America, as represented by the Secretary of Homeland Security, Washington, DC (US)

(72) Inventors: Michael Puckette, Waterford, CT (US); Max Rasmussen, Guilford, CT (US); John Neilan, Wethersfield, CT (US)

(73) Assignee: The Government of the United States of America, as represented by the Secretary of Homeland Security, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/957,376

(22) Filed: Apr. 19, 2018

(65) Prior Publication Data

US 2018/0244728 A1    Aug. 30, 2018

Related U.S. Application Data

(63) Continuation of application No. 14/962,272, filed on Dec. 8, 2015, now Pat. No. 9,975,926.

(51) Int. Cl.
| | | |
|---|---|---|
| *C07K 14/005* | (2006.01) | |
| *G01N 33/569* | (2006.01) | |
| *A61K 39/00* | (2006.01) | |

(52) U.S. Cl.
CPC ..... *C07K 14/005* (2013.01); *G01N 33/56983* (2013.01); *A61K 39/00* (2013.01); *C12N 2770/32122* (2013.01); *C12N 2770/32123* (2013.01); *C12N 2770/32134* (2013.01); *G01N 2333/09* (2013.01); *G01N 2469/20* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 5,354,670 | A | 10/1994 | Nickoloff et al. |
| 8,236,548 | B2 | 8/2012 | Chen et al. |
| 9,975,926 | B2* | 5/2018 | Puckette .............. C07K 14/005 |
| 2012/0258133 | A1 | 10/2012 | Charleston et al. |
| 2012/0315295 | A1 | 12/2012 | Rieder et al. |
| 2017/0158739 | A1 | 6/2017 | Puckette et al. |

FOREIGN PATENT DOCUMENTS

WO    2011/048353 A2    4/2011

OTHER PUBLICATIONS

Yang et al., "A novel minicircle vector based system for inhibiting the replication and gene expression of Enterovirus 71 and Coxsackievirus A16", Antiviral Research 96 (2012), p. 234-244.
Wang et al., "In Vivo Electroporation of Minicircle DNA as a novel method of vaccine delivery to enhance HIV-1-Specific Immune Responses", Journal of Virology, vol. 88, No. 4 (2014), p. 1924-1934.
De Crecy-Lagard, Valerie, "Identification of Genes Encoding tRNA Modification Enzymes by Comparative Genomics", Methods Enzymol, 2007, vol. 425, p. 153-183.
Green et al., "Characterization of the Mechanical unfolding of RNA Pseudoknots", J. Mol. Biol. (2008), vol. 375, p. 511-528.
Kay et al., "A robust system for production of minicircle DNA vectors", Nature Biotechnology, 2010, p. 1-5.
Kim et al., "Superluminescent variants of Marine Luciferases for Bioassays", Analytical Chemistry, 2011, vol. 83, p. 8732-8740.
Mayr et al., "Immune responses and protection against foot-and-mouth disease virus (FMDV) challenge in swine vaccinated with adenovirus-FMDV constructs", Vaccine, 19, 2001, p. 2152-2162.
Moraes et al., "Early protection against homologous challenge after a single dose of replication-defective human adenovirus type 5 expressing capsid proteins of foot-and-mouth disease virus (FMDV) strain A24", Vaccine, 20, 2002, p. 1631-1639.
Pacheco et al., "Rapid protecting of cattle from direct challenge with foot-and-mouth disease virus (FMDV) by a single inoculation with an adenovirus-vectored FMDV subunit vaccine", Virology, 337, 2005, p. 205-209.
Porta et al., "Efficient production of foot-and-mouth disease virus empty capsids in insect cells following down regulation of 3C protease activity", Journal of Virological Methods, 187, 2013, p. 406-412.
Rajaskekhar et al., "Rescue of infective virus from a genome-length cDNA clone of the FMDV serotype O (IND-R2/75) vaccine strain and its characterization", Research in Veterinary Science, 95, 2013, p. 291-297.
Montes et al., "Optimizing restriction site placement for synthetic genomes", Information and Computation, 213, 2012, p. 59-69.
Sequence Alignment of SEQ ID No. 4 with GENSEQ Database Access No. AAA13691 by Iadarola et al. WO 20001680 Jul. 2000.
Sequence Alignment of SEQ ID No. 5 with GENSEQ Database Access No. AAC8400 by Prusiner et al. WO 200068382 Nov. 2000.

* cited by examiner

*Primary Examiner* — Shanon A. Foley
(74) *Attorney, Agent, or Firm* — Lavanya Ratnam; Joseph Hsiao; Kelly G. Hyndman

(57) ABSTRACT

This application is directed generally to minicircle DNA vectors for the vaccination of foot-and-mouth disease (FMD). The transgene expression cassette in the minicircle DNA vector includes: a eukaryotic translation initiation nucleotide sequence, a mutant nucleotide sequence that encodes a foot-and-mouth disease virus (FMDV) capsid polyprotein precursor that contains at least one mutation to eliminate a restriction enzyme recognition site, a nucleotide sequence that encodes a protease that cleaves the FMDV capsid polyprotein precursor into a plurality of FMDV capsid proteins and a translational regulatory element to regulate the expression of the protease. The minicircle DNA vectors can be transfected directly into the cell of a mammalian host. When transfected into the mammalian host cell, virus-like particles can be produced intrinsically to stimulate the mammalian host's immune system to develop adaptive immunity toward foot-and-mouth disease.

43 Claims, 8 Drawing Sheets

Specification includes a Sequence Listing.

FIG. 4

Anti-VP2 (F14) — P1, 1ABC, VP0, VP2

Anti-VP3 — P1, 1CD, VP3

Anti-VP1 (12FE9) — P1, VP1

A  B  C

A = mc SGLuc
B = mc O1P1-3C(wt)
C = mc O1P1-HIV-3C(C142T)

FIG. 6 mc SGLuc mc O1P1-3C mc O1P1-HIV-
3C(C142T)

MINICIRCLE DNA VECTOR VACCINE PLATFORM FOR FOOT-AND-MOUTH DISEASE AND METHODS THEREOF

CROSS-REFERENCE TO RELATED APPLICATIONS

This application is a continuation of U.S. Ser. No. 14/962,272 filed Dec. 8, 2015, which is herein incorporated by reference in its entirety.

GOVERNMENT RIGHTS

This invention was made with government support under HSHQPM-12-X-00013 and HSHQDC-14-F-00035 awarded by the U.S. Department of Homeland Security. The Government has certain rights in this invention.

SEQUENCE LISTING

The instant application contains a Sequence Listing which has been submitted electronically in ASCII format and is hereby incorporated by reference in its entirety. The ASCII copy, created on Apr. 12, 2018, is named DHS-0167_ST25.txt and is 94 KB in size.

BACKGROUND

Technical Field

The present disclosure relates to compositions and methods for the vaccination and diagnosis of foot-and-mouth disease. More specifically, the present disclosure relates to a minicircle vector that is expressed in a mammalian host cell to produce virus-like particles of foot-and-mouth disease virus (FMDV).

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

The foot-and-mouth disease virus (FMDV), a prototypic *aphthovirus* within the Picornaviridae family, is the causative agent of a highly infectious and sometimes fatal disease that affects cloven-hoofed animals such as cattle, pigs, sheep, goats, deer and other animals with cloven hooves. There are seven major FMDV antigenically distinct virus serotypes (A, O, C, Asia 1 and South African Territories or SAT 1, 2 and 3) and multiple subtypes or topotypes exist within each serotype. Infection with any one serotype does not confer protective immunity against another. Serotype O is the most common serotype worldwide.

After an animal is infected with the FMDV, the first signs of illness usually appear within 2 to 14 days: high fever for 2-3 days followed by blisters inside the mouth and on the feet that may rupture and cause lameness.

FMD outbreaks cause significant agro-economic losses and severe implications for animal farming throughout much of the world. For example, the outbreak of FMD in the U.K. in 2001 was estimated to cost the U.K. £ 8 billion, including 6 million slaughtered livestock. Since the virus causing the disease is highly contagious and can be spread by infected livestock through aerosols, through contact with contaminated farming equipment, vehicles, clothing, or feed, and by domestic and wild predators, the containment of FMD demands considerable efforts in vaccination, strict monitoring, trade restrictions, and quarantines, and sometimes, the culling of animals.

BRIEF SUMMARY

According to a first aspect, the present disclosure provides a mutant nucleotide sequence that encodes a foot-and-mouth disease virus (FMDV) capsid polyprotein precursor, the mutant nucleotide sequence comprising a mutation that removed a restriction enzyme recognition site from a nucleotide sequence from which the mutant nucleotide sequence was formed.

In one or more embodiments, the nucleotide sequence comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 and combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the mutant nucleotide sequence comprises the nucleotide sequence of SEQ ID NO: 1.

In one or more embodiments, the restriction enzyme recognition site is selected from the group consisting of XbaI, XcmI, BsiWI, XhoI, BstEII, PflMI, AccI, NheI, SacII, PpuMI, AgeI, PvuII, NcoI, PstI, BstXI, AatI and combinations thereof.

In one or more embodiments, the FMDV is selected from the group consisting of O, A, C, Asia 1, SAT 1, SAT 2 and SAT 3 serotypes.

According to a second aspect, the present disclosure provides a vector comprising a mutant nucleotide sequence that encodes a foot-and-mouth disease virus (FMDV) capsid polyprotein precursor that includes a mutation that removed a restriction enzyme recognition site from a nucleotide sequence from which the mutant nucleotide sequence was formed.

In one or more embodiments, the vector further comprises a eukaryotic translation initiation nucleotide sequence positioned 5' to the mutant nucleotide sequence, a nucleotide sequence that encodes a protease, and a translational regulatory element positioned 3' to the mutant sequence and 5' to the nucleotide sequence that encodes the protease.

In one or more embodiments, the protease is functionally able to cleave the FMDV capsid polyprotein precursor into a plurality of FMDV capsid proteins.

In one or more embodiments, the FMDV capsid proteins are selected from a group consisting of VP0, VP1, VP2, VP3, VP4, and combinations thereof.

In one or more embodiments, the transitional regulatory element is functional to reduce expression of the protease relative to the nucleotide sequence that encodes the protease.

In one or more embodiments, the vector expresses the protease.

In one or more embodiments, the vector comprises a minicircle vector,

In one or more embodiments, the vector comprises the nucleotide sequence of SEQ ID NO: 2.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the mutant nucleotide sequence comprises the nucleotide sequence of SEQ ID NO: 1.

In one or more embodiments, the vector comprises the nucleotide sequence of SEQ ID NO: 3.

In one or more embodiments, the eukaryotic translation initiation nucleotide sequence comprises SEQ ID NO: 4.

In one or more embodiments, the eukaryotic translation initiation nucleotide sequence comprises SEQ ID NO: 5.

In one or more embodiments, the translational regulatory element comprises a DNA or RNA sequence responsible for a ribosomal frameshift.

In one or more embodiments, the DNA or RNA sequence responsible for a ribosomal frameshift is selected from the group consisting of an ALIL pseudoknot, an antizyme RNA frameshifting stimulation element, a coronavirus frameshifting stimulation element, a DnaX ribosomal frameshifting element, a HIV ribosomal frameshift signal, an insertion sequence IS1222 ribosomal frameshifting element, and a ribosomal frameshift.

In one or more embodiments, the DNA or RNA sequence responsible for a ribosomal frameshift is functional to mediate a translational frameshift in the protease in an amount of 90-95% of translated protease mRNA.

In one or more embodiments, the DNA or RNA sequence responsible for a ribosomal frameshift is functional to yield translation of no more than twenty percent (20%) of the nucleotide sequence that encodes the protease after translation.

In one or more embodiments, the DNA or RNA sequence responsible for a ribosomal frameshift is functional to yield translation of between five and ten percent (5-10%) of the nucleotide sequence that encodes the protease after translation.

In one or more embodiments, the nucleotide sequence that encodes the protease is fully translated and comprises a correct translation of the protease after translation.

In one or more embodiments, the DNA or RNA sequence responsible for a ribosomal frameshift comprises the nucleotide sequence of SEQ ID NO: 6.

In one or more embodiments, the nucleotide sequence that encodes a protease comprises the nucleotide sequence of SEQ ID NO: 7, and the amino acid sequence of the protease comprises SEQ ID NO: 8.

In one or more embodiments, the nucleotide sequence that encodes a protease comprises SEQ ID NO: 9.

In a third aspect, the present disclosure provides a transformed host cell comprising a mutant nucleotide sequence that encodes a foot-and-mouth disease virus (FMDV) capsid polyprotein precursor that includes a mutation that removed a restriction enzyme recognition site from a nucleotide sequence from which the mutant nucleotide sequence was formed.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the transformed host cell comprises a mammalian cell.

In one or more embodiments, the transformed host cell is functional to produce a virus like particle (VLP).

In one or more embodiments, the VLP comprises a FMDV VLP.

In a fourth aspect, the present disclosure provides virus like particle (VLP) comprising a polypeptide produced from expression of a vector comprising a mutant nucleotide sequence that encodes a foot-and-mouth disease virus (FMDV) capsid polyprotein precursor and includes a mutation that removed a restriction enzyme recognition site from a nucleotide sequence from which the mutant nucleotide sequence was formed.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the vector further comprises a eukaryotic translation initiation nucleotide sequence positioned 5' to the mutant nucleotide sequence, a nucleotide sequence that encodes a protease, and a translational regulatory element positioned 3' to the mutant sequence and 5' to the nucleotide sequence that encodes the protease.

In a fifth aspect, the present disclosure provides a method of vaccinating a mammal against a foot-and-mouth disease virus (FMDV), comprising administering a vector comprising a mutant nucleotide sequence which when expressed in a host cell of the mammal induces production of foot-and-mouth disease virus virus-like particles (VLP) by the host cell, the mutant nucleotide sequence encodes a FMDV capsid polyprotein precursor and includes a mutation to remove a restriction enzyme recognition site from a nucleotide sequence from which the mutant nucleotide sequence was formed.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the method further comprises administering an adjuvant with the vector.

In a sixth aspect, the present disclosure provides a method of determining whether a mammal is vaccinated against or infected with foot-and-mouth disease virus (FMDV) comprising detecting an antibody's presence in a sample from the mammal, and detecting an other antibody's presence or absence in the sample, the absence of the other antibody indicates vaccination of the mammal with a vector comprising a mutant nucleotide sequence which when expressed in a host cell of the mammal induces production of FMDV virus-like particles, the mutant nucleotide sequence encodes a FMDV capsid polyprotein precursor and a mutation to remove a restriction enzyme recognition site from a nucleotide sequence from which the mutant nucleotide sequence was formed.

In one or more embodiments, the mutant nucleotide sequence further comprises at least one of one through twenty-two (1-22) silent mutations, one through fifteen (1-15) silent mutations, or one through ten (1-10) silent mutations that removed one or more restriction enzyme recognition sites.

In one or more embodiments, the one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1338, T1518, C1578, T1593, C1665, C1836, C2010, A2190 or combinations thereof.

In one or more embodiments, the one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T, and combinations thereof.

In one or more embodiments, the mammal produced the antibody responsive to vaccination with the vector.

In one or more embodiments, the other antibody comprises a plurality of antibodies that do not include the antibody.

In one or more embodiments, the plurality of antibodies comprise antibodies against FMDV non-structural proteins.

In one or more embodiments, the plurality of antibodies are associated with FMDV infection.

In one or more embodiments, the detecting the antibody's presence implements an immunoassay.

In one or more embodiments, immunoassay comprises an enzyme linked immunosorbent assay (ELISA).

In one or more embodiments, the detecting the other antibody's presence or absence implements an immunoassay.

In one or more embodiments, the immunoassay comprises an enzyme linked immunosorbent assay (ELISA).

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

An appreciation of the disclosure and many of the attendant advantages thereof may be understood by reference to the accompanying drawings. Included in the drawings are the following figures:

FIG. 4 illustrates gene layouts of three inserts that were each individually cloned into a minicircle vector system.

FIG. 6 is a western blotting image of transfected cells reacted with F14 anti-VP2, anti-VP3 and 12FE9 antibodies to examine FMDV P1 processing in transfected cells.

DETAILED DESCRIPTION OF THE EMBODIMENTS

Overview

Figure 1:
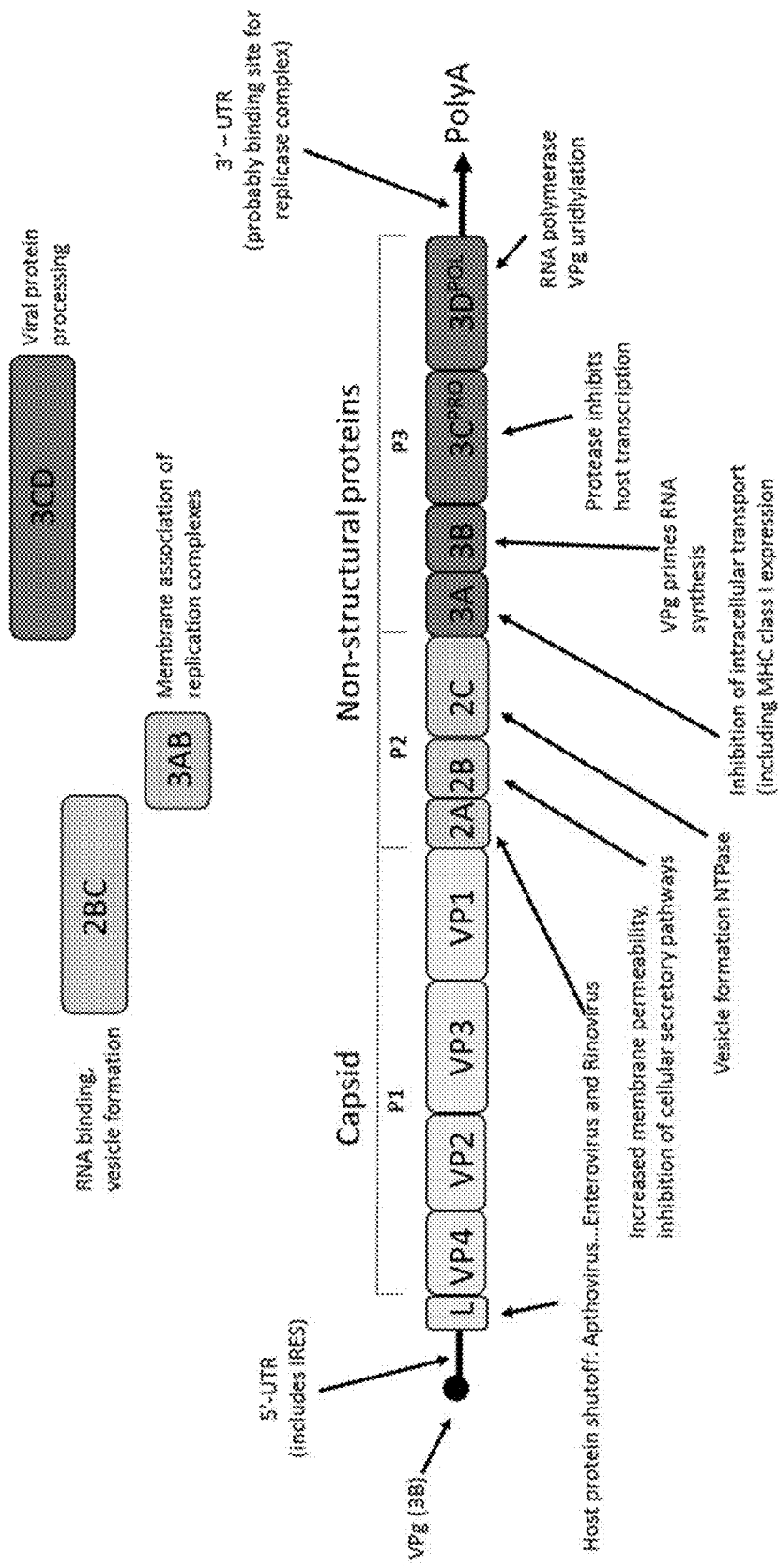
FIG. 1 is a diagrammatic representation of the picornavirus genome that includes translated capsid and other non-structural proteins.

Some vaccine includes the use of a whole virus that is either killed or inactivated, such as by chemically inactivating the virus, or is attenuated by various means. Vaccines are fraught with limitations and shortcomings, such as potential virus escape, vaccine instability (e.g., loss of immunogenicity during transportation and storage), short duration of immunity and the use of multiple antigens (e.g., dozens) to address viral mutation, evolution and antigenic diversity. Furthermore, the set-up and running costs of the vaccine production facilities are very high, and the antibody profiles animals vaccinated with the whole virus may not be easily distinguished from those of infected animals.

Description

Referring now to the drawings, wherein like reference numerals designate identical or corresponding parts throughout the several views.

For purposes of the present invention, "foot-and-mouth-disease virus" or the acronym FMDV refers to any of the seven major FMDV antigenically distinct virus serotypes, i.e. A, O, C, Asia 1 and South African Territories 1, 2 and 3 as well as the multiple subtypes or topotypes exist within each serotype. Infection with any one serotype does not confer protective immunity against another. The FMDV is a non-enveloped picornavirus (belonging to the genus *Aphthovirus* of the family Picornaviridae) with a single-stranded genomic RNA of between 7,500 to 8,000 nucleotides or approximately between 7,500 to 8,000 nucleotides, approximately 7,500 nucleotides, or approximately 8,000 nucleotides. The capsid, which is the protein shell of the virus, is made up of 60 copies of each of the four structural proteins VP1, VP2, VP3 and VP4 (see FIG. 1). In embodiments, during assembly, P1, a 95-kDa capsid polyprotein precursor is cleaved by the viral 3C protease to ultimately yield VP1, VP2, VP3 and VP4. As shown in FIG. 1, apart from the 3C protease, the FMDV also expresses several other non-structural or non-capsid proteins (e.g. 2A-C, 3A-D) that can be involved in virus replication and various cellular functions.

The present disclosure provides compositions comprising recombinant foot-and-mouth disease virus (FMDV) nucleic acids and/or proteins for use in vaccine formulations and diagnostic reagents, as well as methods of preparing the compositions.

In particular, these compositions include mutant FMDV nucleotide sequences and transgene expression cassettes. In some embodiments, the compositions further comprise vehicles to carry and transfer the transgene expression cassette such as vectors (preferably minicircle vectors) and host cells (preferably mammalian cells) wherein the transgene expression cassette may be expressed and/or replicated.

For purposes of the present disclosure, a "nucleotide sequence" or "nucleic acid sequence" is a succession of letters that indicate the order of nucleotides or nucleic acids within a DNA (using GACT) or RNA molecule (using GACU). The DNA or RNA molecule may be single or double stranded and may be genomic, recombinant, mRNA or cDNA.

For purposes of the present disclosure, a "transgene expression cassette" or "transgene expression construct" is a nucleic acid sequence that has been artificially constructed to comprise one or more functional units (e.g. promoter, control element, consensus sequence, translational frameshift sequence, protein encoding gene etc.) not found together in nature, and is capable of directing the expression of any RNA transcript in an organism that the cassette has been transferred to, including gene encoding sequence(s) of interest as well as non-translated RNAs, such as shRNAs, microRNAs, siRNAs, anti-sense RNAs. A transgene expression cassette may be single- or double-stranded and circular or linear. A transgene expression cassette can be constructed, inserted or cloned into a "vector", which serves as a vehicle for transferring, replicating and/or expressing nucleic acid sequences in target cells.

The transgene expression cassette according to the disclosure can be constructed as a single open reading frame. The transgene expression cassette includes a consensus nucleotide sequence for eukaryotic translation initiation (e.g., Kozak consensus sequence), a nucleotide sequence that encodes a FMDV capsid polyprotein precursor that contains at least one mutation to eliminate a restriction enzyme recognition site, a nucleotide sequence that encodes a protease that cleaves the capsid polyprotein precursor and a translational regulatory element to regulate the expression of the protease.

The transgene expression cassette described in accordance with embodiments described herein does not encode the complete FMDV genome and therefore cannot cause an accidental FMD outbreak during manufacture, or administration of the vaccine containing the transgene expression cassette.

Furthermore, the transgene expression cassette encodes only the P1 and 3C FMDV viral proteins. Animals treated with a vaccine containing the transgene expression cassette will not produce antibodies to other FMDV viral proteins that are expressed during a natural FMDV infection. For example, if the transgene expression cassette contains a nucleotide sequence that encodes the 2B protein, the animal treated with the vaccine containing the transgene expression cassette containing a nucleotide sequence that encodes the 2B protein will only produce antibodies for the 2B protein and not antibodies for other viral proteins such as 2C, 3B, 3D, etc. The difference in antibody profiles produced after natural infection compared to vaccination with the transgene expression cassette confers the ability to differentiate infected animals from vaccinated animals and vice versa.

Figure 2:
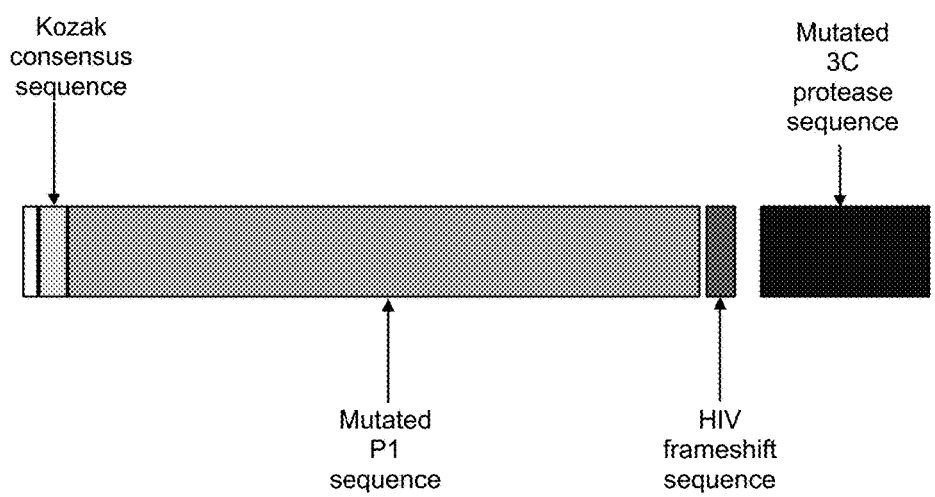
FIG. 2 illustrates the organization and design of the multiple functional units of a transgene expression cassette according to one embodiment.

FIG. 2 shows an embodiment of the transgene expression cassette that is arranged as follows: Kozak consensus sequence-Mutated P1 nucleotide sequence from FMDV-HIV frameshift sequence-Mutated 3C protease nucleotide sequence from FMDV.

In one or more embodiments, the nucleotide sequence of the transgene expression cassette comprises SEQ ID NO: 2.

The Kozak consensus sequence is a sequence which occurs in eukaryotic mRNA and, in one or more embodiments, comprises SEQ ID NO: 4. The Kozak consensus sequence plays a major role in the initiation of the translation process. In some instances the Kozak consensus sequence plays an essential role in initiation of the translation process, e.g., it is substantially the sole determining factor in initiation of the translation process.

In one or more embodiments, the Kozak consensus sequence is a Kozak eukaryotic translation initiation sequence comprising SEQ ID NO: 5.

In principle, effective FMDV vaccines can be produced from recombinant VLPs. However, the formation of stable VLPs in host cells at concentrations high enough to stimulate immune responses are hindered by the viral 3C protease. The 3C protease is used for proper processing and cleaving of the P1 polyprotein precursor, and has been found to be toxic to the host cells. Furthermore, the empty recombinant particles such as empty capsids tend to be less stable than in comparison to virus particles containing nucleic acid.

In some embodiments, the expression of the 3C protease from the transgene expression cassette is down regulated in such a way so the levels of enzyme are reduced or the expressed enzyme is not cytotoxic yet maintains the P1 cleavage activity for capsid formation. This may be achieved by engineering of the enzyme by rational design (e.g., site-directed mutagenesis) and/or random mutagenesis (e.g., directed evolution followed by screening of the desired enzyme properties) wherein one or more mutations may be introduced to the recombinant gene that encodes the protease. In certain embodiments, the 3C protease contains a mutation at cysteine residue 142. The cysteine may be substituted by another residue, for example, a threonine or an alanine.

In one or more embodiments, the nucleotide sequence of the mutated 3C protease comprises SEQ ID NO: 9 and the amino acid sequence of the mutated 3C protease comprises SEQ ID NO: 10.

In one or more embodiments, the 3C protease in the transgene expression cassette is derived from FMDV Asia Lebanon 1989 strain (serotype Asia-1).

In one or more embodiments, the 3C protease in the transgene expression cassette is derived from FMDV A22 Iraq strain (serotype A).

Alternatively, the expression of 3C protease may be controlled or suppressed with a translational element or a DNA or RNA sequence responsible for a ribosomal frameshift such as ALIL pseudoknot, antizyme RNA frameshifting stimulation element, coronavirus frameshifting stimulation element, DnaX ribosomal frameshifting element, HIV ribosomal frameshift signal, insertion sequence IS1222 ribosomal frameshifting element and a ribosomal frameshift. The DNA or RNA sequence responsible for a ribosomal frameshift may be located upstream of the nucleotide sequence that encodes the protease and downstream of the nucleotide sequence that encodes the capsid polyprotein precursor in the transgene expression cassette, and may cause a frameshift event of occurring in 80-98% of the total translation events. In certain embodiments, the DNA or RNA sequence responsible for a ribosomal frameshift mediates a translational frameshift in the protease in an amount of 90-95% of translated protease mRNA. This results in a small fraction of no more than 20%, preferably 5-10% of the nucleotide sequence that encodes the protease (e.g. 3C protease) downstream of the frameshift element being fully translated with the correct open reading frame.

Frameshifts resulting from ribosomal frameshifting are controlled by various mechanisms found in codons. These mechanisms emerge from the fact that ribosomes do not translate proteins at a steady rate, regardless of the sequence. Certain codons take longer to translate, because there are not equal amounts of tRNA of that particular codon in the cytosol. Due to this lag, there exist in small sections of codons sequences that control the rate of ribosomal frameshifting. Sections of less accessible codons that slow ribosomal transaction are known as "choke points," and sections of easily accessible codons which result in faster ribosomal transaction are "slippery sequences." Slippery sequences can potentially make the reading ribosome "slip" and skip a number of nucleotides (usually only 1) and read a completely different frame thereafter. Choke points reduce the probability of this happening (de Crecy-Lagard, V. *Identification of genes encoding tRNA modification enzymes by comparative genomics*. Methods in Enzymology. 2007 425: 153-83; Green, L., Kim, C. H., Bustamante, C., Tinoco Jr, I. *Characterization of the mechanical unfolding of RNA pseudoknots*. J Mol. Biol. 2008 375(2):511-28; US Patent Publication No. 20120258133—each incorporated herein by reference in its entirety).

In addition to 3C, Leader (L) and 2A proteins of picornaviruses including the FMDV (see FIG. 1) are responsible for proper viral polyprotein processing. Therefore, wild-type and mutant nucleotide sequences that encode the L and 2A proteins may be used to construct the transgene expression cassette described herein for processing of the P1 capsid polyprotein precursor.

To enhance the stability of the final assembled capsid product, mutagenesis strategies and techniques as previously described may be applied to introduce one or more mutations to the nucleotide sequence that encodes the polyprotein precursor. In one or more embodiments, the nucleotide sequence is 2256 nucleotides in length and encodes the P1 polyprotein precursor derived from the FMDV O1 Manisa isolate 87 strain (serotype O). Among the mutations that can be introduced include silent mutations that effectively eliminate restriction enzyme recognition sites to better facilitate cloning and sub-cloning yet maintain the same translated protein product by not causing any amino acid substitution. These mutations enhance the cloning in and cloning out of the P1 polyprotein precursor into a transgene expression cassette to swap different P1 polyprotein precursors from different FMDV serotypes to promptly respond to the needs of individual outbreaks.

In one or more embodiment, the mutations to the DNA coding sequence of the P1 polyprotein precursor include changes to one or more of C99, C285, T345, G354, A369, C408, C468, G498, C528, A588, C597, C627, C957, G1170, T1338, T1518, C1578, T1593, C1665, C1836, C2010, A2190 or combinations thereof, from one pyrimidine base to another pyrimidine base, from one purine base to another purine base, or to any other base as long as the mutation does not result in an amino acid change upon translation. In one or more embodiments, the nucleotide substitutions are: C99T, C285T, T345A, G354A, A369G, C408T, C468A, G498A, C528T, A588T, C597T, C627T, C957A, G1170C, T1338C, T1518C, C1578A, T1593A, C1665G, C1836G, C2010T, A2190T or combinations thereof, from one pyrimidine base to another pyrimidine base, from one purine base to another purine base, or to any other base as long as the mutation does not result in an amino acid change upon translation.

Figure 3:
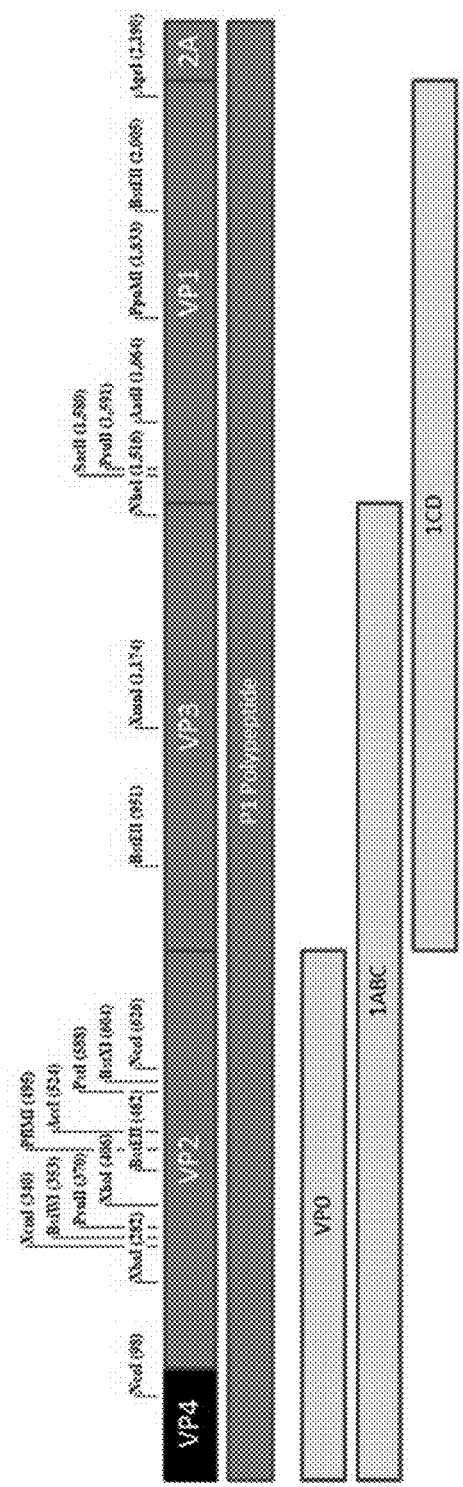
FIG. 3 is a schematic diagram illustrating the locations of multiple restriction enzyme recognition sites in the P1 polyprotein precursor according to one embodiment.

In one or more embodiments, the restriction enzyme recognition sites that are eliminated by the mutations to the P1 polyprotein precursor include, as shown in FIG. 3, XbaI, XcmI, BsiWI, XhoI, BstEII, PflMI, AccI, NheI, SacII, PpuMI, AgeI, PvuII, NcoI, PstI, BstXI and AatI.

To ensure cessation of mRNA translation, a stop codon sequence (i.e., TAA, TGA, or TAG) may be added to the end of the transgene expression cassette.

In one or more embodiments, the mutated P1 polyprotein precursor comprises nucleotide sequence SEQ ID NO: 1. The nucleotide sequence of a wild-type P1 polyprotein precursor derived from FMDV O1 Manisa isolate 87 comprises SEQ ID NO: 11.

In one or more embodiments, the mutated P1 polyprecursor comprises a mutant nucleotide sequence of a P1 polyprecursor derived from any of the seven major FMDV antigenically distinct virus serotypes, i.e., A, O, C, Asia 1 and South African Territories 1, 2 and 3 as well as the multiple subtypes or topotypes exist within each serotype. The wild-type nucleotide sequences of the P1 polyprotein precursor from various FMDV serotypes are known, for example SEQ ID NO: 11 (O1 Manisa isolate 87), SEQ ID NO: 12 (Type A (A/IRN/1/96)), SEQ ID NO: 13 (Type C (Haute Loire FR/69)), SEQ ID NO: 14 (SAT3 ZAM/04/96/3), SEQ ID NO: 15 (SAT2 SEN/05/75), SEQ ID NO: 16 (SAT1 NIG/15/75) and SEQ ID NO: 17 (Asia 1 IND 63/72).

The present disclosure further provides vectors or vehicles containing the transgene expression cassette. Example vectors include, but are not limited to, circular or linear, single- or double-stranded, natural or engineered extrachromosomal plasmid vectors, cosmids, viral vectors, expression vectors, gene transfer vectors, minicircle vectors, and artificial chromosomes and typically contain at least an origin of replication, a cloning site and a selectable marker (e.g., antibiotic resistance). Natural versions of the foregoing examples may be isolated, purified, and/or modified so the resultant natural version is differentiable from the material in its natural state.

In an embodiment, the vector used for transferring the transgene expression cassette is a minicircle DNA vector. A "minicircle DNA vector" may be referred to as "minicircle vector" or "minicircle" is a small (usually in the range of 3-4 kb, approximately 3-4 kb or usually no larger than 10 kb) circular, episomal plasmid derivative wherein all prokaryotic vector parts (e.g., bacterial origin of replication, genes associated with bacterial propagation of plasmids) have been removed. Since minicircle vectors contain no prokaryotic DNA sequences, they are less likely to be perceived as foreign and destroyed when they are employed as vehicles for transferring transgenes into target mammalian cells. In embodiments, a minicircle DNA vector is a minicircle carrying a transgene expression cassette. In examples, a minicircle DNA vector is a minicircle carrying a transgene expression cassette and does not contain an empty vector without an insert.

The use of a minicircle DNA vector to carry and transfer the transgene expression cassette allows mammalian cells to be transfected (e.g., directly) without utilizing an intermediate eukaryotic host system (e.g., insect cell line production system). In embodiments, "transfection" is the process of deliberately introducing nucleic acid into eukaryotic cells, such as animal cells. Transfection can eliminates the costs and labor associated with maintaining large volumes of intermediate host cell cultures in production facilities and harvesting empty capsids or VLPs produced by intermediate host cells.

Furthermore, the size of minicircle vectors (which are smaller than standard plasmid vectors) and the lack of extraneous bacterial sequences enhance transfection of cells and enable an extended duration of transgene expression within the mammalian host cell. For example, a minicircle vector is smaller than a standard vector as it lacks extraneous bacterial sequences found on plasmids. Differences in size between plasmid vectors and minicircle vectors can be attributed to the lack of extraneous bacterial sequences, inclusion of an insubstantial amount of extraneous bacterial sequences in comparison to the overall size of the vector, such as appreciably smaller in comparison to the plasmid, and variations thereof. Prolonged high levels of transgene expression by minicircles in mammalian hosts can also be facilitated by in the incorporation of strong and constitutive promoters such as SV40, CMV, UBC, EF1A, PGK and CAGG.

In one or more embodiments, the nucleotide sequence of a minicircle containing the transgene expression cassette comprises SEQ ID NO: 3.

The present disclosure additionally provides methods of producing minicircle vectors that are capable of inducing production of FMDV virus-like particles in mammalian host cells and methods of vaccinating a mammalian subject with the minicircle vectors.

Minicircle vectors are prepared using a two-step procedure. Firstly, a full-size parental plasmid containing bacterial sequences and transgene is produced in, for example, *Escherichia coli*. While the parental plasmid is still inside the *E. coli* host, the expression of a site-specific recombinase is induced and the prokaryotic or bacterial bone is excised by the enzyme at the recombinase recognition sites. Examples of site-specific recombinases include Tyr- and Ser-recombinases such as Cre recombinase, Flp recombinase, ParA resolvase and PhiC31 integrase. The resulting minicircle vector is recovered by capillary gel electrophoresis. An example of suitable materials, techniques, approaches, and methods are described in U.S. Pat. No. 8,236,548 which is hereby incorporated by reference in its entirety. Further description may be found in Kay et al, *A Robust System for Production of Minicircle DNA Vectors*, Nature Biotechnology, 2010 28:1287-1289, which is hereby incorporated by reference in its entirety.

A vaccine in embodiments in accordance with the present disclosure is a biological composition that provides or improves immunity to an organism to a particular disease. A vaccine may contain an agent, such as a killed, inactivated, weakened or attenuated form of the disease-causing microorganism (e.g., virus, bacteria, fungi, algae), its toxins, surface proteins or recombinant nucleic acid such as DNA, compositions or particles that resemble the pathogenic microorganism (e.g., virus-like particles) or combinations thereof. The agent functions as an antigen and is administered to an organism to stimulate the body's immune system to produce an immune response, which may include recognizing the agent as foreign, destroying the agent (e.g., with antibodies produced that are specific to the agent/antigen), and remembering the agent, so the immune system can more easily recognize and destroy any of these microorganisms that it later encounters, for example, an infection.

Virus-like particles, or VLPs, can be used in accordance with embodiments of the present disclosure. VLPs are recombinant particles with viral matrix or structural proteins such as capsids that resemble viruses, but are non-infectious and unable to propagate as they, respectively, do not contain any viral genetic material. VLPs can be utilized as vaccine antigens as they mimic the native virions, and can be produced in vitro in a variety of cell culture systems including mammalian cell lines, insect cell lines, yeast and plant cells or in vivo. In embodiments, FMDV VLPs consist essentially of assembled structural proteins or assembled capsid proteins (e.g., VP1, VP2, VP3 and VP4).

In DNA vaccination, an organism is protected against a disease by injecting it with genetically engineered DNA (e.g., transgene+vector) to produce an immune response. DNA vaccines have a number of advantages over traditional whole-pathogen vaccines and protein-based vaccines. For example, DNA vaccines do not contain an actual infectious agent, whether dead or alive. DNA vaccines can also be easily lyophilized for long-term storage and transportation and do not require any cold chain delivery.

The DNA vector inside a DNA vaccine can be produced and modified more quickly and more easily in comparison to traditional vaccine preparation. This allows a more rapid response to specifically engineer DNA vaccines tailored to individual FMD outbreaks (e.g., a DNA vaccine matching a specific FMDV outbreak strain or serotype). Using a minicircle DNA vector to carry and transfer the transgene expression cassette eliminates the use of an intermediate eukaryotic host system and the associated costs and labor, including modification of an intermediate host system during and outbreak, such as during the onset of an FMD outbreak.

Routes of DNA vaccine administration include, but are not limited to, traditional injection methods in saline (e.g. subcutaneous, intradermal and intramuscular injections), jet injection, oral administration, skin patches, aerosol inhalation or instillation, topical administration to the eye, electroporation, gene gun, transfection, liposome-mediated delivery or combinations thereof.

An FMD DNA vaccine in accordance with embodiments of the present disclosure are administered at dosages such as in the range of 25-1000 µg of the minicircle DNA vector in saline solution or another appropriate diluent, in the range of between 50-500 µg, in the range of 100-250 µg. A variety of factors can form the basis of what dosage range to implement. Examples of factors that influence dosage amount include, but are not limited to, the size of the subject, how virulent the FMD strain that is being inoculated against is, and so forth. The FMD DNA vaccine and/or the method of vaccinating a mammalian subject with the vaccine protects the subject against one or more of the O, A, C, Asia 1, SAT 1, SAT 2 and SAT 3 serotypes of the FMD virus.

The FMD DNA vaccines formulated with compositions and methods described herein may be used prophylactically (e.g., to prevent or ameliorate the effects of a future infection), therapeutically (e.g., to treat or to empower the immune system of an infected organism) or both.

FMD vaccines in accordance with the present disclosure are marker vaccines or DIVA (Differentiating Infected from Vaccinated Animals), which induce immune responses that differ from those caused by natural infection. These differences are reflected in antibody profiles, and can be detected by diagnostic tests and assays such as enzyme linked immunosorbent assays (ELISAs) containing the same compositions used in the vaccine formulations. The DIVA strategy is useful in eradication scenarios wherein emergency vaccination using DIVA FMD vaccines could be an effective control tool for FMD outbreaks in densely populated livestock areas. DIVA vaccination can limit the number of culled animals in the process of FMD eradication, thereby enhancing public acceptance for disease control measures and limiting economic losses.

The minicircle vector DNA vaccine platform for FMD, as described herein, may be used with or without adjuvants. In certain embodiments, the FMD DNA vaccines further include one or more compounds selected from an adjuvant, a diluent or a carrier. Example adjuvants include, but are not limited to, aqueous-based aluminum hydroxide gel-saponin, the oil-based Montanide ISA 206, other aluminum-based adjuvants and incomplete Freunds adjuvant (IFA). Example diluents include, but are not limited to, water, physiological saline solution, human serum albumin, oils, polyethylene glycols, glycerin, propylene glycol or other synthetic solvents, antibacterial agents such as benzyl alcohol, antioxidants such as ascorbic acid or sodium bisulfite, chelating agents, such as ethylene diamine-tetra-acetic acid, buffers such as acetates, citrates or phosphates and agents for adjusting osmolarity, such as sodium chloride or dextrose.

Example carriers include, but are not limited to, liquid carriers (e.g., water, saline, culture medium, saline, aqueous dextrose, aqueous glycols) and solid carriers (e.g., carbohydrates such as starch, glucose, lactose, sucrose, dextrans; anti-oxidants such as ascorbic acid and glutathione, hydrolyzed proteins).

An FMD DNA vaccine's efficacy in embodiments is considered the rate of reduction in the incidence of serotype-specific FMD among a population of subjects that have been vaccinated compared to the incidence in a population of unvaccinated subjects, over a duration of 12 months. Vaccine efficacy (VE) can measured using the following formula:

$$VE=[(ARU-ARV)/ARU]\times 100\%$$

where "VE" is vaccine efficacy, "ARU" is an attack rate in an unvaccinated population and "ARV" is an attack rate in the vaccinated population.

FMD DNA vaccines comprising the minicircle DNA vector in accordance with the present disclosure exhibit VE values of between 50-95%, approximately 50%, greater than 50%, 50%, approximately 75%, approximately 75%, greater than 75%, approximately 90%, greater than 90%, 95%, approximately 95%, or greater than 95%.

The examples below are intended to further illustrate protocols for preparing and characterizing the transgene expression cassette and the minicircle vector carrying the transgene expression cassette, and are not intended to limit the scope of the claims. While these examples are provided for explanatory purposes, these should not be considered the only examples. Additional examples will be apparent based on the teachings of the present disclosure.

Example 1

Construction of Inserts and Production of Minicircle Vectors

Figure 4:
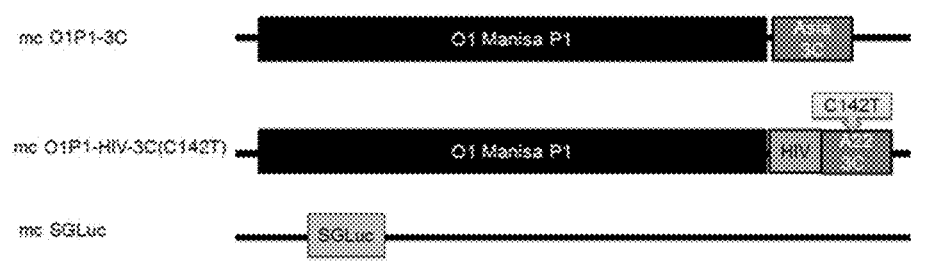

Three insert constructs, as may be seen in FIG. 4 and outlined below, were constructed, individually cloned and evaluated in a minicircle vector system in accordance with this disclosure.

The O1P1-3C(wt) insert (SEQ ID NO: 18) includes the mutant FMDV P1 polypeptide from FMDV O1 Manisa isolate 87 (SEQ ID NO: 1) with a wild-type Asia Lebanon 89 3C protease sequence for processing (SEQ ID NO: 7). This arrangement mirrors that used in FMDV adenovirus vaccine constructs. Examples include Mayr et al., *Immune Responses And Protection Against Foot-And-Mouth Disease Virus (FMDV) Challenge in Swine Vaccinated With Adenovirus-FMDV Constructs*, Vaccine, 2001 19:2152-62; Moraes et al., *Early Protection Against Homologous Challenge After a Single Dose of Replication-Defective Human Adenovirus Type 5 Expressing Capsid Proteins of Foot-And-Mouth Disease Virus (FMDV) Strain A24*, Vaccine, 2002 20:1631-9; Pacheco et al., *Rapid Protection of Cattle From Direct Challenge With Foot-And-Mouth Disease Virus (FMDV) by a Single Inoculation With An Adenovirus-Vectored FMDV Subunit Vaccine*, Virology, 2005 337:205-9. All of the foregoing articles are incorporated by reference in their entirety.

The O1P1-HIV-3C(C142T) insert (SEQ ID NO: 19) utilizes the mutant FMDV P1 polypeptide from FMDV O1 Manisa isolate 87 (SEQ ID NO: 1), the HIV frameshift element (SEQ ID NO: 6) with an A22 Iraq strain 3C protease containing a C142T mutation (SEQ ID NO: 9).

The wild-type nucleotide sequence of FMDV O1 Manisa isolate 87 P1 coding region comprises SEQ ID NO: 11.

The SGLuc insert (SEQ ID NO: 20) expresses the 8990 variant of *Gaussia* luciferase (SGLuc), such as that described in Kim et al., *Superluminescent Variants of Marine Luciferases for Bioassays*, Analytical Chemistry. 2011 83:8732-40, which is hereby incorporated herein by reference in its entirety. The SGLuc insert provides both a negative control for FMDV protein expression and a positive control for transfection efficiency due to its luciferase activities.

The Kozak eukaryotic translation initiation nucleotide sequence (SEQ ID NO: 5) is positioned 5' to each of the O1P1-3C(wt) (SEQ ID NO: 18), O1P1-HIV-3C(C142T) (SEQ ID NO: 19) and SGLuc insert constructs (SEQ ID NO: 20). With the O1P1-3C(wt) and O1P1-HIV-3C(C142T) inserts, the Kozak eukaryotic translation initiation nucleotide sequence is positioned 5' to mutant nucleotide sequence of FMDV P1 polypeptide from FMDV O1 Manisa isolate 87 (SEQ ID NO: 1).

To produce the pMC-CMV-SV40-polyA O1P1-HIV-3C(C142T) minicircle vector, the parental plasmid pMC-CMV-MCS-SV40-polyA (System Biosciences, catalog number MN501A-1) was digested with BamHI and EcoRI restriction enzymes according to manufacturer's instructions. The nucleotide sequence for the O1P1-HIV-3C(C142T) construct was synthesized and digested with BamHI and EcoRI restriction enzymes according to manufacturer's instructions for insertion into the pMC.CMV-MCS-SV40-polyA parental plasmid. A ligation reaction was performed using T4 DNA Ligase with a 3:1 insert to vector ratio as per manufacturer's instructions.

A ligation reaction was used to transform 5-alpha Competent *E. coli* (High Efficiency) as per manufacturer's instructions. The cells were plated on 50 µg/mL Kanamycin LB agar plates. Colonies were picked and grown in growth medium with kanamycin, overnight in a 37° C. shaker. Plasmids were purified using a miniprep kit according to manufacturer's protocols. Sequencing was performed to confirm mutation free insertion using the following primers: O1MSeq1-F (SEQ ID NO: 21), O1MSeq2-F (SEQ ID NO: 22), O1MSeq3-F (SEQ ID NO: 23), O1MSeq4-F (SEQ ID NO: 24), O1MSeq5-F (SEQ ID NO: 25), O1MSeq6-F (SEQ ID NO: 26), O1MSeq7-F (SEQ ID NO: 27), O1MSeq8-F (SEQ ID NO: 28), O1P1-Seq-R1 (SEQ ID NO: 29) and O1P1-Seq-R2 (SEQ ID NO: 30).

Alternatively, competent *E. coli* cells from the ZYCY10P3S2T *E. coli* strain were transformed by adding DNA from the ligation reaction to the competent cells that have been thawed on ice, incubating the cells on ice for 30 minutes min), heat-shocking the cells for 30 s in a 42° C. water bath without shaking and placing; the cells on ice again for 2 min. The transformed *E. coli* cells were recovered by adding 0.2 ml of room temperature Super Optimal Broth with Catabolit repression (SOC) medium to the cells and incubating at 30° C. or 37° C. for 60-90 min with shaking at 250 revolutions per minute (rpm). After that, the transformants were selected on LB plates containing 50 µg/µl kanamycin and 10 mM L-arabinose. Transformants that formed colonies after the overnight incubation had their minicircle vectors extracted by standard miniprep. The extracted minicircle vector samples were examined by restriction digest analysis and sequencing with the aforementioned primers.

The ZYCY10P3S2T *E. coli* strain harbors an arabinose-inducible system to express the PhiC31 integrase and I-SceI endonuclease (both integrase and endonuclease genes are found on the parental plasmid). The PhiC31 integrase excises the prokaryotic parts from the parental plasmid, thus forming a "bacterial backbone" and the pMC-CMV-SV40-polyA O1P1-HIV-3C(C142T) minicircle vector containing the transgene expression cassette. In one or more embodiments, the nucleotide sequence of the "bacterial backbone" and the pMC-CMV-SV40-polyA O1P1-HIV-3C(C142T) minicircle vector containing the transgene expression cassette comprises SEQ ID NO: 31. The bacterial backbone, containing signals for methylation transgene silencing, is recognized and ultimately degraded by the expressed I-SceI endonuclease. The elements that remain in the polyA O1P1-HIV-3C(C142T) minicircle vector include the Cytomegalovirus (CMV) promoter to drive high and sustained levels of gene expression and the Simian virus 40 (SV40) PolyA signal for transcription termination. In one or more embodiments, the pMC-CMV-SV40-polyA O1P1-HIV-3C(C142T) minicircle vector containing the transgene expression cassette comprises SEQ ID NO: 3.

To create the O1P1-3C(wt) construct the previously constructed O1P1-HIV-3C(C142T) construct was digested with NotI and EcoRI restriction enzymes according to manufacturer's instructions. PCR was performed according to manufacturer's instructions with primers Nod-3CLeb89-F (SEQ ID NO: and 3CLeb89-EcoRI-R (SEQ ID NO: 33) using a template plasmid containing the 3C nucleotide sequence from FMDV Asia Lebanon 1989 strain. PCR product was digested with NotI, and EcoRI restriction enzymes according to manufacturer's instructions. Ligation, transformation, plasmid purification, and sequencing were performed as described above. In one or more embodiments, the nucleotide sequence of the "bacterial backbone" and the pMC-CMV-SV40-polyA O1P1-3C(wt) minicircle vector containing the transgene expression cassette comprises SEQ. ID NO: 34. In one or more embodiments, the pMC-CMV-SV40-polyA O1P1-3C(wt) minicircle vector containing the transgene expression cassette comprises SEQ ID NO: 35.

To create the SGLuc construct a pTarget construct containing the SGLuc nucleotide coding sequence was digested with BamHI and EcoRI restriction enzymes according to manufacturer's instructions. Ligation, transformation, and plasmid purification was performed as described above. Sequencing was performed using primers AscI-Kzk-Gluc-F (SEQ ID NO: 36) and Gluc-R-NotI (SEQ ID NO: 37). In one or more embodiments, the "bacterial backbone" and the pMC-CMV-SV40-polyA SGLuc minicircle vector containing the transgene expression cassette comprises SEQ ID NO: 38. In one or more embodiments, the pMC-CMV-SV40-polyA SGLuc minicircle vector containing the transgene expression cassette comprises SEQ ID NO: 39.

Example 2

Transfection of the Minicircle Vectors into Mammalian Cells and VLP Production

The pMC-CMV-SV40-polyA O1P1-3C(wt) (SEQ ID NO: 35), pMC-CMV-SV40-polyA O1P1-HIV-3C(C142T) (SEQ ID NO: 3) and pMC-CMV-SV40-polyA SGLuc (SEQ ID NO: 39) minicircle vectors produced in Example 1 were transfected into the mammalian cell line LF-BK αV/β6 using a commercially available transfection reagent. LF-BK αV/β6 cells were cultivated in six well plates until 9:5% confluent. Transfections were performed with 4 μg of minicircle DNA according to the manufacturer's protocol. Additionally, HEK293-T cells at passage 71 at roughly 90% confluence were transfected with the minicircle vectors using a transfection reagent and 4 μg of the minicircle vectors as per manufacturer's instructions. Transfected cell cultures were allowed to sit at 37° C. for 24 hour (h) in a $CO_2$ incubator.

Example 3

Evaluation of Expression by Luciferase Assay

To evaluate expression of the pMC-CMV-SV40-polyA SGLuc minicircle vector, a luciferase assay was utilized to detect for luminescence. A luminescence assay was performed on a 96-well luminometer using 20 μl of harvested media without delay after injection of 25 μl of 100 μM water soluble coelenterazine solution and an integration of 0.5 s. Readings were taken both before and after injection of coelenterazine. During analysis of the data, readings for before injection were used to establish a baseline of light emission at the time of injection and were subsequently subtracted from post-injection values. Replicates were averaged together to give an overall luciferase reading in relative luciferase units per half second (RLU/0.5 s).

Figure 5:
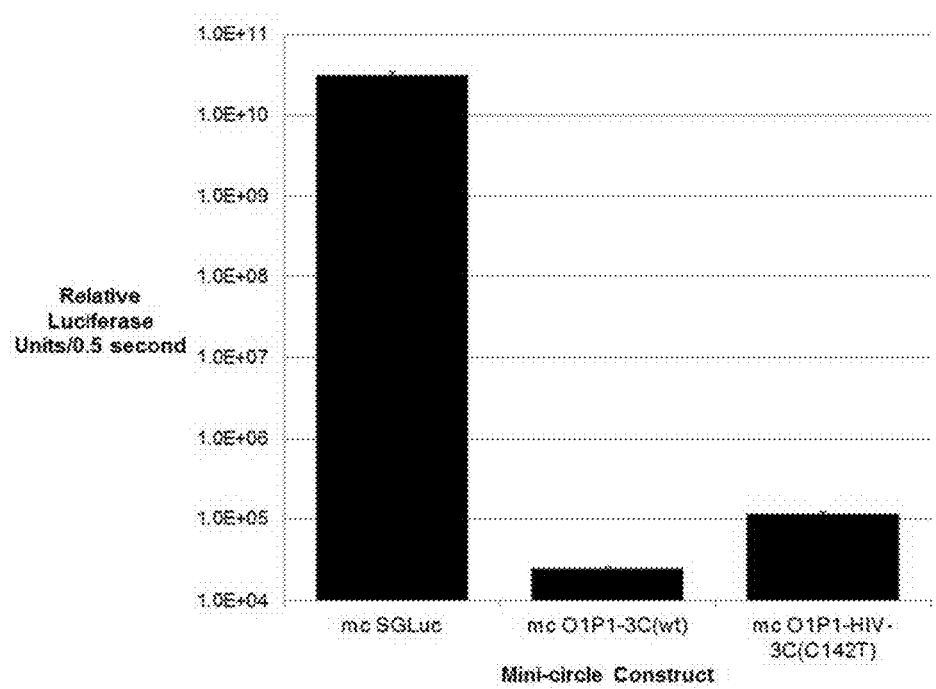
FIG. 5 is a bar graph of luciferase reading from cell culture media harvested off of transfected HEK239-T cells. The Y axis represents Relative Luciferase Units (RLU)/0.5 second (s), and the X axis represents the mc SGLuc, mc O1P1-3C(wt) and mc O1P1-HIV-3C(C142T) Mini-circle Constructs.

Media from transfected HEK293-T cells was harvested and checked for luciferase activity to confirm transfection, as shown in FIG. 5. As expected only cells transfected with the SGLuc insert construct showed luciferase activity.

Example 4

Evaluation of Expression and P1 Processing by Western Blotting

Transfected HEK293-T cells lysates was examined by western blotting to confirm expression and processing of FMDV proteins as shown in FIG. 6. Three different antibodies were used to examine processing. Each of the antibodies was chosen to react with a different capsid protein. Two mouse monoclonal antibodies, F14 and 12FE9, and one rabbit polyclonal antibody against FMDV VP3 were used. The F14 mouse monoclonal antibody reacts with the FMDV VP2 protein while the 12FE9 mouse monoclonal antibody reacts with VP1.

To evaluate processing, transfected cell lysates were harvested from 6 well plates using 250 μl of mammalian protein extraction reagent. Samples were mixed with a loading buffer to make a final concentration of 1×. 16 μl of the mixed samples were loaded onto 4-12% Bis-Tris protein gels and run according to manufacturer's instructions. Transfer of the protein gel to membranes was performed using a western blot.

Membranes were incubated in 5% milk blocking buffer solution for 1 h while shaking at room temperature. Membranes were rinsed two times with 1×PBS-T and washed for five min with 1×PBS-T while shaking at room temperature. Primary antibodies were diluted in 1×-PBS-T and applied to membranes for 1 h at room temperature. Primary antibodies used were 1:50 mouse monoclonal F14 (anti-VP2), 1:250 rabbit polyclonal anti-VP3, and 1:50 mouse monoclonal 12FE9 (anti-VP1). After incubation membranes were washed for five min with PBS-T for three times. Secondary antibodies were diluted in 1×PBS-T and applied to the membranes for 1 h at room temperature. Secondary antibodies used are a 1:500 dilution ratio of goat HRP conjugated anti-mouse (KPL) and a 1:500 dilution ratio of goat HRP conjugated anti-rabbit. After incubation membranes were washed for five min with PBS-T for three times. A solution of 3',3'-Diaminobenzidine made using 3,3'-Diaminobenzidine tablets was applied to membranes and incubated while shaking at room temperature until the appearance of bands.

As shown in FIG. 6, examination of cell lysates from cells transfected with the O1P1-3C(wt) construct shows full processing of all 3C dependent junctions. VP0 is present in O1P1-3C(wt) cell lysate. However the band is less intense than that of the VP2 band suggesting that there is a greater concentration of fully processed VP2 than unprocessed VP0 in the sample. Still referring to FIG. 6, the O1P1-HIV-3C (C142T) insert construct does not show complete processing of VPs as confirmed through the presence of detectable levels of unprocessed intermediates. The only unprocessed intermediate not observed is a 1ABCD fusion which would be hard to differentiate from the P1 polypeptide on the blots due to high and similar molecular weights. Additionally we see a more intense band representing VP0 than representing VP2 suggesting that there is more unprocessed VP0 in the sample than that of VP2, an inversion of what is observed with the O1P1-3C(wt) construct.

Given that the HIV-1 frameshift sequence reduces overall expression of 3C in the O1P1-HIV-3C(C142T) construct the presence of unprocessed intermediates is not surprising. The reduction of 3C expression lowers the level of 3C present which can process host proteins providing a benefit to the host cell. However it also reduces the amount of 3C available to process the FMDV VPs.

Example 5

Evaluation of Transfected Cells by Immunofluorescent Antibody Staining (IFA) and Transmission Electron Microscopy (TEM)

As the presence of processed P1 does not ensure the formation of VLPs, transfected LF-BK αV/β6 cells were examined at 24 and 48 h post-transfection using IFA staining and TEM to confirm the production of FMDV VLPs. An electron microscopy image showing FMDV VLPs in crystalline array is shown in FIG. 7.

HEK293-T cells were incubated to adhesion on a collagen coated slide, dried, then fixed at −20° C. with 1:1 acetone:methanol. Samples were blocked with 10% FBS in PBS. Antibody 12FE9 was used at a 1:10 dilution for primary staining. Secondary staining used 1:250 anti-mouse secondary antibody. Mounting media with DAPI (Molecular Probes P36935) was applied.

HEK293-T cells were grown in T-75 flasks for transmission electron microscopy (TEM). Cells were fixed in 2% glutaraldehyde in NaHCa (Heuser's) buffer, post-fixed with 1% tannic acid followed by 1% osmium tetroxide, en-bloc stained with 4% uranyl acetate, embedded in 2% agarose, dehydrated through graded series of acetone, and embedded in Spurr's resin. Ultrathin (80 nm) sections were cut on a ultramicrotome (e.g., Leica UC6), stained with uranyl acetate and lead citrate, and imaged on a transmission electron microscope (e.g. Hitachi 7600) with a 2 k×2 k AMT camera at 80 kV.

Figure 7:
FIG. 7 is a transmission electron microscopy image showing formation of FMDV VLP arrays of HEK293-T cells transfected with pMC-CMV-SV40-polyA O1P1-3C (wt) minicircles.
Figure 8A:
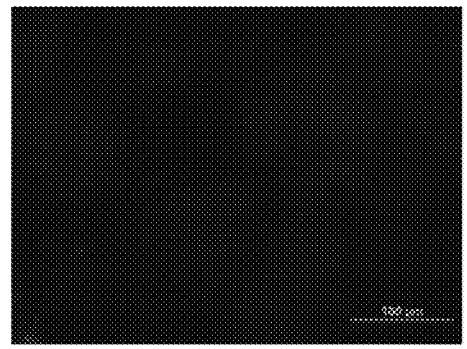
FIG. 8A is an image of IFA staining of HEK293-T cells transfected with pMC-CMV-SV40-polyA SGLuc minicircles using 12FE9 antibody.

Similarly, to confirm the presence of VLPs generated off of minicircles, transfected HEK293-T cells were examined using TEM (see FIG. 7). IFAs were performed on transfected cells to ensure the presence of expressed proteins in transfected cell lines (see FIGS. 8A-8C). The IFAs showed expression of FMDV proteins in both constructs that contained the FMDV P1 polypeptide (FIGS. 8B and 8C) and no expression in cells transfected with the mc SGLuc construct (FIG. 8A). This is in agreement with results seen in previously performed western blots in FIG. 6.

Fluorescence in the pMC-CMV-SV40-polyA O1P1-3C (wt) samples was localized largely in aggregates while fluorescence in pMC-CMV-S0-polyA O1P1-HIV-3C (C142T) samples was much more diffused through the whole cell. This suggests that transgene expression in O1P1-3C(wt) transfected samples is more structured and localized.

Figure 8B:
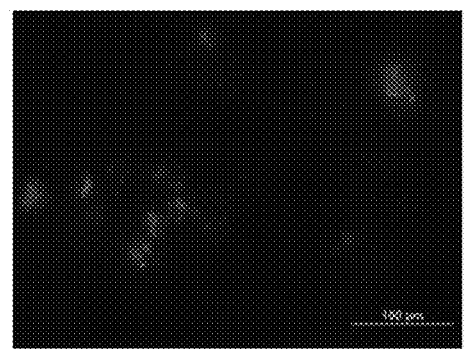
FIG. 8B is an image of IFA staining of HEK293-T cells transfected with pMC-CMV-SV40-polyA O1P1-3C(wt) minicircles using 12FE9 antibody.
Figure 8C:
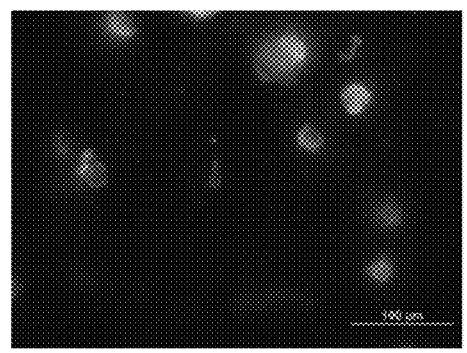
FIG. 8C is an image of IFA staining of HEK293-T cells transfected with pMC-CMV-SV40-polyA O1P1-HIV-3C (C142T) minicircles using 12FE9 antibody.

In FIG. 7, the transmission electron microscopy image shows formation of FMDV VLP arrays of HEK293-T cells transfected with pMC-CMV-SV40-polyA O1P1-3C(wt). This aligns with the difference in fluorescence distribution between pMC-CMV-SV40-polyA O1P1-3C(wt) and pMC-CMV-SV40-polyA O1P1-HIV-3C(C142T) samples as seen in FIGS. 8B and 8C, respectively. This difference in distribution is also probably related to the lack of complete processing observed in pMC-CMV-SV40-polyA O1P1-HIV-3C(C142T) samples in FIG. 6. The observance of VLP arrays in the pMC-CMV-S0-polyA O1P1-3C(wt) sample does confirm that VLP formation using a minicircle vector is viable. Previous publications using the HIV frameshift in conjunction with the FMDV 3C, (Porta C, Xu X, Loureiro S, Paramasivam S, Ren J, Al-Khalil T, et al. *Efficient production of foot-and-mouth disease virus empty capsids in insect cells following down regulation of 3C protease activity*. Journal of Virological Methods. 2013 187:406-12, incorporated herein by reference in its entirety), observed VLPs after utilizing sucrose gradient purification to concentrate any VLPs produced prior to observation with TEM. It is possible that this additional purification and subsequent concentration of the samples aids in VLP detection by TEM.

The foregoing discussion discloses embodiments in accordance with the present disclosure. As will be understood by those skilled in the art, the approaches, methods, techniques, materials, devices, and so forth disclosed herein may be embodied in additional embodiments as understood by those of skill in the art, it is the intention of this application to encompass and include such variation. Accordingly, this disclosure is illustrative and should not be taken as limiting the scope of the following claims.

What is claimed:

1. A mutant nucleotide sequence that encodes a foot-and-mouth disease virus (FMDV) capsid polyprotein precursor, wherein the mutant nucleotide sequence comprises one or more silent mutations to a nucleotide sequence encoding a wild-type FMDV capsid polyprotein precursor that removes one or more restriction enzyme recognition sites, wherein all occurrences of said one or more restriction enzyme recognition sites are removed from the nucleotide sequence.

2. The mutant nucleotide sequence of claim 1, wherein the mutant nucleotide sequence comprises at least one of one through twenty-two (1-22) silent mutations, one through fifteen (1-15) silent mutations, or one through ten (1-10) silent mutations that remove one or more restriction enzyme recognition sites.

3. The mutant nucleotide sequence of claim 2, wherein said one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1518, C1578, T1593, C1665, C1836, C2010, A2190, and combinations thereof.

4. The mutant nucleotide sequence of claim 2, wherein said one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1518C, C1578A, T1593A, C1665G, C1836G, C2010T, A2190T, and combinations thereof.

5. The mutant nucleotide sequence of claim 1, wherein the one or more restriction enzyme recognition site is selected from the group consisting of XbaI, XcmI, BsiWI, XhoI, BstEII, PflMI, AccI, NheI, SacII, PpuMI, AgeI, PvuII, NcoI, PstI, BstXI, AatII, XmnI, and combinations thereof.

6. The mutant nucleotide sequence of claim 1, wherein the FMDV is selected from the group consisting of O, A, C, Asia 1, SAT 1, SAT 2, and SAT 3 serotypes.

7. The mutant nucleotide sequence of claim 1, comprising SEQ ID NO: 1.

8. The mutant nucleotide sequence of claim 1, wherein the nucleotide sequence encoding the wild-type FMDV capsid polyprotein precursor is selected from the group consisting of SEQ ID NO: 11-17.

9. A vector comprising a mutant nucleotide sequence that encodes a foot-and-mouth disease virus (FMDV) capsid polyprotein precursor, wherein the mutant nucleotide sequence comprises one or more silent mutations to a nucleotide sequence encoding a wild-type FMDV capsid polyprotein precursor that removes one or more restriction enzyme recognition sites, wherein all occurrences of said one or more restriction enzyme recognition sites are removed from the nucleotide sequence.

10. The vector of claim 9, wherein the mutant nucleotide sequence comprises at least one of one through twenty-two (1-22) silent mutations, one through fifteen (1-15) silent mutations, or one through ten (1-10) silent mutations that remove one or more restriction enzyme recognition sites.

11. The vector of claim 10, wherein said one of one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1518, C1578, T1593, C1665, C1836, C2010, A2190, and combinations thereof.

12. The vector of claim 10, wherein said one of one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1518C, C1578A, T1593A, C1665G, C1836G, C2010T, A2190T, and combinations thereof.

13. The vector of claim 9, further comprising:
a eukaryotic translation initiation nucleotide sequence positioned 5' to the mutant nucleotide sequence;
a nucleotide sequence that encodes a protease; and
a translational regulatory element positioned 3' to the mutant nucleotide sequence and 5' to the nucleotide sequence that encodes the protease.

14. The vector of claim 13, wherein the translational regulatory element is functional to reduce expression of the protease.

15. The vector of claim 13, wherein the vector comprises a mini circle vector.

16. The vector of claim 13, wherein the protease is functionally able to cleave the FMDV capsid polyprotein precursor into a plurality of FMDV capsid proteins.

17. The vector of claim 16, wherein the FMDV capsid proteins are selected from the group consisting of VP1, VP2, VP3, VP4, and combinations thereof.

18. The vector of claim 16, wherein the vector expresses the protease, when transformed in to a host cell.

19. The vector of claim 13, wherein the eukaryotic translation initiation nucleotide sequence comprises the nucleotide sequence of SEQ ID NO: 4.

20. The vector of claim 13, wherein the eukaryotic translation initiation nucleotide sequence comprises the nucleotide sequence of SEQ ID NO: 5.

21. The vector of claim 13, wherein the translational regulatory element comprises a DNA or RNA sequence responsible for a ribosomal frameshift.

22. The vector of claim 21, wherein the DNA or RNA sequence responsible for a ribosomal frameshift is selected from the group consisting of an ALIL pseudoknot, an antizyme RNA frameshifting stimulation element, a coronavirus frameshifting stimulation element, a DnaX ribosomal frameshifting element, a HIV ribosomal frameshift signal, an insertion sequence IS1222 ribosomal frameshifting element, and a ribosomal frameshift.

23. The vector of claim 21, wherein the DNA or RNA sequence responsible for a ribosomal frameshift is functional to mediate a translational frameshift in the protease in an amount of 90-95% of translated protease mRNA.

24. The vector of claim 21, wherein the DNA or RNA sequence responsible for a ribosomal frameshift is functional to yield translation of no more than twenty percent (20%) of the nucleotide sequence that encodes the protease after translation.

25. The vector of claim 21, wherein the DNA or RNA sequence responsible for a ribosomal frameshift is functional to yield translation of between five and ten percent (5-10%) of the nucleotide sequence that encodes the protease after translation.

26. The vector of claim 21, wherein the nucleotide sequence that encodes the protease is fully translated and comprises a correct translation of the protease after translation.

27. The vector of claim 13, wherein the protease comprises the amino acid sequence of SEQ ID NO: 8.

28. The vector of claim 13, wherein the nucleotide sequence that encodes the protease comprises SEQ ID NO: 7.

29. The vector of claim 13, comprising the nucleotide sequence of SEQ ID NO: 1 and of SEQ ID NO: 7.

30. The vector of claim 13, wherein the nucleotide sequence that encodes the protease comprises SEQ ID NO: 9.

31. The vector of claim 13, comprising the nucleotide sequence of SEQ ID NO: 1 and of SEQ ID NO: 9.

32. A transformed host cell comprising a mutant nucleotide sequence that encodes a foot-and-mouth disease virus (FMDV) capsid polyprotein precursor, wherein the mutant nucleotide sequence comprises one or more silent mutations to a nucleotide sequence encoding a wild-type FMDV capsid polyprotein precursor that removes one or more restriction enzyme recognition sites, wherein all occurrences of said one or more restriction enzyme recognition sites are removed from the nucleotide sequence.

33. The host cell of claim 32, wherein the mutant nucleotide sequence comprises at least one of one through twenty-two (1-22) silent mutations, one through fifteen (1-15) silent mutations, or one through ten (1-10) silent mutations that remove one or more restriction enzyme recognition sites.

34. The host cell of claim 33, wherein said one of one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1518, C1578, T1593, C1665, C1836, C2010, A2190, and combinations thereof.

35. The host cell of claim 33, wherein said one of one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1518C, C1578A, T1593A, C1665G, C1836G, C2010T, A2190T, and combinations thereof.

36. The transformed host cell of claim 32, wherein the transformed host cell is a mammalian cell.

37. The transformed host cell of claim 32, wherein the transformed host cell is functional to produce a virus like particle (VLP).

38. The transformed host cell of claim 32, wherein the VLP comprises a FMDV VLP.

39. A virus like particle (VLP) comprising a polypeptide produced from expression of a vector comprising a mutant nucleotide sequence that encodes a foot-and-mouth disease virus (FMDV) capsid polyprotein precursor, wherein the mutant nucleotide sequence comprises one or more silent mutations to a nucleotide sequence encoding a wild-type FMDV capsid polyprotein precursor that removes one or more restriction enzyme recognition sites, wherein all occurrences of said one or more restriction enzyme recognition sites are removed from the nucleotide sequence.

40. The VLP of claim 39, wherein the mutant nucleotide sequence comprises at least one of one through twenty-two (1-22) silent mutations, one through fifteen (1-15) silent mutations, or one through ten (1-10) silent mutations that remove one or more restriction enzyme recognition sites.

41. The VLP of claim 40, wherein said one of one through twenty-two (1-22) silent mutations, one through fifteen (1-15) silent mutations, or one through ten (1-10) silent mutations are selected from the group consisting of C99, C285, T345, G354, A369, C408, C468, G498, C528, A588, C597, C627, C957, G1170, T1518, C1578, T1593, C1665, C1836, C2010, A2190, and combinations thereof.

42. The VLP of claim 40, wherein said one of one through twenty-two (1-22) silent mutations, one through fifteen (1-15) silent mutations, or one through ten (1-10) silent mutations are selected from the group consisting of C99T, C285T, T345A, G354A, A369G, C408T, C468A, G498A, C528T, A588T, C597T, C627T, C957A, G1170C, T1518C, C1578A, T1593A, C1665G, C1836G, C2010T, A2190T, and combinations thereof.

43. The VLP of claim 39, wherein the vector further comprises:
 a eukaryotic translation initiation nucleotide sequence positioned 5' to the mutant nucleotide sequence;
 a nucleotide sequence that encodes a protease; and
 a translational regulatory element positioned 3' to the mutant nucleotide sequence and 5' to the nucleotide sequence that encodes the protease.

* * * * *

SEQUENCE LISTING

```
<160> NUMBER OF SEQ ID NOS: 39

<210> SEQ ID NO 1
<211> LENGTH: 2259
<212> TYPE: DNA
<213> ORGANISM: Artificial Sequence
<220> FEATURE:
<223> OTHER INFORMATION: P1 polyprotein precursor from FMDV O1 Manisa
      isolate 87, mutated

<400> SEQUENCE: 1
ggagccgggc aatccagccc ggcaaccggg tcacagaacc aatcaggcaa cactgggagc      60
atcatcaaca attactacat gcagcagtac caaaactcta tggacacaca acttggtgac     120
aacgctacaa gcggaggctc aaacgagggg tccacggaca caacctccac ccacacaacc     180
aacactcaga acaacgactg gttctcgaag ctggccagtt ccgctttcag cggtcttttc     240
ggcgctcttc tcgccgacaa gaaaaccgag gagaccactc ttcttgagga ccgcatcctc     300
actactcgta acggacacac cacctcgaca acccagtcga gcgtaggagt cacatacggg     360
tatgcaacgg ctgaggattt cgtgagcggg ccaaacacct ctggtcttga gaccagggtt     420
gcccaggcag agcggttctt taaaacccac ctgttcgact gggtcacaag tgacccgttc     480
ggacggtgcc acctgctaga acttccaact gaccacaaag gtgtctatgg cagcctgacc     540
gactcgtatg cttatatgag gaacggctgg gatgttgaag tcactgctgt gggaaatcag     600
ttcaatggag gatgcctgtt ggtggctatg gtgccagaac tttgctccat acagaagagg     660
gagctgtacc agctcacgct ctttcctcac cagttcatca accctcggac gaacatgaca     720
gcacacatca ctgtgccctt tgttggcgtc aaccgttatg accagtacaa ggtacacaaa     780
ccttggaccc tcgtggttat ggttgtagcc ccctgaccg tcaacagtga aggtgccccg     840
caaatcaagg tgtatgccaa catcgcacct accaacgtac acgtcgcggg tgagttccct     900
tccaaagagg ggatcttccc tgtggcttgc agcgatggtt atggcggtct ggtgacaact     960
gacccgaaaa cggctgaccc cgcttacggg aaagtgttta ccccccccg caacatgttg    1020 ccggggcggt tcaccaattt tcttgacgtg gctgaggcgt gccccacgtt tctccacttc    1080
gagggtgacg tgccatacgt gaccacgaag acggattcag acagggtgct cgctcagttc    1140
gacttgtctt tggcagcaaa gcacatgtcc aacaccttcc ttgcaggtct cgcccagtac    1200
```

| | |
|---|---|
| tacacacagt acagcggcac catcaacctg cacttcatgt tcacagggcc tactgacgcg | 1260 |
| aaggcgcgtt acatgattgc gtatgctcct cctggcatgg aaccacctaa aacgccagag | 1320 |
| gcggctgccc actgcatcca tgctgaatgg acacagggt tgaactcaaa attcacattt | 1380 |
| tcaatccctt acctttcggc ggctgattac gcttacacag cgtctgacac tgctgagacc | 1440 |
| acaaatgtac agggatgggt ttgcctgttt caaataacac acgggaaagc tgacggcgac | 1500 |
| gcactggtcg ttttggccag cgccggaaag gactttgagc tgcgcctgcc ggtggatgct | 1560 |
| cgcacacaga ctacctcagc gggcgagtca gcagaccccg tgaccgccac cgttgagaat | 1620 |
| tacggtggcg agacacaggt ccagaggcgc aacacacgg acgtgtcatt tatattagac | 1680 |
| agatttgtga aagtgacacc aaaagaccaa attaatgtat tggacctgat gcaaaccct | 1740 |
| gctcacactt tggtgggagc actccttcgt actgccactt actatttcgc tgacttagag | 1800 |
| gtggcagtga agcacgaggg aaacctcacc tgggtgccga acggggcgcc tgaagcggcg | 1860 |
| ttggacaaca ccaccaaccc aacagcttac acaaggcac cactcacccg acttgcactg | 1920 |
| ccttacacgg cgccacaccg cgtgttggct actgtttaca acgggaacag caagtatggt | 1980 |
| gacggcacgg tggccaatgt gagaggtgat ctgcaagtgt tggcccagaa ggcggcgaga | 2040 |
| gcgctgccta cctccttcaa ctacggtgcc attaaagcta ctcgggtgac tgaactgctt | 2100 |
| taccgcatga agagggctga gacatactgt ccccggcctc ttttggccat tcacccggac | 2160 |
| caggctagac acaagcagaa gattgtggct ccggtgaaac agcttctaaa ttttgacctg | 2220 |
| ctcaaattgg cgggagatgt ggagtccaac cctgggccc | 2259 |

<210> SEQ ID NO 2
<211> LENGTH: 3059
<212> TYPE: DNA
<213> ORGANISM: Artificial Sequence
<220> FEATURE:
<223> OTHER INFORMATION: Transgene expression cassette

<400> SEQUENCE: 2

| | |
|---|---|
| ggatccgccg ccgccatggg agccgggcaa tccagcccgg caaccgggtc acagaaccaa | 60 |
| tcaggcaaca ctgggagcat catcaacaat tactacatgc agcagtacca aaactctatg | 120 |
| gacacacaac ttggtgacaa cgctacaagc ggaggctcaa cgaggggtc cacggacaca | 180 |
| acctccaccc acacaaccaa cactcagaac aacgactggt tctcgaagct ggccagttcc | 240 |
| gctttcagcg gtcttttcgg cgctcttctc gccgacaaga aaaccgagga gaccactctt | 300 |
| cttgaggacc gcatcctcac tactcgtaac ggacacacca cctcgacaac ccagtcgagc | 360 |
| gtaggagtca catacgggta tgcaacggct gaggatttcg tgagcgggcc aaacacctct | 420 |
| ggtcttgaga ccagggttgc ccaggcagag cggttctttta aacccaccct gttcgactgg | 480 |
| gtcacaagtg acccgttcgg acggtgccac ctgctagaac ttccaactga ccacaaaggt | 540 |
| gtctatggca gcctgaccga ctcgtatgct tatatgagga acggctggga tgttgaagtc | 600 |
| actgctgtgg gaaatcagtt caatggagga tgcctgttgg tggctatggt gccagaactt | 660 |
| tgctccatac agaagaggga gctgtaccag ctcacgctct tcctcacca gttcatcaac | 720 |
| cctcggacga acatgacagc acacatcact gtgccctttg ttggcgtcaa ccgttatgac | 780 |
| cagtacaagg tacacaaacc ttggacccte gtggttatgg ttgtagcccc cctgaccgtc | 840 |
| aacagtgaag gtgccccgca aatcaaggtg tatgccaaca tcgcacctac caacgtacac | 900 |
| gtcgcgggtg agttcccttc caaagagggg atcttccctg tggcttgcag cgatggttat | 960 |

```
ggcggtctgg tgacaactga cccgaaaacg gctgaccccg cttacgggaa agtgtttaac    1020
cccccccgca acatgttgcc ggggcggttc accaattttc ttgacgtggc tgaggcgtgc    1080
cccacgtttc tccacttcga gggtgacgtg ccatacgtga ccacgaagac ggattcagac    1140
agggtgctcg ctcagttcga cttgtctttg gcagcaaagc acatgtccaa caccttcctt    1200
gcaggtctcg cccagtacta cacacagtac agcggcacca tcaacctgca cttcatgttc    1260
acagggccta ctgacgcgaa ggcgcgttac atgattgcgt atgctcctcc tggcatggaa    1320
ccacctaaaa cgccagaggc ggctgcccac tgcatccatg ctgaatggga cacagggttg    1380
aactcaaaat tcacattttc aatcccttac ctttcggcgg ctgattacgc ttacacagcg    1440
tctgacactg ctgagaccac aaatgtacag ggatgggttt gcctgtttca ataacacac     1500 gggaaagctg acggcgacgc actggtcgtt ttggccagcg ccggaaagga ctttgagctg    1560
cgcctgccgg tggatgctcg cacacagact acctcagcgg gcgagtcagc agaccccgtg    1620
accgccaccg ttgagaatta cggtggcgag acacaggtcc agaggcgcca acacacggac    1680
gtgtcattta tattagacag atttgtgaaa gtgacaccaa aagaccaaat taatgtattg    1740
gacctgatgc aaaccctgc tcacactttg gtgggagcac tccttcgtac tgccacttac     1800
tatttcgctc acttagaggt ggcagtgaag cacgagggaa acctcacctg ggtgccgaac    1860
ggggcgcctg aagcggcgtt ggacaacacc accaacccaa cagcttacca aaggcacca    1920 ctcacccgac ttgcactgcc ttacacgcgc ccacaccgcg tgttggctac tgtttacaac    1980
gggaacagca gtatggtga cggcacggtg gccaatgtga gaggtgatct gcaagtgttg     2040
gcccagaagg cggcgagagc gctgcctacc tccttcaact acggtgccat taaagctact    2100
cgggtgactg aactgcttta ccgcatgaag agggctgaga catactgtcc ccggcctctt    2160
ttggccattc acccggacca ggctagacac aagcagaaga ttgtggctcc ggtgaaacag    2220
cttctaaatt ttgacctgct caaattggcg ggagatgtgg agtccaaccc tgggcccagc    2280
ggccgcggac ttttttagg gaagatctgg ccttcctaca agggaaggcc agggaatttt    2340
cttacgaggg accggtaaaa aaacccgtag cactcaaggt taaagcaaag aatctcattg    2400
ttaccgaaag tggagccca ccgaccgact tgcaaaagat ggtcatgggc aacaccaagc     2460
ctgttgaact catcctcgac gggaagacgg tggccatttg ttgtgctacc ggtgtgtttg    2520
gcactgcgta cctcgtgcct cgtcatcttt ttgcagaaaa atatgacaag atcatgctgg    2580
acggcagagc catgacagac agtgactaca gagtgtttga gtttgagatt aaagtaaaag    2640
gacaggacat gctctcagac gctgcgctca tggtactcca ccgtgggaat cgcgtgagag    2700
acatcacgaa acactttcgt gacacagcaa gaatgaagaa aggcaccct gttgtcggag     2760 taatcaacaa tgccgacgtc gggagactga tcttctctgg tgaggccctt acctacaagg    2820
acattgtagt gacaatggat ggagacacca tgcctggcct gtttgcctac aaagccgcca    2880
ccaaggctgg ctactgtggg ggagccgttc ttgctaagga cggagctgac acattcatcg    2940
ttggcactca ctccgcaggc ggcaatggag ttggatactg ctcatgcgtt tccaggtcca    3000
tgttgctgaa aatgaaggcg cacatcgacc ccgaaccaca ccacgagaag taagaattc     3059
```

<210> SEQ ID NO 3
<211> LENGTH: 4788
<212> TYPE: DNA
<213> ORGANISM: Artificial Sequence
<220> FEATURE:
<223> OTHER INFORMATION: pMC-CMV-SV40-polyA O1P1-HIV-3C(C142T)(without bacterial backbone)

```
<400> SEQUENCE: 3
cccttgggct cccccgggcgc gactagtgaa ttgatactag tattatgccc agtacatgac      60
cttatgggac tttcctactt ggcagtacat ctacgtatta gtcatcgcta ttaccatggt     120
gatgcggttt tggcagtaca tcaatgggcg tggatagcgg tttgactcac ggggatttcc     180
aagtctccac cccattgacg tcaatgggag tttgttttgg caccaaaatc aacgggactt     240
tccaaaatgt cgtaacaact ccgccccatt gacgcaaatg ggcggtaggc gtgtacggtg     300
ggaggtttat ataagcagag ctcgtttagt gaaccgtcag atcgcctgga gacgccatcc     360
acgctgtttt gacctccata gaagattcta gagtcgacgc ggccgcggat ccgccgccgc     420
catgggagcc gggcaatcca gcccggcaac cgggtcacag aaccaatcag gcaacactgg     480
gagcatcatc aacaattact acatgcagca gtaccaaaac tctatggaca cacaacttgg     540
tgacaacgct acaagcggag gctcaaacga ggggtccacg gacacaacct ccacccacac     600
aaccaacact cagaacaacg actggttctc gaagctggcc agttccgctt tcagcggtct     660
tttcggcgct cttctcgccg acaagaaaac cgaggagacc actcttcttg aggaccgcat     720
cctcactact cgtaacggac acaccacctc gacaacccag tcgagcgtag gagtcacata     780
cgggtatgca acggctgagg atttcgtgag cgggccaaac acctctggtc ttgagaccag     840
ggttgcccag gcagagcggt tcttaaaaac ccacctgttc gactgggtca caagtgaccc     900
gttcggacgg tgccacctgc tagaacttcc aactgaccac aaaggtgtct atggcagcct     960
gaccgactcg tatgcttata tgaggaacgg ctgggatgtt gaagtcactg ctgtgggaaa    1020
tcagttcaat ggaggatgcc tgttggtggc tatggtgcca gaactttgct ccatacagaa    1080
gagggagctg taccagctca cgctctttcc tcaccagttc atcaaccctc ggacgaacat    1140
gacagcacac atcactgtgc cctttgttgg cgtcaaccgt tatgaccagt acaaggtaca    1200
caaaccttgg accctcgtgg ttatggttgt agccccctg accgtcaaca gtgaaggtgc    1260
cccgcaaatc aaggtgtatg ccaacatcgc acctaccaac gtacacgtcg cgggtgagtt    1320
cccttccaaa gaggggatct tccctgtggc ttgcagcgat ggttatggcg gtctggtgac    1380
aactgacccg aaaacggctg accccgctta cgggaaagtg tttaaccccc cccgcaacat    1440
gttgccgggg cggttcacca attttcttga cgtggctgag gcgtgcccca cgtttctcca    1500
cttcgagggt gacgtgccat acgtgaccac gaagacggat tcagacaggg tgctcgctca    1560
gttcgacttg tctttggcag caaagcacat gtccaacacc ttccttgcag gtctcgccca    1620
gtactacaca cagtacagcg gcaccatcaa cctgcacttc atgttcacag gcctactga    1680
cgcgaaggcg cgttacatga ttgcgtatgc tcctcctggc atggaaccac ctaaaacgcc    1740
agaggcggct gccccactgca tccatgctga atgggacaca gggttgaact caaaattcac    1800
attttcaatc ccttaccttt cggcggctga ttacgcttac acagcgtctg acactgctga    1860
gaccacaaat gtacagggat gggttttgcct gtttcaaata cacacgggaa agctgacgg    1920
cgacgcactg gtcgtttttgg ccagcgccgg aaaggacttt gagctgcgcc tgccggtgga    1980
tgctcgcaca cagactacct cagcgggcga gtcagcagac cccgtgaccg ccaccgttga    2040
gaattacggt ggcgagacac aggtccagag gcgccaacac acggacgtgt catttatatt    2100
agacagattt gtgaaagtga caccaaaaga ccaaattaat gtattggacc tgatgcaaac    2160
ccctgctcac actttggtgg gagcactcct tcgtactgcc acttactatt tcgctgactt    2220
agaggtggca gtgaagcacg agggaaacct cacctgggtg ccgaacgggg cgcctgaagc    2280
ggcgttggac aacaccacca acccaacagc ttaccacaag gcaccactca cccgacttgc    2340
```

```
actgccttac acggcgccac accgcgtgtt ggctactgtt tacaacggga acagcaagta    2400
tggtgacggc acggtggcca atgtgagagg tgatctgcaa gtgttggccc agaaggcggc    2460
gagagcgctg cctacctcct tcaactacgg tgccattaaa gctactcggg tgactgaact    2520
gctttaccgc atgaagaggg ctgagacata ctgtccccgg cctcttttgg ccattcaccc    2580
ggaccaggct agacacaagc agaagattgt ggctccggtg aaacagcttc taaattttga    2640
cctgctcaaa ttggcgggag atgtggagtc aacccctggg cccagcggcc gcggaccttt    2700
tttagggaag atctggcctt cctacaaggg aaggccaggg aattttctta cgagggaccg    2760
gtaaaaaaac ccgtagcact caaggttaaa gcaaagaatc tcattgttac cgaaagtgga    2820
gccccaccga ccgacttgca aaagatggtc atgggcaaca ccaagcctgt tgaactcatc    2880
ctcgacggga agacggtggc catttgttgt gctaccggtg tgtttggcac tgcgtacctc    2940
gtgcctcgtc atcttttgc agaaaaatat gacaagatca tgctggacgg cagagccatg    3000
acagacagtg actacagagt gtttgagttt gagattaaag taaaaggaca ggacatgctc    3060
tcagacgctg cgctcatggt actccaccgt gggaatcgcg tgagagacat cacgaaacac    3120
tttcgtgaca cagcaagaat gaagaaaggc accctgttg tcggagtaat caacaatgcc    3180
gacgtcggga gactgatctt ctctggtgag gcccttacct acaaggacat tgtagtgaca    3240
atggatggag acaccatgcc tggcctgttt gcctacaaag ccgccaccaa ggctggctac    3300
tgtgggggag ccgttcttgc taaggacgga gctgacacat tcatcgttgg cactcactcc    3360
gcaggcggca atggagttgg atactgctca tgcgtttcca ggtccatgtt gctgaaaatg    3420
aaggcgcaca tcgaccccga accacaccac gagaagtaag aattcgagct cgacaatcaa    3480
cctctggatt acaaaatttg tgaaagattg actggtattc ttaactatgt tgctcctttt    3540
acgctatgtg gatacgctgc tttaatgcct ttgtatcatg ctattgcttc ccgtatggct    3600
ttcattttct cctccttgta taaatcctgg ttgctgtctc tttatgagga ttgtggccc     3660
gttgtcaggc aacgtggcgt ggtgtgcact gtgtttgctg acgcaacccc cactggttgg    3720
ggcattgcca ccacctgtca gctccttttcc gggactttcg ctttccccct ccctattgcc    3780
acggcggaac tcatcgccgc ctgccttgcc cgctgctgga caggggctcg gctgttgggc    3840
actgacaatt ccgtggtgtt gtcggggaaa tcatcgtcct ttccttggct gctcgcctgt    3900
gttgccacct ggattctgcg cgggacgtcc ttctgctacg tcccttcggc cctcaatcca    3960
gcggaccttc cttcccgcgg cctgctgccg gctctgcggc ctcttccgcg tcttcgcctt    4020
cgccctcaga cgagtcggat ctccctttgg gccgcctccc cgcctggtac ctttaagacc    4080
aatgacttac aaggcagctg tagatcttag ccactttta aaagaaaagg ggggactgga    4140
agggctaatt cactcccaac gaagataaga tctgcttttt gcttgtactg ggtctctctg    4200
gttagaccag atctgagcct gggagctctc tggctaacta gggaacccac tgcttaagcc    4260
tcaataaagc ttgccttgag tgcttcaagt agtgtgtgcc cgtctgttgt gtgactctgg    4320
taactagaga tccctcagac cctttttagtc agtgtggaaa atctctagca gtagtagttc    4380
atgtcatctt attattcagt atttataact tgcaaagaaa tgaatatcag agagtgagag    4440
gaacttgttt attgcagctt ataatggtta caaataaagc aatagcatca caaatttcac    4500
aaataaagca ttttttttcac tgcattctag ttgtggtttg tccaaactca tcaatgtatc    4560
ttatcatgtc tggctctagc tatcccgccc ctaactccgc ccatcccgcc ctaactccg     4620
cccagttccg cccattctcc gccccatggc tgactaattt ttttttattta tgcagaggcc    4680
```

```
gaggccgcct cggcctctga gctattccag aagtagtgag gaggcttttt tggaggccta    4740
gacttttgca gatcgaccca tgggggcccg ccccaactgg ggtaacct                 4788
```

<210> SEQ ID NO 4
<211> LENGTH: 13
<212> TYPE: DNA
<213> ORGANISM: Artificial Sequence
<220> FEATURE:
<223> OTHER INFORMATION: Kozak consensus sequence
<220> FEATURE:
<221> NAME/KEY: misc_feature
<222> LOCATION: (7)..(7)
<223> OTHER INFORMATION: r is g or a

<400> SEQUENCE: 4

```
gccgccrcca tgg                                                        13
```

<210> SEQ ID NO 5
<211> LENGTH: 13
<212> TYPE: DNA
<213> ORGANISM: Artificial Sequence
<220> FEATURE:
<223> OTHER INFORMATION: Kozak eukaryotic translation initiation
      sequence

<400> SEQUENCE: 5

```
gccgccgcca tgg                                                        13
```

<210> SEQ ID NO 6
<211> LENGTH: 120
<212> TYPE: DNA
<213> ORGANISM: Human immunodeficiency virus
<220> FEATURE:
<221> NAME/KEY: misc_feature
<223> OTHER INFORMATION: Human immunodeficiency virus frameshift element

<400> SEQUENCE: 6

```
acctttttta gggaagatct ggccttccta caagggaagg ccagggaatt ttcttacgag      60
ggaccggtaa aaaacccgt agcactcaag gttaaagcaa agaatctcat tgttaccgaa      120
```

<210> SEQ ID NO 7
<211> LENGTH: 642
<212> TYPE: DNA
<213> ORGANISM: Foot-and-mouth disease virus
<220> FEATURE:
<221> NAME/KEY: misc_feature
<223> OTHER INFORMATION: Foot-and-mouth disease virus - WT Asia Lebanon
      89 3C protease sequence

<400> SEQUENCE: 7

```
agtggtgccc caccgaccga cttgcaaaag atggtcatga gcaacactaa gcctgttgag      60
ctcatccttg acggtaagac ggtggccatc tgctgcgcca ccggagtgtt tggtactgcc     120
tacctcgtgc ctcgtcacct tttcgcagaa aagtacgaca ggatcatgtt ggacggcagg     180
gccatgacag acagtgacta cagagtgttt gagtttgaga ttaaagtaaa aggacaggac     240
atgctctcag acgctgcgct catggtgctc accgtggca accgtgtgag agacatcacg     300
aaacactttc gtgatacagc aagaatgaag aaaggtaccc ccgttgtcgg cgtgatcaac     360
aacgccgacg ttgggagact gatttttctcc ggtgaggccc tcacctacaa ggacattgta    420
gtgtgcatgg atgagacac catgccgggc ctatttgcct acagagccgc taccaaggct     480
ggctactgtg gaggagccgt tcttgccaag gacggagctg acacatttat cgtcggcact    540
```

```
cactccgcag gaggcaatgg agtcgggtac tgctcatgcg tatctaggtc catgctcttg    600
aagatgaagg cacacattga ccccgaacca caccacgagt ag                      642
```

<210> SEQ ID NO 8
<211> LENGTH: 214
<212> TYPE: PRT
<213> ORGANISM: Foot-and-mouth disease virus
<220> FEATURE:
<221> NAME/KEY: MISC_FEATURE
<223> OTHER INFORMATION: Foot-and-mouth disease virus - WT Asia Lebanon
      89 3C protease sequence

<400> SEQUENCE: 8

Ser Gly Ala Pro Pro Thr Asp Leu Gln Lys Met Val Met Gly Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Thr Met Asp
    130                 135                 140

Gly Asp Thr Met Pro Gly Leu Phe Ala Tyr Lys Ala Ala Thr Lys Ala
145                 150                 155                 160

Gly Tyr Cys Gly Gly Ala Val Leu Ala Lys Asp Gly Ala Asp Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu Lys
    210

<210> SEQ ID NO 9
<211> LENGTH: 642
<212> TYPE: DNA
<213> ORGANISM: Artificial Sequence
<220> FEATURE:
<223> OTHER INFORMATION: FMDV A22 Iraq strain 3C protease with C142T
      mutation

<400> SEQUENCE: 9

```
agtggagccc caccgaccga cttgcaaaag atggtcatgg caacaccaa gcctgttgaa    60 ctcatcctcg acgggaagac ggtggccatt tgttgtgcta ccggtgtgtt tggcactgcg   120
tacctcgtgc ctcgtcatct tttttgcaga aaatatgaca agatcatgct ggacggcaga   180
gccatgacag acagtgacta cagagtgttt gagtttgaga ttaaagtaaa aggacaggac   240
atgctctcag acgctgcgct catggtactc caccgtggga atcgcgtgag agacatcacg   300
```

```
aaacactttc gtgacacagc aagaatgaag aaaggcaccc ctgttgtcgg agtaatcaac    360
aatgccgacg tcgggagact gatcttctct ggtgaggccc ttacctacaa ggacattgta    420
gtgacaatgg atggagacac catgcctggc ctgtttgcct acaaagccgc caccaaggct    480
ggctactgtg ggggagccgt tcttgctaag gacggagctg acacattcat cgttggcact    540
cactccgcag gcggcaatgg agttggatac tgctcatgcg tttccaggtc catgttgctg    600
aaaatgaagg cgcacatcga ccccgaacca caccacgaga ag                      642
```

<210> SEQ ID NO 10
<211> LENGTH: 214
<212> TYPE: PRT
<213> ORGANISM: Artificial Sequence
<220> FEATURE:
<223> OTHER INFORMATION: FMDV A22 Iraq strain 3C protease with C142T
      mutation

<400> SEQUENCE: 10

```
Ser Gly Ala Pro Pro Thr Asp Leu Gln Lys Met Val Met Gly Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Ala Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Thr Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Thr Met Asp
    130                 135                 140

Gly Asp Thr Met Pro Gly Leu Phe Ala Tyr Lys Ala Ala Thr Lys Ala
145                 150                 155                 160

Gly Tyr Cys Gly Gly Ala Val Leu Ala Lys Asp Gly Ala Asp Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Leu Lys Met Lys Ala His Ile Asp Pro
        195                 200                 205

Glu Pro His His Glu Lys
    210
```

<210> SEQ ID NO 11
<211> LENGTH: 2259
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from
      FMDV O1 Manisa isolate 87

<400> SEQUENCE: 11

```
ggagccgggc aatccagccc ggcaaccggg tcacagaacc aatcaggcaa cactgggagc      60
atcatcaaca attactacat gcagcagtac caaaactcca tggacacaca acttggtgac     120
aacgctacaa gcggaggctc aaacgagggg tccacggaca caacctccac ccacacaacc     180
aacactcaga acaacgactg gttctcgaag ctggccagtt ccgctttcag cggtcttttc     240
ggcgctcttc tcgccgacaa gaaaaccgag gagaccactc ttctagagga ccgcatcctc     300
actactcgta acggacacac cacctcgaca acccagtcga gcgttggagt cacgtacggg     360
tatgcaacag ctgaggattt cgtgagcggg ccaaacacct ctggtctcga gaccagggtt     420
gcccaggcag agcggttctt taaaacccac ctgttcgact gggtcaccag tgacccgttc     480
ggacggtgcc acctgctgga acttccaact gaccacaaag gtgtctacgg cagcctgacc     540
gactcgtatg cttatatgag gaacggctgg gatgttgaag tcactgcagt gggaaaccag     600
ttcaatggag gatgcctgtt ggtggccatg gtgccagaac tttgctccat acagaagagg     660
gagctgtacc agctcacgct ctttcctcac cagttcatca accctcggac gaacatgaca     720
gcacacatca ctgtgccctt tgttggcgtc aaccgttatg accagtacaa ggtacacaaa     780
ccttggaccc tcgtggttat ggttgtagcc cccctgaccg tcaacagtga aggtgccccg     840
caaatcaagg tgtatgccaa catcgcacct accaacgtac acgtcgcggg tgagttccct     900
tccaaagagg ggatcttccc tgtggcttgc agcgatggtt atggcggtct ggtgaccact     960
gacccgaaaa cggctgaccc cgcttacggg aaagtgttta acccccccg caacatgttg    1020
ccggggcggt tcaccaattt tcttgacgtg gctgaggcgt gccccacgtt tctccacttc    1080
gagggtgacg tgccatacgt gaccacgaag acggattcag acagggtgct cgctcagttc    1140
gacttgtctt tggcagcaaa gcacatgtcg aacaccttcc ttgcaggtct cgcccagtac    1200
tacacacagt acagcggcac catcaacctg cacttcatgt tcacagggcc tactgacgcg    1260
aaggcgcgtt acatgattgc gtatgctcct cctggcatgg aaccacctaa aacgccagag    1320
gcggctgccc actgcattca tgctgaatgg gacacagggt tgaactcaaa attcacattt    1380
tcaatcccctt acctttcggc ggctgattac gcttacacag cgtctgacac tgctgagacc    1440
acaaatgtac agggatgggt ttgcctgttt caaataacac acgggaaagc tgacggcgac    1500
gcactggtcg ttttggctag cgccggaaag gactttgagc tgcgcctgcc ggtgdatgct    1560
cgcacacaga ctacctccgc gggcgagtca gctgaccccg tgaccgccac cgttgagaat    1620
tacggtggcg agacacaggt ccagaggcgc caacacacgg acgtctcatt tatattagac    1680
agatttgtga aagtgacacc aaaagaccaa attaatgtat tggacctgat gcaaacccct    1740
gctcacactt tggtgggagc actccttcgt actgccactt actatttcgc tgacttagag    1800
gtggcagtga agcacgaggg aaaccctcacc tgggtcccga acggggcgcc tgaagcggcg    1860
ttggacaaca ccaccaaccc aacagcttac cacaaggcac cactcacccg acttgcactg    1920
ccttacacgg cgccacaccg cgtgttggct actgtttaca acgggaacag caagtatggt    1980
gacggcacgt ggccaatgt gagaggtgac ctgcaagtgt tggcccagaa ggcggcgaga    2040
gcgctgccta cctccttcaa ctacggtgcc attaaagcta ctcgggtgac tgaactgctt    2100
taccgcatga gagggctga gacatactgt ccccggcctc ttttggccat tcacccggac    2160
caggctagac acaagcagaa gattgtggca ccggtgaaac agcttctaaa ttttgacctg    2220
ctcaaattgg cgggagatgt ggagtccaac cctgggccc                          2259
```

<210> SEQ ID NO 12
<211> LENGTH: 2211
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from
      FMDV Type A (A/IRN/1/96)

<400> SEQUENCE: 12

```
ggagccggac aatccagtcc ggcaaccggg tcgcaaaacc aatcaggtaa cactggaagc      60
atcatcaaca actactacat gcaacaatac cagaattcca tggacacaca acttggagac     120
aacgccatca gcggaggctc caacgaggga tccacagaca ccacctccac ccacacaacc     180
aacacccaaa acaacgactg gttttcaaaa ttggccagct ctgcctttag cgggctcttc     240
ggtgctcttc ttgctgacaa gaagacagag gaaaccaccc tcctggaaga ccgcatcctc     300
actacccgca acggacatac cacctcaaca acccagtcga gtgtgggagt cacctacggg     360
tattccactg agaagaccca cgtttccggg cccaatacgc tggcttgga aacscgggtg      420 acacaggcag agagattttt caagaaacac ttgtttaatt ggacaactga caaacctttt     480
gggtacttgg aaaagctgga acttccact gaccacaagg gtgtttacgg acacctagtg      540
gattcttttg catacatgag aaacggctgg gacgtggagg tgtccgccgt tggcaaccag     600
ttcaacggtg gatgcctcct agtggccatg gtgcctgaat ggaaagagtt cactccacgt     660
gagaagtacc agctcacctt gttcccgcat cagttcatta gccccagaac caacatgact     720
gctcacatca cggtcccgta ccttggtgtg aatagatatg accagtacaa gaagcacaag     780
ccctggacgc tggtcgtgat ggtggtttcg ccgcttacca acagcagcat tggtgccaca     840
gaaatcaagg tctacgccaa catcgcccca acccacgttc acgtagccgg tgagctcccg     900
tcgaaagagg ggatcgtgcc ggttgcttgc tcggatgggt acggcggtct ggtgacaacg     960
gacccgaaaa cagctgaccc tgtctacggt aaggtgtaca acccgcctag gacaaactat    1020
cctgggcgct tcacaaactt gttggacgtg gccgaggctt gcccaacctt cctctgtttc    1080
gacgacggga accgtacgt tgtgacaaga gaggatgagc agcgtctact ggccaagttc      1140
gacgtctctc ttgctgcaaa gcacatgtca aacacctacc tatcagggat agcgcagtac    1200
tatgcacagt actctggcac catcaacctc cacttcatgt tcactggttc tactgactca    1260
aaagcccgct acatggtagc gtacgtcccg cccggcgtgg aaacaccgcc ggacacgcct    1320
gagagagctg cacactgcat ccacgctgag tgggacacag ggctgaactc caaattcact    1380
ttttctatcc cgtacgtgtc cgccgcggat tacgcgtaca ccgcgtctga tgtggccgaa    1440
acaacaaacg tacagggatg ggtctgcatc taccagatca cgcacgggaa ggctcaaaac    1500
gacactctgg ttgtgtcgat tagcgccggc aaggactttg agttgcgtct cccgattgac    1560
ccccgcacac agaccacatc tgccggggag tctgcagacc cagtcaccac cactgttgaa    1620
aactacggcg gtgagacaca agtccagcga cgtcaccaca ctgatgtcgg cttcataatg    1680
gacagatttg tgaagattaa caaccaccag cccacacacg tcattgacct catgcaaacc    1740
caccagcacg ggtggtggg cgctctcctg cgtgctgcca cgtactactt ctcagacctg    1800
gagattgtgg tgcgccacga aggcaacctg acgtgggtgc caatggagc accagaggca    1860 gccctgagca acgcgggcaa ccccaccgcc tacaacaaag caccattcac gaggctagca    1920 ctccccctaca ctgcgccgca ccgcgtgttg cgacggtgt acaacgggac gagcaagtac    1980
tcgacaactg gtgggcacac acggggtgac ttgggagctc ttgcggcgag ggtcgccgcc    2040
```

```
caactccctg cctctttcaa ctttggcgca atccgggcca ctgacatcag tgagcttctt    2100
gtgcgcatga agcgtgctga gctctactgc cccaggccac tactggcagt ggaagtgaca    2160
gcgcaagaca ggcacaaaca gaagatcatt gcgcctgcga aacagctcct g             2211
```

<210> SEQ ID NO 13
<211> LENGTH: 2193
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from
      FMDV Type C (Haute Loire FR/69)
<220> FEATURE:
<221> NAME/KEY: misc_feature
<222> LOCATION: (1182)..(1183)
<223> OTHER INFORMATION: n is a, c, g, or t
<220> FEATURE:
<221> NAME/KEY: misc_feature
<222> LOCATION: (1455)..(1456)
<223> OTHER INFORMATION: n is a, c, g, or t
<220> FEATURE:
<221> NAME/KEY: misc_feature
<222> LOCATION: (1708)..(1709)
<223> OTHER INFORMATION: n is a, c, g, or t
<220> FEATURE:
<221> NAME/KEY: misc_feature
<222> LOCATION: (1883)..(1885)
<223> OTHER INFORMATION: n is a, c, g, or t

<400> SEQUENCE: 13

```
ggagctgggc aatccagccc agcgaccggt tcgcagaacc aatccggtaa cactggcagc      60
ataattaaca actactatat gcagcagtac caaaactcca tggacacaca actcggcgac     120
aacgccatca gtggaggctc taatgaaggc tccacgcaca caacctctac acacacaact     180
aacacccaga caacgactg ttttccaaa cttgccagtt cagccttcag cggtcttttc      240
ggcgcccttc tcgctgataa gaaaacggag gaaaccactc tccttgaagg ccgcattctc     300
actacccgta acgggcacac gacctcgaca acccagtcga gcgtcggagt cacattcggg     360
tatgcaactg ctgaagatag cacgtctggg cccaatacat ctggtctaga gacgcgcgtt     420
catcaggcag agaggttttt caaaatggca cttttttgatt gggttccctc acaaaatttt     480
ggacacatgc acaaggttgt tctgccccat gaaccaaaag gtgtttacgg gggtcttgtc     540
aagtcatacg cgtacatgcg caatggctgg gacgtcgagg tgactgctgt tggaaaccag     600
ttcaacggcg gctgcctcct ggtggcgctc gtccccgaga tgggcgacat cagtgacagg     660
gaaaagtacc aactaaccct ttaccccac cagttcatca cccacgcac caacatgacg      720 gcacacatca ctgtgcccta cgtgggtgtc aacaggtatg accagtacaa acagcacagg     780
ccctggaccc tcgtggtcat ggttgtcgca ccactcacca aaacacagc aggtgcccaa     840 cagatcaagg tgtatgccaa catagcccca accaacgtgc acgtagcagg tgagctcccc     900
tccaaggagg ggatcttccc cgttgcgtgt tctgacggtt acggcaacat ggtgacaact     960
gacccgaaaa cggctgaccc tgcctacggg aaagtttaca cccccccg gactgctctg    1020 ccggggcggt tcacaaacta cctggatgtt gccgaggctt gtcccacctt cctgatgttc    1080
gagaacgtac cttacgtctc aacacgaact gacgggcaaa ggctactggc caagttcgac    1140
gtgtcgctgg cagcgaaaca catgtcaaac acctacttgg cnngcttggc ccagtactac    1200
acacagtatg ctgggacaat caacctacac ttcatgttca ctgggccgac cgacgcgaaa    1260
gctcggtaca tggtggcgta cgtgcccct ggcatgacg caccagacaa cccagaagag    1320
gctgcccact gcatacacgc agaatgggac actggtctga actctaagtt cacatttccc    1380
```

| | |
|---|---|
| atcccgtaca tctcggccgc tgactacgcg tacaccgcgt cccacgaggc tgaaacaaca | 1440 |
| tgtgtacagg ggtgnntctg tgtgtaccaa atcactcacg gcaaggcaga cgcagacgcg | 1500 |
| ctcgtcgtct ccgcatcagc ggggaaagac tttgagctcc ggctacctgt ggacgctaga | 1560 |
| cgacaaacta cggccactgg tgaatctgct gaccccgtca ccactaccgt tgagaactac | 1620 |
| ggaggagaga ctcaagtcca acgtcgccac cacaccgacg ttgccttcgt ccttgaccgg | 1680 |
| tttgtgaagg tcacagtgtc gggtaacnna cacacactcg acgtgatgca ggcacacaaa | 1740 |
| gacaacatcg tgggcgcgct tcttcgcgca gccacgtact acttttctga ttcggaaata | 1800 |
| gcagtgaccc acactgggaa gctcacatgg gtgcccaacg tgcaccagt ttctgcactt | 1860 |
| gacaacacaa ccaatcccac tgnnnaccac aagggcccgt tgactcgact ggctctccca | 1920 |
| tacaccgcgc cacaccgtgt gttggctacg gcgtacactg gcactacgac ctacaccgcc | 1980 |
| agtacacgcg gggatttggt tcacctagcg gcgacgcatg ctcggcactt gccgacatcg | 2040 |
| ttcaactttg gtgcagttaa agcagaaaca atcactgagt tgctcgtgcg catgaagcgt | 2100 |
| gctgaactct attgtcctag gccgattctt ccgattcagc caacgggtga tagacacaag | 2160 |
| caaccgctcg tcgcacctgc aaaacaactg ctg | 2193 |

```
<210> SEQ ID NO 14
<211> LENGTH: 2220
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived
      from FMDV SAT3 ZAM/04/96/3

<400> SEQUENCE: 14
```

| | |
|---|---|
| ggagcaggcc agtcctcacc cgccacgggg tcacaaaacc aatctggcaa cactggtagc | 60 |
| attattaata actattacat gcaacagtac caaaattcca tggacaccca gcttggcgac | 120 |
| aacgccatat caggtggttc aaatgaaggt agcacgtgaca ccacgtccac gcataccaac | 180 |
| aacacccaga acaacgattg gttttcaaaa ttggcacaat cagccatttc agggctcttc | 240 |
| ggggctctgt tggctgacaa aaagacagaa gagacaactc ttcttgagga ccgcatcctc | 300 |
| accacgcgcc acaataccac cacctcaacc acccagagct cagtgggagt gacctacgga | 360 |
| tacgcgtcag cggaccgttt cctcccgggc cccaacacca gtgggcttga gactagggtc | 420 |
| gaacaggcgg agaggttctt caaggagaaa cttttcacct ggacggctgc tcaggagtac | 480 |
| gcacacgtgc acctgcttga gctcccagtt gaccacaaag gcatctacgg tgccatggtt | 540 |
| gacacacacg catacgtgcg caacggttgg gatgtgcagg tctccgcgac cagcacccaa | 600 |
| ttcaacggtg gtactctact ggtggccatg gtgccagagc tccactcact tgacaagcgc | 660 |
| gacgtgtcac aactcacgct gttcccacac cagttcatca cccacgtac caacacgacg | 720 |
| gcacacattg tcgtcccta cgtgggggtt aacagacatg accaggtgaa actccacaaa | 780 |
| gcctggacac tggtagtggc tgtcatggca ccactcacaa catcaagcat gggccaggac | 840 |
| aacgttgagg tgtacgccaa catcgcacct accaacgtgt tgttgctgg agagatgcca | 900 |
| aacaaacaag gtatcatccc cgtagcctgc aacgatggc atggcggctt ccagaacact | 960 |
| gaccccgaaga ccgcagaccc catctacggt ctagtgtcca acgcgcctcg cacggccttc | 1020 |
| cccggaaggt tcacaaaacct tttggacgtg gccgaggcat gtccccacttt cctggattt | 1080 |
| gacggcacac cgtacgttaa gacccggcac aacagtggat ctaaaattct cacgcacatt | 1140 |
| gatttggcat ttggacacaa agctttcaag aacacgtacc ttgctgggct agcacaatac | 1200 |

```
tatgcccagt acagtggttc cctgaacctg catttcatgt acactgggcc cacgcagtca    1260
aaggcccgct tcatggttgt gtacgttcca cctgggacca acccgtccc cgacacacct    1320 gaggcggcgt cgcactgcta ccactcagaa tgggacacag gtctgaactc caagttcacg    1380
ttcacagtgc cgtacatttc ggcggccgac tttgcctaca cctactgtga tgaacctgaa    1440
caagcgtctg cacaaggctg ggttacgctc taccaggtga cagacacgca cgaccccgac    1500
tcggcggtgc tgatttcggt cagtgccggg tccgacttgg aattcaggtt gccaatcaac    1560
cccgcaccac agacaaccag tgcaggtgaa ggtgcaaatg tggtcacaac cgatgtcacc    1620
acacatggtg gtgaaacagt gcaccccagg agacagcaca ccaacgtcga gtttctgctt    1680
gacaggttca cacacattgg ggcaatgacc acttctaaga caattagcct ccttgacaca    1740
aaggaacaca cgctggtggg cgcgatcctg cgctcagcaa cgtactactt ttgtgacctg    1800
gaagtggcag tattgggtga cgcggaatgg gtagcttggg tgcccaatgg gtgcccacac    1860
accgaccggg tggaagacaa tccagtcgtt cactcgaaaa acggtgtgac ccgattcgcg    1920 ctgccttta ctgcgccaca cggtgtcctc tcaaccgtgt acaatggaac atgcaagtac    1980
tcaaagaccc aacgcgtgac tccccgacgc ggcgaccttg ccgtgttgtc cacacgtgtt    2040
gagacggaac aggaacgatg tttgcccaca gcattcaact tcggtcgatt gttgtgtgac    2100
tcgggcgacg tgtactacag gatgaagagg gcggagcttt actgcccgcg ccctctcaga    2160
gtcaggtaca cccacaccac tgacaggtac aaggtcgccc tggttaaacc agagaaacaa    2220
```

<210> SEQ ID NO 15  
<211> LENGTH: 2220  
<212> TYPE: DNA  
<213> ORGANISM: Foot-and-mouth disease virus  
<220> FEATURE:  
<221> NAME/KEY: misc_feature  
<223> OTHER INFORMATION: Wild-type P1 polyprotein precursor derived from FMDV SAT2 SEN/05/75

<400> SEQUENCE: 15

```
ggcgcaggac aatcctcacc tgctacgggc tcacaaaacc agtccggcaa cactggcagc      60
atcatcaata actactacat gcaacagtac caaaactcaa tggacactca gttgggcgac     120
aacgccatca gcggtgggtc caacgagggg tcgactgaca ccacgtcgac ccacaccaac     180
aacacccaga caacgattg gttttccaaa ttggctcaat ccgccatctc gggtcttttc     240 ggggcccctcc tggcagacaa gaaaacagag agaccactc tgctagagga ccgcatactc     300
accacacgac acggcactac tacctcaacc acacagagtt cagtaggtgt cacgtttggg     360
tacgcggacg cggatagttt cacagccggt cctaacactt ctggccttga gactcacgtt     420
ccacaagcag agaggttttt caaagaaaaa ttgtttgatt ggacaagtga caaaccattt     480
ggcacaacgt gcgtgcttga actgcccaaa gatcacaaag gcatctacgg gaagctcaac     540
gactcatacg cgtacatgag gaacggctgg gacgttcagg tcagtgctac cagcacacag     600
ttcaacggag gttccctcct tgtggctatg gtgcctgaac tcagttccat ccgtgacagg     660
gaagagttcc aaccaacact ctacccgcac cagttcataa acccacgcac caacaccacg     720
gcacacatcc aggtcccgta cctgggtgta accgccatg accagggcaa acgccaccag     780
gcgtggtctc tggttgtgat ggtgctcacg cctctcacca ctgaggcaca gatgaactct     840
gggaccgttg aggtgtacgc caacattgca cccaccaacg tgtacgtggc gggcgaactc     900
cctgggaaac agggaattgt gcccgtcgcg tgctcagacg gttacggtgg attccagaac     960
acagacccca gacggccga tccgatttac ggacatgtgt acacccccctc gcggcaagac    1020
```

```
tgtcacggtc ggttctccaa cctgttggac gtcgctgagg catgccccac actactgaac    1080
ttcgacggga aaccgtacgt tgtgacgaag agcagtgggg acaaggtaat ggccgctttt    1140
gacgtggcct tcacccacaa ggtgcacaag aacacgtttt tggcggggct ggccgactat    1200
tacacccagt acactggcag tctcaactac cacttcatgt acacaggccc cactcaccac    1260
aaagccaaat tcatggtggc atacgtccca ccagggattg cagttgcgca gctgcccaaa    1320
acaccggaag acgcttcaca ctgctaccac tctgaatggg acgggtct gaactcatct      1380 ttcacgttcg cagttcctta catctcgtct gcggacttct cctacacaca cacagacaca    1440
cccgccatgg ccacaaccaa cggctgggtt gttgtgttgc aagtcacaga cacgcactcg    1500
gcagaagccg cagtcgttgt gtccgtcagt gctgggcctg acctcgagtt caggttccca    1560
atcgaccccg ttcgccagac acatcggcg ggcgagagcg cggacgtagt gacgaccgac     1620
ccaaccacac acggtgggc agtcacaaac ccgcgacgca aacacactga cgttgctttt    1680
ctcctggaca ggtcaaccca cgttcacact gggaagacca cattcgaggt caacttgatg    1740
gacaccaagg agaaagcctt ggtgggcgcc gttctgcgcg cggccaccta ctattttgt     1800 gacttggaaa ttgcatgtgt tggtgaccac aaaagggtgt tctggcaacc caacggtgcg    1860
cccagggcga cccagttggg agacaaccca atggtcttct cccacaacaa ggtggcacgg    1920
ttcgcaatcc cgttcaccgc gccacaccgt ctgctctcca ctgtttacaa cggtgagtgt    1980
aactactcca cgtcggtgac gccgatacgt ggtgacaggg cggtcctggc ggccaagtac    2040
gccagcacca agcacacgct cccgtccact ttcaatttcg ggtacgtgac cgccgacgcg    2100
ccagtcgacg tttactaccg aatgaaaagg agcgaactct actgcccag gccactcttg     2160 ccagcgtacg accaccaatc gcacgacagg tttgatgcgc ccattggcgt agagaagcaa    2220
```

<210> SEQ ID NO 16
<211> LENGTH: 2229
<212> TYPE: DNA
<213> ORGANISM: Artificial Sequence
<220> FEATURE:
<223> OTHER INFORMATION: Wild-type P1 polyprotein precursor derived from FMDV SAT1 NIG/15/75
<220> FEATURE:
<221> NAME/KEY: misc_feature
<223> OTHER INFORMATION: Wild-type P1 polyprotein precursor derived from FMDV SAT1 NIG/15/75

<400> SEQUENCE: 16

```
ggggccggac aatccagtcc ggcaactgga tcacagaacc agtcaggcaa cacaggtagt      60
atcatcaaca actactatat gcaacagtac caaaactcga tggacacgca gctcggcgac     120
aacgccatca gcgtggctc caatgagggg tcgacagaca ccacgtcgac ccacacaaac     180
aacacccaga caacgactg gttttcaaag ctggcccggt ccgcttcag cggtttggtc      240 ggcgctctgc tcgcagacaa gaaaaccgag gaaacgactc tccttgagga ccggatcctc    300
accacgtcac acggaactac tacgtctacg acacagagtt ccgtgggagt gacgtatggg    360
tacgcttcgt ccgacaagtt tctaccaggg cccaacacca acgggctgga gactagagtc    420
gaacaggcgg agcgttactt caagcagaag ttgtttgact gggacacaac gcagaagttt    480
ggcacaaccc acatcctggc cctaccaacg gaccataagg gtgtctacgg tcaactgtta    540
gactcataca cttacatgag gaacggttgg gacgtccaag tctcggccac cgccaccccag   600 ttcaacggtg gctgtctact agtggctatg gtgcctgagc tttgctcact gagtgaccgg    660
gagaagtacc aactcactct ttttcccaca cagttcataa accccagaac caacaccact    720
```

```
gcgcacattc aggtgcctta cctgggtgtg gatcgccacg accaggggaa acgccacaag    780
gcatggaccc tggttgtcat ggtggtgtca ccgtacacga atgaccagac aatcgggtca    840
tcaaaggctg aggtgtacgt aaacatcgca ccgaccaacg tgtacgtcgc cggagagaaa    900
ccggccaaac aaggtattgt gccagtcgct gtgtccgacg gatacggcgg cttccaaaac    960
acagacccaa agacatctga cccaatttat ggtcacgttt acaatgctgc acgtaccggt   1020
taccccggga agttcagcaa cctcatggat gttgcgcagg cgtgtccaac gtttctcgac   1080
ttcaatggag caccatacgt aaccacacaa gcacattctg ggtcaaaggt catggcatgt   1140
ttcgatttgg ccttcgggca caagaacctt aaaaacacat acctctcagg cttggcacag   1200
tactacacac agtacagcgg tactttgaac ctccacttca tgtactctgg acccaccaac   1260
aacaaggcca agtacatggt tgcgtacata ccaccaggta cgcacccgct gcctgaaaca   1320
cctgaccagg cgtcccactg ttaccacgca gagtgggaca caggtctcaa ctccactttc   1380
acattcacag tgccatacat ttctggtgcg gactttgcct acacccacgc ctacgaacct   1440
gaacaatcca gcgttcaagg ttgggtgggc gtctaccaga tcactgacac ccacgagaaa   1500
gatggtgcac tgatcgtcac ggttagcgcg gggcccgacc tcgagttccg cctaccgata   1560
agccccagcc ggcagacaac aagtgctgga gaaggtgccg acgtcgtcac gaccgacgca   1620
tccgcgcacg gaggtaacac tcgccctaca cggcgggttc acaccgacgt cgcgtttctc   1680
ttggaccgtt ttactctggt tggcaagact gtggacaaca gatggtgtt agacttgctc   1740 aagacaaaag agaaggcact ggtgggcgca gtcttgcgtt ccgccacgta ctacttttca   1800
gacttggagg tagcatgtgt tggcactaac aaatgggtcg gttgggttcc taacggtgcc   1860
cctgtgccta aggaagtggg cgacaaccca gtcgtcttct cccacaacgg caccacccgt   1920
ttcgctctgc cgtacactgc tccacaccgt gtgttggcaa caacctacaa cggtgattgc   1980
aagtacaagg cccagcccgt ggagaacaga gagatccgcg gtgacatggc cgtcttggcc   2040
gctcgcgtcg ctgaggagac tcacatcccg accactttca actacgggat gatcttgacc   2100
gaaagcgaag ttgacgtcta cgtgagaatg aagagggctg agctctactg cccacgcttt   2160
ctgctcacca cgtacgacca caacggagct gacaggtaca agaccacgct ggtagcacca   2220
gagaaacaa                                                            2229
```

<210> SEQ ID NO 17
<211> LENGTH: 2196
<212> TYPE: DNA
<213> ORGANISM: Foot-and-mouth disease virus
<220> FEATURE:
<221> NAME/KEY: misc_feature
<223> OTHER INFORMATION: Wild-type P1 polyprotein precursor derived from
      FMDV Asia 1 IND 63/72

<400> SEQUENCE: 17

```
ggagccgggc aatccagccc ggcaaccggg tcgcagaacc agtcaggcaa cactggaagc     60
atcattaaca actactacat gcagcaatac cagaattcca tggacacaca acttggtgac    120
aacgctatta gcggaggctc caacgaaggt tccacggaca ccacttccac acacacaaac    180
aacacccaaa acaacgattg gttctcgcgc ctagccagtt cggccttcac cggactgttt    240
ggcgctcttt tggccgacaa gaaaacggaa gagacaaccc tgcttgaaga ccgcatcctc    300
accaccagga acggcacaca cgacgtcgac acacagtcaa cgtcggcgt gacttacggt    360 tacgctgtgg ccgaagacgc tgtttctggg cccaacacct caggcttgga gacccgcgtg    420
acacaggctg aacggttttt caagaaacac ctgtttgatt ggacaccaaa tctatcgttt    480
```

```
ggacactgtc actacctgga actcccctcc gaacacaaag gcgtgttcgg cagcctcatg    540
gactcctacg cctacatgag gaacgggtgg gacattgagg tgaccgctgt tggaaaccag    600
ttcaatggtg gttgcctcct cgtcgcactc gtcccggagc tgaaagaact tgacacgcgg    660
cagaagtacc agttgaccct cttcccacac cagttcatca acccacgcac caacatgacg    720
gctcacatca acgtgccgtt cgtgggtgtc aacaggtacg accaatacaa gctccacaag    780
ccgtggacgc ttgttgtgat ggtggtggct ccacttaccg tcaaaaccgg tggttccgaa    840
cagatcaagg tttacatgaa tgcagcacca acccacgtgc atgtggcagg ggaactgccc    900
tcgaaagagg ggatagtacc cgttgcgtgt gcggccggtt atggcaacat ggtgaccaca    960
gacccgaaga cggctgaccc cgtttacggg aaagtgttca acccccccag aacaaatctc    1020
cctgggcgct tcacaaactt ccttgatgta gcggaggcat gcccaacctt cctccgcttc    1080
ggagaagtac catttgtgaa gacggggaac tctggtgacc gcttgcttgc caagtttgac    1140
gtgtcgctcg ctgcggggca catgtccaac acctacttgg caggcttggc gcagtactac    1200
acacagtaca gcggcaccat gaacatccac ttcatgttca ccgggcccac ggatgccaaa    1260
gctcgctaca tggtggctta cgtacctcct ggtatggagc cacccacaga acccgagcgg    1320
gccgcgcact gtatacattc tgagtgggac actggtctta attccaagtt caccttttcc    1380
attccttacc tctctgctgc tgactacgct tacactgctt ctgacgtggc cgagaccacg    1440
agtgtgcagg gatgggtgtg catttatcag attacgcacg gcaaagctga aggcgacgcg    1500
ctggtcgtgt ctgtcagtgc cggcaaggac tttgagtttc gactgccagt ggatgctcgc    1560
cgagagacta ccaccgctgg cgagtccgca gacccagtca ccaccacagt tgagaactac    1620
ggaggagaga ctcagtcggc ccgacggcta cacactgacg ttgcttttgt tctcgacagg    1680
tttgtgaaac tcacccccaa gaacacccag attcttgatc tcatgcagat ccctcacac     1740 acactggttg gagcgttact ccggtccgcg acgtactact tctcggacct ggaggttgcg    1800
cttgttcaca caggctcagt cacatggggt cccaatggcg cgcccaagga cgccttggac    1860
aaccacacca acccgactgc ctaccagaag aaacccatca cccgcctggc gctcccctac    1920
accgctcccc ccgtgtgctg ggcaacagtg tacaacggga agacaacgta cgggacacaa    1980
cccacgcggc gtggtgacct tgctgttctt gcacagcggg taagcaacag gctgcccacc    2040
tccttcaact acggtgctgt gaaggctgac atcatcacgg agctgttgat ccgcatgacg    2100
cgtgcggaga catactgccc caggcctttg ctagctcttg acaccaccca cgaccgccgt    2160
aagcaggaga tcattgcacc tgagaagcaa gttttg                              2196
```

<210> SEQ ID NO 18
<211> LENGTH: 2925
<212> TYPE: DNA
<213> ORGANISM: Artificial Sequence
<220> FEATURE:
<223> OTHER INFORMATION: O1P1-3C(wt) insert

<400> SEQUENCE: 18

```
gccgccgcca tgggagccgg gcaatccagc ccggcaaccg ggtcacagaa ccaatcaggc     60
aacactggga gcatcatcaa caattactac atgcagcagt accaaaactc tatggacaca    120
caacttggtg acaacgctac aagcggaggc tcaaacgagg ggtccacgga cacaacctcc    180
acccacacaa ccaacactca gaacaacgac tggttctcga agctggccag ttccgctttc    240
agcggtcttt tcggcgctct tctcgccgac aagaaaaccg aggagaccac tcttcttgag    300
gaccgcatcc tcactactcg taacggacac accacctcga caacccagtc gagcgtagga    360
```

```
gtcacatacg ggtatgcaac ggctgaggat ttcgtgagcg ggccaaacac ctctggtctt      420
gagaccaggg ttgcccaggc agagcggttc tttaaaaccc acctgttcga ctgggtcaca      480
agtgacccgt tcggacggtg ccacctgcta gaacttccaa ctgaccacaa aggtgtctat      540
ggcagcctga ccgactcgta tgcttatatg aggaacggct gggatgttga agtcactgct      600
gtgggaaatc agttcaatgg aggatgcctg ttggtggcta tggtgccaga actttgctcc      660
atacagaaga gggagctgta ccagctcacg ctctttcctc accagttcat caaccctcgg      720
acgaacatga cagcacacat cactgtgccc tttgttggcg tcaaccgtta tgaccagtac      780
aaggtacaca aaccttggac cctcgtggtt atggttgtag ccccctgac cgtcaacagt       840 gaaggtgccc cgcaaatcaa ggtgtatgcc aacatcgcac ctaccaacgt acacgtcgcg      900
ggtgagttcc cttccaaaga ggggatcttc cctgtggctt gcagcgatgg ttatggcggt      960
ctggtgacaa ctgacccgaa aacggctgac cccgcttacg ggaaagtgtt taacccccc       1020 cgcaacatgt tgccggggcg gttcaccaat tttcttgacg tggctgaggc gtgccccacg      1080
tttctccact tcgagggtga cgtgccatac gtgaccacga agacggattc agacagggtg      1140
ctcgctcagt tcgacttgtc tttggcagca aagcacatgt ccaacacctt ccttgcaggt      1200
ctcgcccagt actacacaca gtacagcggc accatcaacc tgcacttcat gttcacaggg      1260
cctactgacg cgaaggcgcg ttacatgatt gcgtatgctc ctcctggcat ggaaccacct      1320
aaaacgccag aggcggctgc ccactgcatc catgctgaat gggacacagg ttgaactca      1380 aaattcacat tttcaatccc ttacctttcg gcggctgatt acgcttacac agcgtctgac     1440
actgctgaga ccacaaatgt acagggatgg gtttgcctgt ttcaaataac acacgggaaa     1500
gctgacggcg acgcactggt cgttttggcc agcgccggaa aggactttga gctgcgcctg     1560
ccggtggatg ctcgcacaca gactacctca gcgggcgagt cagcagaccc cgtgaccgcc     1620
accgttgaga attacggtgg cgagacacag gtccagaggc gccaacacac ggacgtgtca     1680
tttatattag acagatttgt gaaagtgaca ccaaaagacc aaattaatgt attggacctg     1740
atgcaaaccc ctgctcacac tttggtggga gcactccttc gtactgccac ttactatttc     1800
gctgacttag aggtggcagt gaagcacgag ggaaacctca cctgggtgcc gaacggggcg     1860
cctgaagcgg cgttggacaa caccaccaac ccaacagctt accacaaggc accactcacc     1920
cgacttgcac tgccttacac ggcgccacac cgcgtgttgg ctactgttta caacgggaac     1980
agcaagtatg gtgacggcac ggtggccaat gtgagaggtg atctgcaagt gttggcccag     2040
aaggcggcga gcgcgctgcc tacctccttc aactacggtg ccattaaagc tactcgggtg     2100
actgaactgc tttaccgcat gaagagggct gagacatact gtccccggcc tctttttggcc    2160 attcacccgg accaggctag acacaagcag aagattgtgg ctccggtgaa acagcttcta     2220
aattttgacc tgctcaaatt ggcggagat gtggagtcca accctgggcc cagcggccgc      2280
atgagtggtg ccccaccgac cgacttgcaa aagatggtca tgagcaacac taagcctgtt      2340
gagctcatcc ttgacggtaa gacggtggcc atctgctgcg ccaccggagt gtttggtact      2400
gcctacctcg tgcctcgtca cctttttcgca gaaaagtacg acaggatcat gttggacggc     2460
agggccatga cagacagtga ctacagagtg tttgagtttg agattaaagt aaaaggacag      2520
gacatgctct cagacgctgc gctcatggtg ctccaccgtg caaccgtgt gagagacatc        2580 acgaaacact ttcgtgatac agcaagaatg aagaaggta ccccgttgt cggcgtgatc         2640 aacaacgcca acgttgggag actgattttc tccggtgagg ccctcacctta caaggacatt      2700 gtagtgtgca tggatggaga caccatgccg ggcctatttg cctacagagc cgctaccaag       2760
```

| | |
|---|---|
| gctggctact gtggaggagc cgttcttgcc aaggacggag ctgacacatt tatcgtcggc | 2820 |
| actcactccg caggaggcaa tggagtcggg tactgctcat gcgtatctag gtccatgctc | 2880 |
| ttgaagatga aggcacacat tgaccccgaa ccacaccacg agtag | 2925 |

<210> SEQ ID NO 19
<211> LENGTH: 3047
<212> TYPE: DNA
<213> ORGANISM: Artificial Sequence
<220> FEATURE:
<223> OTHER INFORMATION: O1P1-HIV-3C(C142T) insert

<400> SEQUENCE: 19

| | |
|---|---|
| gccgccgcca tgggagccgg gcaatccagc ccggcaaccg ggtcacagaa ccaatcaggc | 60 |
| aacactggga gcatcatcaa caattactac atgcagcagt accaaaactc tatggacaca | 120 |
| caacttggtg acaacgctac aagcggaggc tcaaacgagg ggtccacgga cacaacctcc | 180 |
| acccacacaa ccaacactca gaacaacgac tggttctcga agctggccag ttccgctttc | 240 |
| agcggtcttt tcggcgctct tctcgccgac aagaaaaccg aggagaccac tcttcttgag | 300 |
| gaccgcatcc tcactactcg taacggacac accacctcga caacccagtc gagcgtagga | 360 |
| gtcacatacg ggtatgcaac ggctgaggat tcgtgagcg ggccaaacac ctctggtctt | 420 |
| gagaccaggg ttgcccaggc agagcggttc tttaaaaccc acctgttcga ctgggtcaca | 480 |
| agtgacccgt tcggacggtg ccacctgcta gaacttccaa ctgaccacaa aggtgtctat | 540 |
| ggcagcctga ccgactcgta tgcttatatg aggaacggct gggatgttga agtcactgct | 600 |
| gtgggaaatc agttcaatgg aggatgcctg ttggtggcta tggtgccaga actttgctcc | 660 |
| atacagaaga gggagctgta ccagctcacg ctctttcctc accagttcat caaccctcgg | 720 |
| acgaacatga cagcacacat cactgtgccc tttgttggcg tcaaccgtta tgaccagtac | 780 |
| aaggtacaca aaccttggac cctcgtggtt atggttgtag cccccctgac cgtcaacagt | 840 |
| gaaggtgccc cgcaaatcaa ggtgtatgcc aacatcgcac ctaccaacgt acacgtcgcg | 900 |
| ggtgagttcc cttccaaaga ggggatcttc cctgtggctt gcagcgatgg ttatggcggt | 960 |
| ctggtgacaa ctgacccgaa aacggctgac ccgcttacg ggaaagtgtt taacccccc | 1020 |
| cgcaacatgt tgccggggcg gttcaccaat tttcttgacg tggctgaggc gtgccccacg | 1080 |
| tttctccact cgagggtga cgtgccatac gtgaccacga agacggattc agacagggtg | 1140 |
| ctcgctcagt tcgacttgtc tttggcagca aagcacatgt ccaacacctt ccttgcaggt | 1200 |
| ctcgcccagt actacacaca gtacagcggc accatcaacc tgcacttcat gttcacaggg | 1260 |
| cctactgacg cgaaggcgcg ttacatgatt gcgtatgctc ctcctggcat ggaaccacct | 1320 |
| aaaacgccag aggcggctgc ccactgcatc catgctgaat gggacacagg gttgaactca | 1380 |
| aaattcacat tttcaatccc ttaccttcg gcggctgatt acgcttacac agcgtctgac | 1440 |
| actgctgaga ccacaaatgt acagggatgg gtttgcctgt tcaaataac acacgggaaa | 1500 |
| gctgacggcg acgcactggt cgttttggcc agcgccggaa aggactttga gctgcgcctg | 1560 |
| ccggtggatg ctcgcacaca gactacctca gcgggcgagt cagcagaccc cgtgaccgcc | 1620 |
| accgttgaga attacggtgg cgagacacag gtccagaggc gccaacacac ggacgtgtca | 1680 |
| tttatattag acagatttgt gaaagtgaca ccaaaagacc aaattaatgt attggacctg | 1740 |
| atgcaaaccc ctgctcacac tttggtggga gcactccttc gtactgccac ttactatttc | 1800 |
| gctgacttag aggtggcagt gaagcacgag ggaaacctca cctgggtgcc gaacggggcg | 1860 |
| cctgaagcgg cgttggacaa caccaccaac ccaacagctt accacaaggc accactcacc | 1920 |

-continued

```
cgacttgcac tgccttacac ggcgccacac cgcgtgttgg ctactgttta caacgggaac    1980
agcaagtatg gtgacggcac ggtggccaat gtgagaggtg atctgcaagt gttggcccag    2040
aaggcggcga gagcgctgcc tacctccttc aactacggtg ccattaaagc tactcgggtg    2100
actgaactgc tttaccgcat gaagagggct gagacatact gtccccggcc tcttttggcc    2160
attcacccgg accaggctag acacaagcag aagattgtgg ctccggtgaa acagcttcta    2220
aattttgacc tgctcaaatt ggcgggagat gtggagtcca accctgggcc cagcggccgc    2280 ggacctttt tagggaagat ctggccttcc tacaagggaa ggccagggaa ttttcttacg    2340
agggaccggt aaaaaaaccc gtagcactca aggttaaagc aaagaatctc attgttaccg    2400
aaagtggagc cccaccgacc gacttgcaaa agatggtcat gggcaacacc aagcctgttg    2460
aactcatcct cgacgggaag acggtggcca tttgttgtgc taccggtgtg tttggcactg    2520
cgtacctcgt gcctcgtcat cttttttgcag aaaaatatga caagatcatg ctggacggca    2580
gagccatgac agacagtgac tacagagtgt tgagtttga gattaaagta aaaggacagg    2640
acatgctctc agacgctgcg ctcatggtac tccaccgtgg gaatcgcgtg agagacatca    2700
cgaaacactt tcgtgacaca gcaagaatga agaaaggcac ccctgttgtc ggagtaatca    2760
acaatgccga cgtcgggaga ctgatcttct ctggtgaggc ccttacctac aaggacattg    2820
tagtgacaat ggatggagac accatgcctg gcctgtttgc ctacaaagcc gccaccaagg    2880
ctggctactg tggggagcc gttcttgcta aggacgagc tgcacattc atcgttggca    2940 ctcactccgc aggcggcaat ggagttggat actgctcatg cgtttccagg tccatgttgc    3000
tgaaaatgaa ggcgcacatc gaccccgaac cacaccacga gaagtaa              3047
```

<210> SEQ ID NO 20
<211> LENGTH: 558
<212> TYPE: DNA
<213> ORGANISM: Artificial Sequence
<220> FEATURE:
<223> OTHER INFORMATION: SGLuc insert

<400> SEQUENCE: 20

```
atgggagtca agttctgtt tgccctgatc tgcatcgctg tggccgaggc caagcccacc      60
gagaacaacg aagacttcaa catcgtggcc gtggccagca acttcgcgac cacggatctc    120
gatgctgacc gcgggaagtt gcccggcaag aagctgccgc tggaggtgct caaagagatg    180
gaagccaatg cccggaaagc tggctgcacc aggggctgtc tgatctgcct gtcccacatc    240
aagtgcacgc ccaagatgaa gaagtggctc caggacgct gccacaccta cgaaggcgac    300
aaagagtccg cacagggcgg cataggcgag gcgatcgtcg acattcctga gattcctggg    360
ttcaaggact tggagcccat ggagcagttc atcgcacagg tcgatctgtg tgtggactgc    420
acaactggct gcctcaaagg gcttgccaac gtgcagtgtt ctgacctgct caagaagtgg    480
ctgccgcaac gctgtgcgac cttttgccagc aagatccagg ccaggtggga caagatcaag    540 gggggccggtg gtgactaa                                                   558
```

<210> SEQ ID NO 21
<211> LENGTH: 22
<212> TYPE: DNA
<213> ORGANISM: Artificial Sequence
<220> FEATURE:
<223> OTHER INFORMATION: Synthetic primer - O1MSeq1-F

<400> SEQUENCE: 21

```
gagcatcatc aacaattact ac                                               22
```

```
<210> SEQ ID NO 22
<211> LENGTH: 22
<212> TYPE: DNA
<213> ORGANISM: Artificial Sequence
<220> FEATURE:
<223> OTHER INFORMATION: Synthetic primer - O1MSeq2-F

<400> SEQUENCE: 22
ggaccgcatc ctcactactc gt                                          22

<210> SEQ ID NO 23
<211> LENGTH: 22
<212> TYPE: DNA
<213> ORGANISM: Artificial Sequence
<220> FEATURE:
<223> OTHER INFORMATION: Synthetic primer - O1MSeq3-F

<400> SEQUENCE: 23
gccacctgct agaacttcca ac                                          22

<210> SEQ ID NO 24
<211> LENGTH: 22
<212> TYPE: DNA
<213> ORGANISM: Artificial Sequence
<220> FEATURE:
<223> OTHER INFORMATION: Synthetic primer - O1MSeq4-F

<400> SEQUENCE: 24
aggtacacaa accttggacc ct                                          22

<210> SEQ ID NO 25
<211> LENGTH: 22
<212> TYPE: DNA
<213> ORGANISM: Artificial Sequence
<220> FEATURE:
<223> OTHER INFORMATION: Synthetic primer - O1MSeq5-F

<400> SEQUENCE: 25
aacggctgac cccgcttacg gg                                          22

<210> SEQ ID NO 26
<211> LENGTH: 22
<212> TYPE: DNA
<213> ORGANISM: Artificial Sequence
<220> FEATURE:
<223> OTHER INFORMATION: Synthetic primer - O1MSeq6-F

<400> SEQUENCE: 26
gcttacacag cgtctgacac tg                                          22

<210> SEQ ID NO 27
<211> LENGTH: 22
<212> TYPE: DNA
<213> ORGANISM: Artificial Sequence
<220> FEATURE:
<223> OTHER INFORMATION: Synthetic primer - O1MSeq7-F

<400> SEQUENCE: 27
aaacctcacc tgggtgccga ac                                          22

<210> SEQ ID NO 28
<211> LENGTH: 22
<212> TYPE: DNA
<213> ORGANISM: Artificial Sequence
<220> FEATURE:
<223> OTHER INFORMATION: Synthetic primer - O1MSeq8-F
```

```
<400> SEQUENCE: 28
agatgtggag tccaaccctg gg                                           22

<210> SEQ ID NO 29
<211> LENGTH: 21
<212> TYPE: DNA
<213> ORGANISM: Artificial Sequence
<220> FEATURE:
<223> OTHER INFORMATION: Synthetic primer - O1P1-Seq-R1

<400> SEQUENCE: 29
gtccgtggac ccctcgtttg a                                            21

<210> SEQ ID NO 30
<211> LENGTH: 22
<212> TYPE: DNA
<213> ORGANISM: Artificial Sequence
<220> FEATURE:
<223> OTHER INFORMATION: Synthetic primer - O1P1-Seq-R2

<400> SEQUENCE: 30
tcgaggtggt gtgtccgtta cg                                           22

<210> SEQ ID NO 31
<211> LENGTH: 8825
<212> TYPE: DNA
<213> ORGANISM: Artificial Sequence
<220> FEATURE:
<223> OTHER INFORMATION: pMC-CMV-SV40-polyA O1P1-HIV-3C(C142T) (with
      bacterial backbone)

<400> SEQUENCE: 31
acattaccct gttatcccta gatacattac cctgttatcc cagatgacat accctgttat    60
ccctagatga cattaccctg ttatcccaga tgacattacc ctgttatccc tagatacatt   120
accctgttat cccagatgac ataccctgtt atccctagat gacattaccc tgttatccca   180
gatgacatta ccctgttatc cctagataca ttaccctgtt atcccagatg acataccctg   240
ttatccctag atgacattac cctgttatcc cagatgacat accctgtta tccctagata   300 cattaccctg ttatcccaga tgacataccc tgttatccct agatgacatt accctgttat   360
cccagatgac attaccctgt tatccctaga tacattaccc tgttatccca gatgacatac   420
cctgttatcc ctagatgaca ttaccctgtt atcccagatg acattaccct gttatcccta   480
gatacattac cctgttatcc cagatgacat accctgttat ccctagatga cattaccctg   540
ttatcccaga tgacattacc ctgttatccc tagatacatt accctgttat cccagatgac   600
ataccctgtt atccctagat gacattaccc tgttatccca gatgacatta ccctgttatc   660
cctagataca ttaccctgtt atcccagatg acataccctg ttatccctag atgacattac   720
cctgttatcc cagataaact caatgatgat gatgatgatg tcgagactc agcggccgcg   780 gtgccagggc gtgcccttgg gctccccggg cgcgactagt gaattgatac tagtattatg   840
cccagtacat gaccttatgg gactttccta cttggcagta catctacgta ttagtcatcg   900
ctattaccat ggtgatgcgg ttttggcagt acatcaatgg gcgtggatag cggtttgact   960
cacggggatt tccaagtctc cacccccattg acgtcaatgg gagtttgttt tggcaccaaa  1020
atcaacggga ctttccaaaa tgtcgtaaca actccgcccc attgacgcaa atgggcggta  1080
ggcgtgtacg gtgggaggtt tataagcag agctcgtttt agtgaaccgt cagatcgcct  1140
ggagacgcca tccacgctgt tttgacctcc atagaagatt ctagagtcga cgcggccgcg  1200
```

-continued

```
gatccgccgc cgccatggga gccgggcaat ccagcccggc aaccgggtca cagaaccaat    1260
caggcaacac tgggagcatc atcaacaatt actacatgca gcagtaccaa aactctatgg    1320
acacacaact tggtgacaac gctacaagcg gaggctcaaa cgaggggtcc acggacacaa    1380
cctccaccca cacaaccaac actcagaaca acgactggtt ctcgaagctg ccagttccg     1440
ctttcagcgg tcttttcggc gctcttctcg ccgacaagaa aaccgaggag accactcttc    1500
ttgaggaccg catcctcact actcgtaacg acacaccac ctcgacaacc cagtcgagcg     1560
taggagtcac atacgggtat gcaacggctg aggatttcgt gagcgggcca aacacctctg    1620
gtcttgagac caggggttgcc caggcagagc ggttctttaa acccaccctg ttcgactggg    1680
tcacaagtga cccgttcgga cggtgccacc tgctagaact tccaactgac cacaaaggtg    1740
tctatggcag cctgaccgac tcgtatgctt atatgaggaa cggctgggat gttgaagtca    1800
ctgctgtggg aaatcagttc aatggaggat gcctgttggt ggctatggtg ccagaacttt    1860
gctccataca aagagggag ctgtaccagc tcacgctctt tcctcaccag ttcatcaacc     1920
ctcggacgaa catgacagca cacatcactg tgccctttgt tggcgtcaac cgttatgacc    1980
agtacaaggt acacaaacct tggaccctcg tggttatggt tgtagccccc ctgaccgtca    2040
acagtgaagg tgccccgcaa atcaaggtgt atgccaacat cgcacctacc aacgtacacg    2100
tcgcgggtga gttcccttcc aaagaggga tcttccctgt ggcttgcagc gatggttatg     2160
gcggtctggt gacaactgac ccgaaaacg ctgaccccgc ttacgggaaa gtgtttaacc     2220
cccccgcaa catgttgccg gggcggttca ccaattttct tgacgtggct gaggcgtgcc    2280
ccacgtttct ccactcgag ggtgacgtgc catacgtgac cacgaagacg gattcagaca    2340
gggtgctcgc tcagttcgac ttgtcttttgg cagcaaagca catgtccaac accttccttg    2400
caggtctcgc ccagtactac acacagtaca gcggcaccat caacctgcac ttcatgttca    2460
cagggcctac tgacgcgaag gcgcgttaca tgattgcgta tgctcctcct ggcatggaac    2520
cacctaaaac gccagaggcg gctgcccact gcatccatgc tgaatgggac acagggttga    2580
actcaaaatt cacattttca atcccttacc tttcggcggc tgattacgct tacacagcgt    2640
ctgacactgt tgagaccaca aatgtacagg atgggtttg cctgttcaa ataacacacg     2700
ggaaagctga cggcgacgca ctggtcgttt tggccagcgc cggaaaggac tttgagctgc    2760
gcctgccggt ggatgctcgc acacagacta cctcagcggg cgagtcagca gaccccgtga    2820
ccgccaccgt tgagaattac ggtggcgaga cacaggtcca gaggcgccaa cacacggacg    2880
tgtcatttat attagacaga tttgtgaaag tgacaccaaa agaccaaatt aatgtattgg    2940
acctgatgca aacccctgct cacactttgg tgggagcact cctttcgtact gccacttact    3000
atttcgctga cttagaggtg gcagtgaagc acgagggaaa cctcacctgg gtgccgaacg    3060
gggcgcctga agcggcgttg gacaacacca ccaacccaac agcttaccac aaggcaccac    3120
tcacccgact tgcactgcct tacacggcgc cacaccgcgt gttggctact gtttacaacg    3180
ggaacagcaa gtatggtgac ggcacggtgg ccaatgtgag aggtgatctg caagtgttgg    3240
cccagaaggc ggcgagagcg ctgcctacct ccttcaacta cggtgccatt aaagctactc    3300
gggtgactga actgctttac cgcatgaaga gggctgagac atactgtccc cggcctcttt    3360
tggccattca cccggaccag gctagacaca agcagaagat tgtggctccg gtgaaacagc    3420
ttctaaattt tgacctgctc aaattggcgg gagatgtgga gtccaaccct gggcccagcg    3480
gccgcggacc ttttttaggg aagatctggc cttcctacaa gggaaggcca gggaattttc    3540
ttacgaggga ccggtaaaaa aacccgtagc actcaaggtt aaagcaaaga atctcattgt    3600
```

```
taccgaaagt ggagccccac cgaccgactt gcaaagatg gtcatgggca acaccaagcc      3660
tgttgaactc atcctcgacg ggaagacggt ggccatttgt tgtgctaccg gtgtgtttgg      3720
cactgcgtac ctcgtgcctc gtcatctttt tgcagaaaaa tatgacaaga tcatgctgga      3780
cggcagagcc atgacagaca gtgactacag agtgtttgag tttgagatta aagtaaaagg      3840
acaggacatg ctctcagacg ctgcgctcat ggtactccac cgtgggaatc gcgtgagaga      3900
catcacgaaa cactttcgtg acacagcaag aatgaagaaa ggcacccctg ttgtcggagt      3960
aatcaacaat gccgacgtcg ggagactgat cttctctggt gaggccctta cctacaagga      4020
cattgtagtg acaatggatg gagacaccat gcctggcctg tttgcctaca agccgccac       4080
caaggctggc tactgtgggg gagccgttct tgctaaggac ggagctgaca cattcatcgt      4140
tggcactcac tccgcaggcg gcaatggagt tggatactgc tcatgcgttt ccaggtccat      4200
gttgctgaaa atgaaggcgc acatcgaccc cgaaccacac cacgagaagt aagaattcgc      4260
tagctcgaca atcaacctct ggattacaaa atttgtgaaa gattgactgg tattcttaac      4320
tatgttgctc cttttacgct atgtggatac gctgctttaa tgcctttgta tcatgctatt      4380
gcttcccgta tggctttcat tttctcctcc ttgtataaat cctggttgct gtctctttat      4440
gaggagttgt ggcccgttgt caggcaacgt ggcgtggtgt gcactgtgtt tgctgacgca      4500
accccccactg gttggggcat tgccaccacc tgtcagctcc tttccgggac tttcgctttc      4560
cccctcccta ttgccacggc ggaactcatc gccgcctgcc ttgcccgctg ctggacaggg      4620
gctcggctgt tgggcactga caattccgtg gtgttgtcgg ggaaatcatc gtcctttcct      4680
tggctgctcg cctgtgttgc cacctggatt ctgcgcggga cgtccttctg ctacgtccct      4740
tcggccctca atccagcgga ccttccttcc cgcggcctgc tgccggctct gcggcctctt      4800
ccgcgtcttc gccttcgccc tcagacgagt cggatctccc tttgggccgc ctccccgcct      4860
ggtacccttta agaccaatga cttacaaggc agctgtagat cttagccact tttaaaga      4920
aaagggggga ctggaagggc taattcactc ccaacgaaga taagatctgc tttttgcttg      4980
tactgggtct ctctggttag accagatctg agcctgggag ctctctggct aactagggaa      5040
cccactgctt aagcctcaat aaagcttgcc ttgagtgctt caagtagtgt gtgcccgtct      5100
gttgtgtgac tctggtaact agagatccct cagacccttt tagtcagtgt ggaaaatctc      5160
tagcagtagt agttcatgtc atcttattat tcagtattta aacttgcaa agaaatgaat      5220
atcagagagt gagaggaact tgtttattgc agcttataat ggttacaaat aaagcaatag      5280
catcacaaat ttcacaaata aagcattttt ttcactgcat tctagttgtg gtttgtccaa      5340
actcatcaat gtatcttatc atgtctggct ctagctatcc cgcccctaac tccgcccatc      5400
ccgcccctaa ctccgcccag ttccgcccat tctccgcccc atggctgact aattttttt       5460
atttatgcag aggccgaggc cgcctcggcc tctgagctat tccagaagta gtgaggaggc      5520
ttttttggag gcctagactt ttgcagatcg acccatgggg gcccgcccca actgggtaa       5580
cctttgagtt ctctcagttg ggggtaatca gcatcatgat gtggtaccac atcatgatgc      5640
tgattataag aatgcggccg ccacactcta gtggatctcg agttaataat tcagaagaac      5700
tcgtcaagaa ggcgatagaa ggcgatgcgc tgcgaatcgg gagcggcgat accgtaaagc      5760
acgaggaagc ggtcagccca ttcgccgcca agctcttcag caatatcacg ggtagccaac      5820
gctatgtcct gatagcggtc cgccacaccc agccggccac agtcgatgaa tccagaaaag      5880
cggccatttt ccaccatgat attcggcaag caggcatcgc catgggtcac gacgagatcc      5940
tcgccgtcgg gcatgctcgc cttgagcctg gcgaacagtt cggctggcgc gagcccctga      6000
```

```
tgctcttcgt ccagatcatc ctgatcgaca agaccggctt ccatccgagt acgtgctcgc    6060
tcgatgcgat gtttcgcttg gtggtcgaat gggcaggtag ccggatcaag cgtatgcagc    6120
cgccgcattg catcagccat gatggatact ttctcggcag gagcaaggtg agatgacagg    6180
agatcctgcc ccggcacttc gcccaatagc agccagtccc ttcccgcttc agtgacaacg    6240
tcgagcacag ctgcgcaagg aacgcccgtc gtggccagcc acgatagccg cgctgcctcg    6300
tcttgcagtt cattcagggc accggacagg tcggtcttga caaaaagaac cgggcgcccc    6360
tgcgctgaca gccggaacac ggcggcatca gagcagccga ttgtctgttg tgcccagtca    6420
tagccgaata gcctctccac ccaagcggcc ggagaacctg cgtgcaatcc atcttgttca    6480
atcatgcgaa acgatcctca tcctgtctct tgatcagagc ttgatcccct gcgccatcag    6540
atccttggcg gcgagaaagc catccagttt actttgcagg gcttcccaac cttaccagag    6600 ggcgcccag ctggcaattc cggttcgctt gctgtccata aaaccgccca gtctagctat    6660
cgccatgtaa gcccactgca agctacctgc tttctctttg cgcttgcgtt ttcccttgtc    6720
cagatagccc agtagctgac attcatccgg ggtcagcacc gtttctgcgg actggctttc    6780
tacgtgctcg aggggggcca aacggtctcc agcttggctg ttttggcgga tgagagaaga    6840
ttttcagcct gatacagatt aaatcagaac gcagaagcgg tctgataaaa cagaatttgc    6900
ctggcggcag tagcgcggtg gtcccacctg accccatgcc gaactcagaa gtgaaacgcc    6960
gtagcgccga tggtagtgtg gggtctcccc atgcgagagt agggaactgc caggcatcaa    7020
ataaaacgaa aggctcagtc gaaagactgg gcctttcgtt ttatctgttg tttgtcggtg    7080
aacgctctcc tgagtaggac aaatccgccg ggagcggatt tgaacgttgc gaagcaacgg    7140
cccggagggt ggcgggcagg acgcccgcca taaactgcca ggcatcaaat taagcagaag    7200
gccatcctga cggatggcct ttttgcgttt ctacaaactc ttttgtttat ttttctaaat    7260
acattcaaat atgtatccgc tcatgaccaa aatcccttaa cgtgagtttt cgttccactg    7320
agcgtcagac cccgtagaaa agatcaaagg atcttcttga gatccttttt ttctgcgcgt    7380
aatctgctgc ttgcaaacaa aaaaaccacc gctaccagcg gtggtttgtt tgccggatca    7440
agagctacca actctttttc cgaaggtaac tggcttcagc agagcgcaga taccaaatac    7500
tgtccttcta gtgtagccgt agttaggcca ccacttcaag aactctgtag caccgcctac    7560
atacctcgct ctgctaatcc tgttaccagt ggctgctgcc agtggcgata agtcgtgtct    7620
taccgggttg gactcaagac gatagttacc ggataaggcg cagcggtcgg gctgaacggg    7680
gggttcgtgc acacagccca gcttggagcg aacgacctac accgaactga gatacctaca    7740
gcgtgagcta tgagaaagcg ccacgcttcc cgaagggaga aaggcggaca ggtatccggt    7800
aagcggcagg gtcggaacag gagagcgcac gagggagctt ccagggggaa acgcctggta    7860
tctttatagt cctgtcgggt ttcgccacct ctgacttgag cgtcgatttt tgtgatgctc    7920
gtcagggggg cggagcctat ggaaaaacgc cagcaacgcg gccttttac ggttcctggc    7980 cttttgctgg ccttttgctc acatgttctt cctgcgtta ccctgatt ctgtggataa    8040 ccgtattacc gcctttgagt gagctgatac cgctcgccgc agccgaacga ccgagcgcag    8100
cgagtcagtg agcgaggaag cggaagagcg cctgatgcgg tatttctcc ttacgcatct    8160 gtgcggtatt tcacaccgca tatggtgcac tctcagtaca atctgctctg atgccgcata    8220
gttaagccag tatacactcc gctatcgcta cgtgactggg tcatggctgc gccccgacac    8280
ccgccaacac ccgctgacgc gccctgacgg gcttgtctgc tcccggcatc cgcttacaga    8340
caagctgtga ccgtctccgg gagctgcatg tgtcagaggt tttcaccgtc atcaccgaaa    8400
```

```
cgcgcgaggc agcagatcaa ttcgcgcgcg aaggcgaagc ggcatgcata atgtgcctgt    8460
caaatggacg aagcagggat tctgcaaacc ctatgctact ccgtcaagcc gtcaattgtc    8520
tgattcgtta ccaattatga caacttgacg gctacatcat tcactttttc ttcacaaccg    8580
gcacggaact cgctcgggct ggccccggtg cattttttaa ataccgcgga gaaatagagt    8640
tgatcgtcaa aaccaacatt gcgaccgacg gtggcgatag gcatccgggt ggtgctcaaa    8700
agcagcttcg cctggctgat acgttggtcc tcgcgccagc ttaagacgct aatccctaac    8760
tgctggcgga aagatgtgga cagacgcgac ggcgacaagc aaacatgctg tgcgacgctg    8820
gcgat                                                                8825

<210> SEQ ID NO 32
<211> LENGTH: 28
<212> TYPE: DNA
<213> ORGANISM: Artificial Sequence
<220> FEATURE:
<223> OTHER INFORMATION: Synthetic primer - NotI-3cLeb89-F

<400> SEQUENCE: 32
cagcggccgc atgagtggtg ccccaccg                                       28

<210> SEQ ID NO 33
<211> LENGTH: 23
<212> TYPE: DNA
<213> ORGANISM: Artificial Sequence
<220> FEATURE:
<223> OTHER INFORMATION: Synthetic primer - 3CLeb89-EcoRI-R

<400> SEQUENCE: 33
gaattcctac tcgtggtgtg gtt                                            23

<210> SEQ ID NO 34
<211> LENGTH: 8703
<212> TYPE: DNA
<213> ORGANISM: Artificial Sequence
<220> FEATURE:
<223> OTHER INFORMATION: pMC-CMV-SV40-polyA O1P1-3C(wt) (with bacterial
      backbone)

<400> SEQUENCE: 34
acattaccct gttatcccta gatacattac cctgttatcc cagatgacat accctgttat    60
ccctagatga cattaccctg ttatcccaga tgacattacc ctgttatccc tagatacatt    120
accctgttat cccagatgac ataccctgtt atccctagat gacattaccc tgttatccca    180
gatgacatta ccctgttatc cctagataca ttaccctgtt atcccagatg acataccctg    240
ttatccctag atgacattac cctgttatcc agatgacat taccctgtta tcccagata    300 cattaccctg ttatcccaga tgacataccc tgttatccct agatgacatt accctgttat    360
cccagatgac attaccctgt tatccctaga tacattaccc tgttatccca gatgacatac    420
cctgttatcc ctagatgaca ttaccctgtt atccagatg acattaccct gttatcccta    480
gatacattac cctgttatcc cagatgacat accctgttat ccctagatga cattaccctg    540
ttatcccaga tgacattacc ctgttatccc tagatacatt accctgttat cccagatgac    600
ataccctgtt atccctagat gacattaccc tgttatccca gatgacatta ccctgttatc    660
cctagataca ttaccctgtt atcccagatg acataccctg ttatccctag atgacattac    720
cctgttatcc cagataaact caatgatgat gatgatgat gtcgagactc agcggccgcg    780
gtgccagggc gtgcccttgg gctccccggg cgcgactagt gaattgatac tagtattatg    840
```

```
cccagtacat gaccttatgg gactttccta cttggcagta catctacgta ttagtcatcg    900
ctattaccat ggtgatgcgg ttttggcagt acatcaatgg gcgtggatag cggtttgact    960
cacggggatt tccaagtctc caccccattg acgtcaatgg gagtttgttt tggcaccaaa   1020
atcaacggga ctttccaaaa tgtcgtaaca actccgcccc attgacgcaa atgggcggta   1080
ggcgtgtacg gtgggaggtt tatataagca gagctcgttt agtgaaccgt cagatcgcct   1140
ggagacgcca tccacgctgt tttgacctcc atagaagatt ctagagtcga cgcggccgcg   1200
gatccgccgc cgccatggga gccgggcaat ccagcccggc aaccgggtca cagaaccaat   1260
caggcaacac tgggagcatc atcaacaatt actacatgca gcagtaccaa aactctatgg   1320
acacacaact tggtgacaac gctacaagcg gaggctcaaa cgaggggtcc acggacacaa   1380
cctccaccca cacaaccaac actcagaaca cgactggttt ctcgaagctg ccagttccg    1440
ctttcagcgg tcttttcggc gctcttcctcg ccgacaagaa aaccgaggag accactcttc   1500
ttgaggaccg catcctcact actcgtaacg acacaccac ctcgacaacc cagtcgagcg    1560
taggagtcac atacgggtat gcaacggctg aggatttcgt gagcgggcca aacacctctg   1620
gtcttgagac cagggttgcc caggcagagc ggttctttaa aacccacctg ttcgactggg   1680
tcacaagtga cccgttcgga cggtgccacc tgctagaact tccaactgac cacaaaggtg   1740
tctatggcag cctgaccgac tcgtatgctt atatgaggaa cggctgggat gttgaagtca   1800
ctgctgtggg aaatcagttc aatggaggat gcctgttggt ggctatggtg ccagaacttt   1860
gctccataca gaagagggag ctgtaccagc tcacgctctt tcctcaccag ttcatcaacc   1920
ctcggacgaa catgacagca cacatcactg tgcccttgt tggcgtcaac cgttatgacc    1980
agtacaaggt acacaaacct tggaccctcg tggttatggt tgtagccccc ctgaccgtca   2040
acagtgaagg tgccccgcaa atcaaggtgt atgccaacat cgcacctacc aacgtacacg   2100
tcgcgggtga gttcccttcc aaagagggga tcttccctgt ggcttgcagc gatggttatg   2160
gcggtctggt gacaactgac ccgaaaaacg ctgaccccgc ttacgggaaa gtgtttaacc   2220
cccccgcaa catgttgccg gggcggttca ccaattttct tgacgtggct gaggcgtgcc    2280
ccacgttct ccacttcgag ggtgacgtgc catacgtgac cacgaagacg gattcagaca    2340
gggtgctcgc tcagttcgac ttgtctttgg cagcaaagca catgtccaac accttccttg   2400
caggtctcgc ccagtactac acacagtaca gcggcaccat caacctgcac ttcatgttca   2460
cagggcctac tgacgcgaag gcgcgttaca tgattgcgta tgctcctcct ggcatggaac   2520
cacctaaaac gccagaggcg gctgccact gcatccatgc tgaatgggac acagggttga    2580
actcaaaatt cacattttca atcccttacc tttcggcggc tgattacgct tacacagcgt   2640
ctgacactgc tgagaccaca aatgtacagg gatgggtttg cctgtttcaa ataacacacg   2700
ggaaagctga cggcgacgca ctggtcgttt tggccagcgc cggaaaggac tttgagctgc   2760
gcctgccggt ggatgctcgc acacagacta cctcagcggg cgagtcagca gaccccgtga   2820
ccgccaccgt tgagaattac ggtggcgaga caggtccca gaggcgccaa cacacggacg    2880
tgtcatttat attagacaga tttgtgaaag tgacaccaaa agaccaaatt aatgtattgg   2940
acctgatgca aaccccctgct cacactttgg tgggagcact ccttcgtact gccacttact   3000
atttcgctga cttagaggtg gcagtgaagc acagggaaa cctcacctgg gtgccgaacg    3060
ggcgccctga agcggcgttg gacaacacca ccaacccaac agcttaccac aaggcaccac   3120
tcacccgact tgcactgcct tacacggcgc acaccgcgt gttggctact gtttacaacg    3180
ggaacagcaa gtatggtgac ggcacggtgg ccaatgtgag aggtgatctg caagtgttgg   3240
```

-continued

```
cccagaaggc ggcgagagcg ctgcctacct ccttcaacta cggtgccatt aaagctactc   3300
gggtgactga actgctttac cgcatgaaga gggctgagac atactgtccc cggcctcttt   3360
tggccattca cccggaccag gctagacaca agcagaagat tgtggctccg gtgaaacagc   3420
ttctaaattt tgacctgctc aaattggcgg gagatgtgga gtccaaccct gggcccagcg   3480
gccgcatgag tggtgcccca ccgaccgact tgcaaaagat ggtcatgagc aacactaagc   3540
ctgttgagct catccttgac ggtaagacgg tggccatctg ctgcgccacc ggagtgtttg   3600
gtactgccta cctcgtgcct cgtcaccttt tcgcagaaaa gtacgacagg atcatgttgg   3660
acggcagggc catgacagac agtgactaca gagtgtttga gtttgagatt aaagtaaaag   3720
gacaggacat gctctcagac gctgcgctca tggtgctcca ccgtggcaac cgtgtgagag   3780
acatcacgaa acactttcgt gatacagcaa gaatgaagaa aggtaccccc gttgtcggcg   3840
tgatcaacaa cgccgacgtt gggagactga ttttctccgg tgaggccctc acctacaagg   3900
acattgtagt gtgcatggat ggagacacca tgccgggcct atttgcctac agagccgcta   3960
ccaaggctgg ctactgtgga ggagccgttc ttgccaagga cggagctgac acatttatcg   4020
tcggcactca ctccgcagga ggcaatggag tcgggtactg ctcatgcgta tctaggtcca   4080
tgctcttgaa gatgaaggca cacattgacc ccgaaccaca ccacgagtag gaattcgcta   4140
gctcgacaat caacctctgg attacaaaat ttgtgaaaga ttgactggta ttcttaacta   4200
tgttgctcct tttacgctat gtggatacgc tgctttaatg cctttgtatc atgctattgc   4260
ttcccgtatg gctttcattt tctcctcctt gtataaatcc tggttgctgt ctctttatga   4320
ggagttgtgg cccgttgtca ggcaacgtgg cgtggtgtgc actgtgtttg ctgacgcaac   4380
ccccactggt tggggcattg ccaccacctg tcagctcctt tccgggactt tcgctttccc   4440
cctccctatt gccacggcgg aactcatcgc cgcctgcctt gcccgctgct ggacaggggc   4500
tcggctgttg ggcactgaca attccgtggt gttgtcgggg aaatcatcgt cctttccttg   4560
gctgctcgcc tgtgttgcca cctggattct gcgcgggacg tccttctgct acgtcccttc   4620
ggccctcaat ccagcggacc ttccttcccg cggcctgctg ccggctctgc ggcctcttcc   4680
gcgtcttcgc cttcgccctc agacgagtcg gatctccctt gggccgcct cccgcctgg   4740 taccctttaag accaatgact acaaggcag ctgtagatct tagccacttt ttaaaagaaa   4800 agggggact ggaagggcta attcactccc aacgaagata agatctgctt tttgcttgta   4860
ctgggtctct ctggttagac cagatctgag cctgggagct ctctggctaa ctagggaacc   4920
cactgcttaa gcctcaataa agcttgcctt gagtgcttca agtagtgtgt gcccgtctgt   4980
tgtgtgactc tggtaactag agatccctca gacccttta gtcagtgtgg aaaatctcta   5040
gcagtagtag ttcatgtcat cttattattc agtatttata acttgcaaag aaatgaatat   5100
cagagagtga gaggaacttg tttattgcag cttataatgg ttacaaataa agcaatagca   5160
tcacaaattt cacaaataaa gcattttttt cactgcattc tagttgtggt ttgtccaaac   5220
tcatcaatgt atcttatcat gtctggctct agctatcccg cccctaactc cgcccatccc   5280
gcccctaact ccgcccagtt ccgcccattc tccgcccat ggctgactaa ttttttttat   5340
ttatgcagag gccgaggccg cctcggcctc tgagctattc cagaagtagt gaggaggctt   5400
ttttggaggc ctagacttt gcagatcgac ccatggggc ccgccccaac tggggtaacc   5460
tttgagttct ctcagttggg ggtaatcagc atcatgatgt ggtaccacat catgatgctg   5520
attataagaa tgcggccgcc acactctagt ggatctcgag ttaataattc agaagaactc   5580
gtcaagaagg cgatagaagg cgatgcgctg cgaatcggga gcggcgatac cgtaaagcac   5640
```

```
gaggaagcgg tcagcccatt cgccgccaag ctcttcagca atatcacggg tagccaacgc    5700
tatgtcctga tagcggtccg ccacacccag ccggccacag tcgatgaatc cagaaaagcg    5760
gccattttcc accatgatat tcggcaagca ggcatcgcca tgggtcacga cgagatcctc    5820
gccgtcgggg atgctcgcct tgagcctggc gaacagttcg gctggcgcga gccctgatg    5880 ctcttcgtcc agatcatcct gatcgacaag accggcttcc atccgagtac gtgctcgctc    5940
gatgcgatgt ttcgcttggt ggtcgaatgg gcaggtagcc ggatcaagcg tatgcagccg    6000
ccgcattgca tcagccatga tggatacttt ctcggcagga gcaaggtgag atgacaggag    6060
atcctgcccc ggcacttcgc ccaatagcag ccagtcccct cccgcttcag tgacaacgtc    6120
gagcacagct gcgcaaggaa cgcccgtcgt ggccagccac gatagccgcg ctgcctcgtc    6180
ttgcagttca ttcagggcac cggacaggtc ggtcttgaca aaaagaaccg ggcgcccctg    6240
cgctgacagc cggaacacgg cggcatcaga gcagccgatt gtctgttgtg cccagtcata    6300
gccgaatagc ctctccaccc aagcggccgg agaacctgcg tgcaatccat cttgttcaat    6360
catgcgaaac gatcctcatc ctgtctcttg atcagagctt gatcccctgc gccatcagat    6420
ccttggcggc gagaaagcca tccagtttac tttgcagggc ttcccaacct taccagaggg    6480
cgccccagct ggcaattccg gttcgcttgc tgtccataaa accgcccagt ctagctatcg    6540
ccatgtaagc ccactgcaag ctacctgctt tctctttgcg cttgcgtttt cccttgtcca    6600
gatagcccag tagctgacat tcatccgggg tcagcaccgt ttctgcggac tggctttcta    6660
cgtgctcgag gggggccaaa cggtctccag cttggctgtt ttggcggatg agaagatt    6720 ttcagcctga tacagattaa atcagaacgc agaagcggtc tgataaaaca gaatttgcct    6780
ggcggcagta gcgcggtggt cccacctgac cccatgccga actcagaagt gaaacgccgt    6840
agcgccgatg gtagtgtggg gtctccccat gcgagagtag ggaactgcca ggcatcaaat    6900
aaaacgaaag gctcagtcga aagactgggc ctttcgtttt atctgttgtt tgtcggtgaa    6960
cgctctcctg agtaggacaa atccgccggg agcggatttg aacgttgcga agcaacggcc    7020
cggagggtgg cgggcaggac gcccgccata aactgccagg catcaaatta agcagaaggc    7080
catcctgacg gatggccttt ttgcgtttct acaaactctt tgtttatttt ttctaaatac    7140
attcaaatat gtatccgctc atgaccaaaa tcccttaacg tgagttttcg ttccactgag    7200
cgtcagaccc cgtagaaaag atcaaaggat cttcttgaga tcctttttt ctgcgcgtaa    7260 tctgctgctt gcaaacaaaa aaaccaccgc taccagcggt ggtttgtttg ccggatcaag    7320
agctaccaac tcttttttccg aaggtaactg gcttcagcag agcgcagata ccaaatactg    7380
tccttctagt gtagccgtag ttaggccacc acttcaagaa ctctgtagca ccgcctacat    7440
acctcgctct gctaatcctg ttaccagtgg ctgctgccag tggcgataag tcgtgtctta    7500
ccgggttgga ctcaagacga tagttaccgg ataaggcgca gcggtcgggc tgaacggggg    7560
gttcgtgcac acagcccagc ttggagcgaa cgacctacac cgaactgaga tacctacagc    7620
gtgagctatg agaaagcgcc acgcttcccg aagggagaaa ggcggacagg tatccggtaa    7680
gcggcagggt cggaacagga gagcgcacga gggagcttcc agggggaaac gcctggtatc    7740
tttatagtcc tgtcgggttt cgccacctct gacttgagcg tcgatttttg tgatgctcgt    7800 cagggggcg agcctatgg aaaaacgcca gcaacgcggc cttttacgg ttcctggcct    7860 tttgctggcc ttttgctcac atgttctttc ctgcgttatc ccctgattct gtggataacc    7920
gtattaccgc ctttgagtga gctgataccg ctcgccgcag ccgaacgacc gagcgcagcg    7980
agtcagtgag cgaggaagcg gaagagcgcc tgatgcggta ttttctcctt acgcatctgt    8040
```

| | |
|---|---:|
| gcggtatttc acaccgcata tggtgcactc tcagtacaat ctgctctgat gccgcatagt | 8100 |
| taagccagta tacactccgc tatcgctacg tgactgggtc atggctgcgc ccgacaccc | 8160 |
| gccaacaccc gctgacgcgc cctgacgggc ttgtctgctc ccggcatccg cttacagaca | 8220 |
| agctgtgacc gtctccggga gctgcatgtg tcagaggttt tcaccgtcat caccgaaacg | 8280 |
| cgcgaggcag cagatcaatt cgcgcgcgaa ggcgaagcgg catgcataat gtgcctgtca | 8340 |
| aatggacgaa gcagggattc tgcaaaccct atgctactcc gtcaagccgt caattgtctg | 8400 |
| attcgttacc aattatgaca acttgacggc tacatcattc acttttttctt cacaaccggc | 8460 |
| acggaactcg ctcgggctgg ccccggtgca ttttttaaat acccgcgaga aatagagttg | 8520 |
| atcgtcaaaa ccaacattgc gaccgacggt ggcgataggc atccgggtgg tgctcaaaag | 8580 |
| cagcttcgcc tggctgatac gttggtcctc gcgccagctt aagacgctaa tccctaactg | 8640 |
| ctggcggaaa agatgtgaca gacgcgacgg cgacaagcaa acatgctgtg cgacgctggc | 8700 |
| gat | 8703 |

<210> SEQ ID NO 35
<211> LENGTH: 4668
<212> TYPE: DNA
<213> ORGANISM: Artificial Sequence
<220> FEATURE:
<223> OTHER INFORMATION: pMC-CMV-SV40-polyA O1P1-3C(wt) (without bacterial backbone)

<400> SEQUENCE: 35

| | |
|---|---:|
| cccttgggct ccccgggcgc gactagtgaa ttgatactag tattatgccc agtacatgac | 60 |
| cttatgggac tttcctactt ggcagtacat ctacgtatta gtcatcgcta ttaccatggt | 120 |
| gatgcggttt tggcagtaca tcaatgggcg tggatagcgg tttgactcac ggggatttcc | 180 |
| aagtctccac cccattgacg tcaatgggag tttgttttgg caccaaaatc aacgggactt | 240 |
| tccaaaatgt cgtaacaact ccgccccatt gacgcaaatg ggcggtaggc gtgtacggtg | 300 |
| ggaggtttat ataagcagag ctcgtttagt gaaccgtcag atcgcctgga cacgccatcc | 360 |
| acgctgtttt gacctccata gaagattcta gagtcgacgc ggccgcggat ccgccgccgc | 420 |
| catgggagcc gggcaatcca gcccggcaac cgggtcacag aaccaatcag caacactgg | 480 |
| gagcatcatc aacaattact acatgcagca gtaccaaaac tctatggaca cacaacttgg | 540 |
| tgacaacgct acaagcggag gctcaaacga ggggtccacg gacacaacct ccacccacac | 600 |
| aaccaacact cagaacaacg actggttctc gaagctggcc agttccgctt tcagcggtct | 660 |
| tttcggcgct cttctcgccg acaagaaaac cgaggagacc actcttcttg aggaccgcat | 720 |
| cctcactact cgtaacggac acaccacctc gacaacccag tcgagcgtag gagtcacata | 780 |
| cgggtatgca acggctgagg atttcgtgag cgggccaaac acctctggtc ttgagaccag | 840 |
| ggttgcccag gcagagcggt tctttaaaac ccacctgttc gactgggtca caagtgaccc | 900 |
| gttcggacgg tgccacctgc tagaacttcc aactgaccac aaaggtgtct atggcagcct | 960 |
| gaccgactcg tatgcttata tgaggaacgg ctgggatgtt gaagtcactg ctgtgggaaa | 1020 |
| tcagttcaat ggaggatgcc tgttggtggc tatggtgcca gaactttgct ccatacagaa | 1080 |
| gagggagctg taccagctca cgctctttcc tcaccagttc atcaaccctc ggacgaacat | 1140 |
| gacagcacac atcactgtgc cctttgttgg cgtcaaccgt tatgaccagt acaaggtaca | 1200 |
| caaaccttgg accctcgtgg ttatggttgt agccccctg accgtcaaca gtgaaggtgc | 1260 |
| cccgcaaatc aaggtgtatg ccaacatcgc acctaccaac gtacacgtcg cgggtgagtt | 1320 |

```
cccttccaaa gagggggatct tccctgtggc ttgcagcgat ggttatggcg gtctggtgac    1380
aactgacccg aaaacggctg accccgctta cgggaaagtg tttaaccccc cccgcaacat    1440
gttgccgggg cggttcacca attttcttga cgtggctgag gcgtgcccca cgtttctcca    1500
cttcgagggt gacgtgccat acgtgaccac gaagacggat tcagacaggg tgctcgctca    1560
gttcgacttg tctttggcag caaagcacat gtccaacacc ttccttgcag gtctcgccca    1620
gtactacaca cagtacagcg gcaccatcaa cctgcacttc atgttcacag gcctactga    1680
cgcgaaggcg cgttacatga ttgcgtatgc tcctcctggc atggaaccac ctaaaacgcc    1740
agaggcggct gcccactgca tccatgctga atgggacaca gggttgaact caaaattcac    1800
attttcaatc ccttaccttt cggcggctga ttacgcttac acagcgtctg acactgctga    1860
gaccacaaat gtacagggat gggtttgcct gtttcaaata acacacggga aagctgacgg    1920
cgacgcactg gtcgttttgg ccagcgccgg aaaggacttt gagctgcgcc tgccggtgga    1980
tgctcgcaca cagactacct cagcgggcga gtcagcagac cccgtgaccg ccaccgttga    2040
gaattacggt ggcgagacac aggtccagag gcgccaacac acggacgtgt catttatatt    2100
agacagattt gtgaaagtga caccaaaaga ccaaattaat gtattggacc tgatgcaaac    2160
ccctgctcac actttggtgg gagcactcct tcgtactgcc acttactatt tcgctgactt    2220
agaggtggca gtgaagcacg agggaaacct cacctgggtg ccgaacgggg cgcctgaagc    2280
ggcgttggac aacaccacca acccaacagc ttaccacaag gcaccactca cccgacttgc    2340
actgccttac acggcgccac accgcgtgtt ggctactgtt tacaacggga acagcaagta    2400
tggtgacggc acggtggcca atgtgagagg tgatctgcaa gtgttggccc agaaggcggc    2460
gagagcgctg cctacctcct tcaactacgg tgccattaaa gctactcggg tgactgaact    2520
gctttaccgc atgaagaggg ctgagacata ctgtccccgg cctcttttgg ccattcaccc    2580
ggaccaggct agacacaagc agaagattgt ggctccggtg aaacagcttc taaattttga    2640
cctgctcaaa ttggcgggag atgtggagtc caacccgggg cccagcggcc gcatgagtgg    2700
tgccccaccg accgacttgc aaaagatggt catgagcaac actaagcctg ttgagctcat    2760
ccttgacggt aagacggtgg ccatctgctg cgccaccgga gtgtttggta ctgcctacct    2820
cgtgcctcgt caccttttcg cagaaaagta cgacaggatc atgttggacg caggggccat    2880
gacagacagt gactacagag tgtttgagtt tgagattaaa gtaaaaggac aggacatgct    2940
ctcagacgct gcgctcatgg tgctccaccg tggcaaccgt gtgagagaca tcacgaaaca    3000
cttcgtgat acagcaagaa tgaagaaagg taccccgtt gtcggcgtga tcaacaacgc    3060
cgacgttggg agactgattt tctccggtga ggccctcacc tacaaggaca ttgtagtgtg    3120
catggatgga gacaccatgc cgggcctatt tgcctacaga gccgctacca aggctggcta    3180
ctgtggagga gccgttcttg ccaaggacgg agctgacaca tttatcgtcg gcactcactc    3240
cgcaggaggc aatggagtcg ggtactgctc atgcgtatct aggtccatgc tcttgaagat    3300
gaaggcacac attgaccccg aaccacacca cgagtaggaa ttcgctagct cgacaatcaa    3360
cctctggatt acaaaatttg tgaaagattg actggtattc ttaactatgt tgctcctttt    3420
acgctatgtg gatacgctgc tttaatgcct ttgtatcatg ctattgcttc ccgtatggct    3480
ttcattttct cctccttgta taaatcctgg ttgctgtctc tttatgagga gttgtggccc    3540
gttgtcaggc aacgtggcgt ggtgtgcact gtgtttgctg acgcaacccc cactggttgg    3600
ggcattgcca cccctgtca gctcctttcc gggactttcg ctttcccccct ccctattgcc    3660
acggcggaac tcatcgccgc ctgccttgcc cgctgctgga caggggctcg gctgttgggc    3720
```

```
actgacaatt ccgtggtgtt gtcggggaaa tcatcgtcct ttccttggct gctcgcctgt      3780
gttgccacct ggattctgcg cgggacgtcc ttctgctacg tcccttcggc cctcaatcca      3840
gcggaccttc cttcccgcgg cctgctgccg gctctgcggc ctcttccgcg tcttcgcctt      3900
cgccctcaga cgagtcggat ctccctttgg gccgcctccc cgcctggtac ctttaagacc      3960
aatgacttac aaggcagctg tagatcttag ccacttttta aaagaaaagg ggggactgga      4020
agggctaatt cactcccaac gaagataaga tctgcttttt gcttgtactg ggtctctctg      4080
gttagaccag atctgagcct gggagctctc tggctaacta gggaacccac tgcttaagcc      4140
tcaataaagc ttgccttgag tgcttcaagt agtgtgtgcc cgtctgttgt gtgactctgg      4200
taactagaga tccctcagac ccttttagtc agtgtggaaa atctctagca gtagtagttc      4260
atgtcatctt attattcagt atttataact tgcaaagaaa tgaatatcag agagtgagag      4320
gaacttgttt attgcagctt ataatggtta caaataaagc aatagcatca caaatttcac      4380
aaataaagca tttttttcac tgcattctag ttgtggtttg tccaaactca tcaatgtatc      4440
ttatcatgtc tggctctagc tatcccgccc ctaactccgc ccatcccgcc ctaactccg      4500 cccagttccg cccattctcc gccccatggc tgactaattt ttttatttta tgcagaggcc      4560
gaggccgcct cggcctctga gctattccag aagtagtgag gaggcttttt tggaggccta      4620
gacttttgca gatcgaccca tgggggcccg ccccaactgg ggtaacct              4668

<210> SEQ ID NO 36
<211> LENGTH: 28
<212> TYPE: DNA
<213> ORGANISM: Artificial Sequence
<220> FEATURE:
<223> OTHER INFORMATION: Synthetic primer - AscI-Kzk-Gluc-F

<400> SEQUENCE: 36
ttggcgcgcc gccaccatgg gagtcaaa                                        28

<210> SEQ ID NO 37
<211> LENGTH: 26
<212> TYPE: DNA
<213> ORGANISM: Artificial Sequence
<220> FEATURE:
<223> OTHER INFORMATION: Synthetic primer - Gluc-R-NotI

<400> SEQUENCE: 37
gcggccgctt agtcaccacc ggcccc                                          26

<210> SEQ ID NO 38
<211> LENGTH: 6430
<212> TYPE: DNA
<213> ORGANISM: Artificial Sequence
<220> FEATURE:
<223> OTHER INFORMATION: pMC-CMV-SV40-polyA SGLuc (with bacterial
      backbone)

<400> SEQUENCE: 38
acattaccct gttatcccta gatacattac cctgttatcc cagatgacat accctgttat       60
ccctagatga cattaccctg ttatcccaga tgacattacc ctgttatccc tagatacatt      120
accctgttat cccagatgac ataccctgtt atccctagat gacattaccc tgttatccca      180
gatgacatta ccctgttatc cctagataca ttaccctgtt atcccagatg acataccctg      240
ttatccctag atgacattac cctgttatcc cagatgacat accctgtta tcccctagata      300 cattaccctg ttatcccaga tgacataccc tgttatccct agatgacatt accctgttat      360
```

```
cccagatgac attaccctgt tatccctaga tacattaccc tgttatccca gatgacatac    420
cctgttatcc ctagatgaca ttaccctgtt atcccagatg acattaccct gttatcccta    480
gatacattac cctgttatcc cagatgacat accctgttat cccagatgca cattaccctg    540
ttatcccaga tgacattacc ctgttatccc tagatacatt accctgttat cccagatgac    600
ataccctgtt atccctagat gacattaccc tgttatccca gatgacatta ccctgttatc    660
cctagataca ttaccctgtt atcccagatg acatacccug ttatccctag atgacattac    720
cctgttatcc cagataaact caatgatgat gatgatgatg gtcgagactc agcggccgcg    780
gtgccagggc gtgcccttgg ctcccngggc gcgactagt gaattgatac tagtattatg    840
cccagtacat gaccttatgg gactttccta cttggcagta catctacgta ttagtcatcg    900
ctattaccat ggtgatgcgg ttttggcagt acatcaatgg gcgtggatag cggtttgact    960
cacggggatt tccaagtctc caccccattg acgtcaatgg gagtttgttt tggcaccaaa   1020
atcaacggga ctttccaaaa tgtcgtaaca actccgcccc attgacgcaa atgggcggta   1080
ggcgtgtacg gtgggaggtt tatataagca gagctcgttt agtgaaccgt cagatcgcct   1140
ggagacgcca tccacgctgt tttgacctcc atagaagatt ctagagtcga cgcggccgcg   1200
gatccttgct agcctcgaga cgcgtgattt tggcgcgccg ccaccatggg agtcaaagtt   1260
ctgtttgccc tgatctgcat cgctgtggcc gaggccaagc ccaccgagaa caacgaagac   1320
ttcaacatct ggccgtggc cagcaacttc gcgaccacgg atctcgatgc tgaccgcggg   1380
aagttgcccg gcaagaagct gccgctggag gtgctcaaag agatggaagc caatgcccgg   1440
aaagctggct gcaccagggg ctgtctgatc tgcctgtccc acatcaagtg cacgcccaag   1500
atgaagaagt ggctcccagg acgctgccac acctacgaag gcgacaaaga gtccgcacag   1560
ggcggcatag gcgaggcgat cgtcgacatt cctgagattc tgggttcaa ggacttggag   1620
cccatggagc agttcatcgc acaggtcgat ctgtgtgtgg actgcacaac tggctgcctc   1680
aaagggcttg ccaacgtgca gtgttctgac ctgctcaaga gtggctgcc gcaacgctgt   1740
gcgacctttg ccagcaagat ccagggccag gtggacaaga tcaaggggc cggtggtgac   1800
taagcggacg caaaatcagc ctcaatcttt cccgggggta ccgtcgactg cggccgcgaa   1860
ttcgctagct cgacaatcaa cctctggatt acaaaatttg tgaaagattg actggtattc   1920
ttaactatgt tgctccttt acgctatgtg gatacgctgc tttaatgcct ttgtatcatg   1980
ctattgcttc ccgtatggct ttcatttct cctccttgta taaatcctgg ttgctgtctc   2040
tttatgagga gttgtggccc gttgtcaggc aacgtggcgt ggtgtgcact gtgtttgctg   2100
acgcaaccc cactggttgg ggcattgcca ccacctgtca gctcctttcc gggactttcg   2160
ctttccccct ccctattgcc acggcggaac tcatcgccgc ctgccttgcc cgctgctgga   2220
caggggctcg gctgttgggc actgacaatt ccgtggtgtt gtcggggaaa tcatcgtcct   2280
ttccttggct gctcgcctgt gttgccacct ggattctgcg cggacgtcc ttctgctacg   2340
tcccttcggc cctcaatcca gcggaccttc cttcccgcgg cctgctgccg gctctgcggc   2400
ctcttccgcg tcttcgcctt cgccctcaga cgagtcggat ctccctttgg gccgcctccc   2460
cgcctggtac cttaagacc aatgacttac aaggcagctg tagatcttag ccactttta    2520
aaagaaaagg ggggactgga agggctaatt cactcccaac gaagataaga tctgcttttt   2580
gcttgtactg ggtctctctg gttagaccag atctgagcct gggagctctc tggctaacta   2640
gggaacccac tgcttaagcc tcaataaagc ttgccttgag tgcttcaagt agtgtgtgcc   2700
cgtctgttgt gtgactctgg taactagaga tccctcagac ccttttagtc agtgtggaaa   2760
```

```
atctctagca gtagtagttc atgtcatctt attattcagt atttataact tgcaaagaaa    2820
tgaatatcag agagtgagag gaacttgttt attgcagctt ataatggtta caaataaagc    2880
aatagcatca caaatttcac aaataaagca ttttttttcac tgcattctag ttgtggtttg    2940
tccaaactca tcaatgtatc ttatcatgtc tggctctagc tatcccgccc ctaactccgc    3000
ccatcccgcc cctaactccg cccagttccg cccattctcc gccccatggc tgactaattt    3060
tttttattta tgcagaggcc gaggccgcct cggcctctga gctattccag aagtagtgag    3120
gaggcttttt tggaggccta gacttttgca gatcgaccca tgggggcccg ccccaactgg    3180 ggtaacctttt gagttctctc agttgggggt aatcagcatc atgatgtggt accacatcat    3240
gatgctgatt ataagaatgc ggccgccaca ctctagtgga tctcgagtta ataattcaga    3300
agaactcgtc aagaaggcga tagaaggcga tgcgctgcga atcgggagcg cgataccgt     3360 aaagcacgag gaagcggtca gcccattcgc cgccaagctc ttcagcaata tcacgggtag    3420
ccaacgctat gtcctgatag cggtccgcca cacccagccg gccacagtcg atgaatccag    3480
aaaagcggcc attttccacc atgatattcg gcaagcaggc atcgccatgg gtcacgacga    3540
gatcctcgcc gtcgggcatg ctcgccttga gcctggcgaa cagttcggct ggcgcgagcc    3600
cctgatgctc ttcgtccaga tcatcctgat cgacaagacc ggcttccatc cgagtacgtg    3660
ctcgctcgat gcgatgtttc gcttggtggt cgaatgggca ggtagccgga tcaagcgtat    3720
gcagccgccg cattgcatca gccatgatgg atactttctc ggcaggagca aggtgagatg    3780
acaggagatc ctgccccggc acttcgccca atagcagcca gtcccttccc gcttcagtga    3840
caacgtcgag cacagctgcg caaggaacgc ccgtcgtggc cagccacgat agccgcgctg    3900
cctcgtcttg cagttcattc agggcaccgg acaggtcggt cttgacaaaa agaaccgggc    3960
gcccctgcgc tgacagccgg aacacggcgg catcagagca gccgattgtc tgttgtgccc    4020
agtcatagcc gaatagcctc tccacccaag cggccggaga acctgcgtgc aatccatctt    4080
gttcaatcat gcgaaacgat cctcatcctg tctcttgatc agagcttgat ccccctgcgcc    4140 atcagatcct tggcggcgag aaagccatcc agtttacttt gcagggcttc ccaaccttac    4200
cagagggcgc cccagctggc aattccggtt cgcttgctgt ccataaaacc gcccagtcta    4260
gctatcgcca tgtaagccca ctgcaagcta cctgctttct ctttgcgctt gcgttttccc    4320
ttgtccagat agcccagtag ctgacattca tccggggtca gcaccgtttc tgcggactgg    4380
ctttctacgt gctcgagggg ggccaaacgg tctccagctt ggctgttttg gcggatgaga    4440
gaagattttc agcctgatac agattaaatc agaacgcaga agcggtctga taaacagaa     4500 tttgcctggc ggcagtagcg cggtggtccc acctgacccc atgccgaact cagaagtgaa    4560
acgccgtagc gccgatggta gtgtggggtc tccccatgcg agagtaggga actgccaggc    4620
atcaaataaa acgaaaggct cagtcgaaag actgggcctt tcgttttatc tgttgtttgt    4680
cggtgaacgc tctcctgagt aggacaaatc cgccggagc ggatttgaac gttgcgaagc     4740
aacggcccgg agggtggcgg gcaggacgcc cgccataaac tgccaggcat caaattaagc    4800
agaaggccat cctgacggat ggcctttttg cgtttctaca aactcttttg tttatttttc    4860
taaatacatt caaatatgta tccgctcatg accaaaatcc cttaacgtga gttttcgttc    4920
cactgagcgt cagaccccgt agaaaagatc aaaggatctt cttgagatcc ttttttttctg    4980 cgcgtaatct gctgcttgca acaaaaaaaa ccaccgctac cagcggtggt ttgtttgccg    5040
gatcaagagc taccaactct ttttccgaag gtaactggct tcagcagagc gcagatacca    5100
aatactgtcc ttctagtgta gccgtagtta ggccaccact tcaagaactc tgtagcaccg    5160
```

```
cctacatacc tcgctctgct aatcctgtta ccagtggctg ctgccagtgg cgataagtcg    5220
tgtcttaccg ggttggactc aagacgatag ttaccggata aggcgcagcg gtcgggctga    5280
acggggggtt cgtgcacaca gcccagcttg gagcgaacga cctacaccga actgagatac    5340
ctacagcgtg agctatgaga aagcgccacg cttcccgaag ggagaaaggc ggacaggtat    5400
ccggtaagcg gcagggtcgg aacaggagag cgcacgaggg agcttccagg gggaaacgcc    5460
tggtatcttt atagtcctgt cgggtttcgc cacctctgac ttgagcgtcg attttgtga    5520 tgctcgtcag gggggcggag cctatggaaa aacgccagca acgcggcctt tttacggttc    5580
ctggcctttt gctggccttt tgctcacatg ttctttcctg cgttatcccc tgattctgtg    5640
gataaccgta ttaccgcctt tgagtgagct gataccgctc gccgcagccg aacgaccgag    5700
cgcagcgagt cagtgagcga ggaagcggaa gagcgcctga tgcggtattt tctccttacg    5760
catctgtgcg gtatttcaca ccgcatatgg tgcactctca gtacaatctg ctctgatgcc    5820
gcatagttaa gccagtatac actccgctat cgctacgtga ctgggtcatg gctgcgcccc    5880
gacacccgcc aacacccgct gacgcgccct gacgggcttg tctgctcccg gcatccgctt    5940
acagacaagc tgtgaccgtc tccgggagct gcatgtgtca gaggttttca ccgtcatcac    6000
cgaaacgcgc gaggcagcag atcaattcgc gcgcgaaggc gaagcggcat gcataatgtg    6060
cctgtcaaat ggacgaagca gggattctgc aaaccctatg ctactccgtc aagccgtcaa    6120
ttgtctgatt cgttaccaat tatgacaact tgacggctac atcattcact tttcttcac    6180 aaccggcacg gaactcgctc gggctggccc cggtgcattt tttaaatacc gcgagaaat    6240 agagttgatc gtcaaaacca acattgcgac cgacggtggc gataggcatc cgggtggtgc    6300
tcaaaagcag cttcgcctgg ctgatacgtt ggtcctcgcg ccagcttaag acgctaatcc    6360
ctaactgctg gcggaaaaga tgtgacagac gcgacggcga caagcaaaca tgctgtgcga    6420
cgctggcgat                                                           6430
```

<210> SEQ ID NO 39
<211> LENGTH: 2395
<212> TYPE: DNA
<213> ORGANISM: Artificial Sequence
<220> FEATURE:
<223> OTHER INFORMATION: pMC-CMV-SV40-polyA SGLuc (without bacterial
      backbone)

<400> SEQUENCE: 39

```
cccttgggct ccccgggcgc gactagtgaa ttgatactag tattatgccc agtacatgac      60
cttatgggac tttcctactt ggcagtacat ctacgtatta gtcatcgcta ttaccatggt     120
gatgcggttt tggcagtaca tcaatgggcg tggatagcgg tttgactcac ggggatttcc     180
aagtctccac cccattgacg tcaatgggag tttgttttgg caccaaaatc aacgggactt     240
tccaaaatgt cgtaacaact ccgccccatt gacgcaaatg ggcggtaggc gtgtacggtg     300
ggaggtttat ataagcagag ctcgtttagt gaaccgtcag atcgcctgga gacgccatcc     360
acgctgtttt gacctccata gaagattcta gagtcgacgc ggccgcggat ccttgctagc     420
ctcgagacgc gtgattttgg cgcgccgcca ccatgggagt caaagttctg tttgccctga     480
tctgcatcgc tgtggccgag gccaagccca ccgagaacaa cgaagacttc aacatcgtgg     540
ccgtggccag caacttcgcg accacggatc tcgatgctga ccgcgggaag ttgcccggca     600
agaagctgcc gctggaggtg ctcaaagaga tggaagccaa tgcccggaaa gctggctgca     660
ccaggggctg tctgatctgc ctgtcccaca tcaagtgcac gcccaagatg aagaagtggc     720
```

-continued

```
tcccaggacg ctgccacacc tacgaaggcg acaaagagtc cgcacagggc ggcataggcg    780
aggcgatcgt cgacattcct gagattcctg ggttcaagga cttggagccc atggagcagt    840
tcatcgcaca ggtcgatctg tgtgtggact gcacaactgg ctgcctcaaa gggcttgcca    900
acgtgcagtg ttctgacctg ctcaagaagt ggctgccgca acgctgtgcg acctttgcca    960
gcaagatcca gggccaggtg gacaagatca aggggccgg tggtgactaa gcggacgcaa   1020
aatcagcctc aatctttccc gggggtaccg tcgactgcgg ccgcgaattc gctagctcga   1080
caatcaacct ctggattaca aaatttgtga agattgact ggtattctta actatgttgc    1140
tccttttacg ctatgtggat acgctgcttt aatgcctttg tatcatgcta ttgcttcccg    1200
tatggctttc attttctcct ccttgtataa atcctggttg ctgtctcttt atgaggagtt   1260
gtggcccgtt gtcaggcaac gtggcgtggt gtgcactgtg tttgctgacg caaccccac    1320 tggttggggc attgccacca cctgtcagct cctttccggg actttcgctt tcccctccc    1380 tattgccacg gcggaactca tcgccgcctg ccttgcccgc tgctggacag gggctcggct   1440
gttgggcact gacaattccg tggtgttgtc ggggaaatca tcgtcctttc cttggctgct   1500
cgcctgtgtt gccacctgga ttctgcgcgg gacgtccttc tgctacgtcc cttcggccct   1560
caatccagcg gaccttcctt cccgcggcct gctgccggct ctgcgccctc ttccgcgtct   1620
tcgccttcgc cctcagacga gtcggatctc ccttttgggcc gcctcccgc ctggtacctt   1680 taagaccaat gacttacaag gcagctgtag atcttagcca ctttttaaaa gaaaaggggg   1740
gactggaagg gctaattcac tcccaacgaa gataagatct gctttttgct tgtactgggt   1800
ctctctggtt agaccagatc tgagcctggg agctctctgg ctaactaggg aacccactgc   1860
ttaagcctca ataaagcttg ccttgagtgc ttcaagtagt gtgtgcccgt ctgttgtgtg   1920
actctggtaa ctagagatcc ctcagaccct tttagtcagt gtggaaaatc tctagcagta   1980
gtagttcatg tcatcttatt attcagtatt tataacttgc aaagaaatga atatcagaga   2040
gtgagaggaa cttgtttatt gcagcttata atggttacaa ataaagcaat agcatcacaa   2100
atttcacaaa taaagcattt ttttcactgc attctagttg tggtttgtcc aaactcatca   2160
atgtatctta tcatgtctgg ctctagctat cccgcccta actccgccca tcccgcccct   2220
aactccgccc agttccgccc attctccgcc ccatggctga ctaatttttt ttatttatgc   2280
agaggccgag gccgcctcgg cctctgagct attccagaag tagtgaggag gcttttttgg   2340
aggcctagac ttttgcagat cgacccatgg gggcccgccc caactggggt aacct        2395
```